United States Patent
Benjamin et al.

(10) Patent No.: US 9,000,174 B2
(45) Date of Patent: *Apr. 7, 2015

(54) 4-PHENYLSULFONAMIDOPIPERIDINES AS CALCIUM CHANNEL BLOCKERS

(75) Inventors: Elfrida R. Benjamin, Englishtown, NJ (US); Zhengming Chen, Belle Meade, NJ (US); Deyou Sha, Yardley, PA (US); Laykea Tafesse, Robbinsville, NJ (US); Samuel F. Victory, Oak Ridge, NC (US); John W. F. Whitehead, Newtown, PA (US)

(73) Assignee: Purdue Pharma L.P., Stamford, CT (US)

( * ) Notice: Subject to any disclaimer, the term of this patent is extended or adjusted under 35 U.S.C. 154(b) by 1809 days.

This patent is subject to a terminal disclaimer.

(21) Appl. No.: 11/665,345

(22) PCT Filed: Oct. 14, 2005

(86) PCT No.: PCT/EP2005/011105
§ 371 (c)(1),
(2), (4) Date: Nov. 17, 2008

(87) PCT Pub. No.: WO2006/040181
PCT Pub. Date: Apr. 20, 2006

(65) Prior Publication Data
US 2009/0105249 A1    Apr. 23, 2009

Related U.S. Application Data

(60) Provisional application No. 60/618,419, filed on Oct. 14, 2004, provisional application No. 60/694,972, filed on Jun. 30, 2005.

(51) Int. Cl.
*C07D 211/58*     (2006.01)
*A61K 31/4545*   (2006.01)
*A61K 31/4468*   (2006.01)
*C07D 401/06*     (2006.01)
*C07D 211/96*     (2006.01)

(52) U.S. Cl.
CPC .......... *C07D 401/06* (2013.01); *C07D 211/58* (2013.01); *C07D 211/96* (2013.01)

(58) Field of Classification Search
CPC .......... C07D 211/58; A61K 31/4545; A61K 31/4468
USPC .......... 546/194, 207, 208, 223, 224; 514/318, 514/326, 329
See application file for complete search history.

(56) References Cited

U.S. PATENT DOCUMENTS

| | | |
|---|---|---|
| 4,034,098 A | 7/1977 | Archibald et al. |
| 4,131,680 A | 12/1978 | Archibald et al. |
| 4,145,427 A | 3/1979 | Langbein et al. |
| 5,028,519 A | 7/1991 | Morigaki et al. |
| 5,688,960 A | 11/1997 | Shankar |
| 5,696,267 A | 12/1997 | Reichard et al. |
| 5,723,490 A | 3/1998 | Tung |
| 5,739,135 A | 4/1998 | Biller et al. |
| 5,827,875 A | 10/1998 | Dickson, Jr. et al. |
| 5,866,589 A | 2/1999 | Romero et al. |
| 5,936,089 A | 8/1999 | Carpino et al. |
| 5,965,559 A | 10/1999 | Faull et al. |

(Continued)

FOREIGN PATENT DOCUMENTS

| | | |
|---|---|---|
| CA | 2 579 886 A1 | 3/2006 |
| EP | 1 249 233 A1 | 10/2002 |

(Continued)

OTHER PUBLICATIONS

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

(Continued)

*Primary Examiner* — David K O Dell
(74) *Attorney, Agent, or Firm* — Sterne, Kessler, Goldstein & Fox P.L.L.C.

(57) ABSTRACT

The invention relates to piperidinyl compounds of Formula (I): or a pharmaceutically acceptable salt, prodrug, or solvate thereof, wherein $R^1$-$R^3$ and Z are defined as set forth in the specification. The invention is also directed to an assay useful for identifying such compounds as N-type calcium channel modulators or blockers. The invention is also directed to the compounds of Formula (I) and compounds identified by the above assay, and the use of such compounds to treat, prevent or ameliorate a disorder responsive to the blockade of calcium channels, and particularly N-type calcium channels. Compounds of the present invention are especially useful for treating pain.

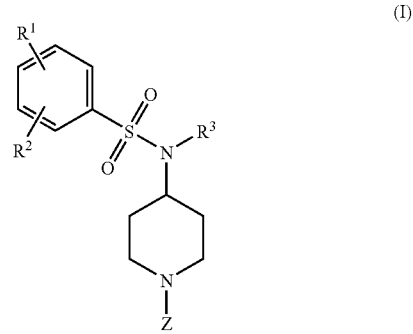

(I)

42 Claims, No Drawings

(56) References Cited

U.S. PATENT DOCUMENTS

| | | |
|---|---|---|
| 5,972,963 A | 10/1999 | Merriman et al. |
| 5,981,490 A | 11/1999 | Baxter et al. |
| 5,998,412 A | 12/1999 | Broka et al. |
| 6,011,035 A | 1/2000 | Snutch et al. |
| 6,124,341 A | 9/2000 | Tasker et al. |
| 6,130,220 A | 10/2000 | Broka et al. |
| 6,136,827 A | 10/2000 | Caldwell et al. |
| 6,136,839 A | 10/2000 | Isakson et al. |
| 6,143,744 A | 11/2000 | Broka et al. |
| 6,248,739 B1 | 6/2001 | Turner et al. |
| 6,262,046 B1 | 7/2001 | Alker et al. |
| 6,267,945 B1 | 7/2001 | Zamponi |
| 6,281,227 B1 | 8/2001 | Choi-Sledeski et al. |
| 6,294,533 B1 | 9/2001 | Snutch et al. |
| 6,303,620 B1 | 10/2001 | Hansen et al. |
| 6,310,059 B1 | 10/2001 | Snutch |
| 6,316,623 B1 | 11/2001 | Swayze et al. |
| 6,323,217 B2 | 11/2001 | Peglion et al. |
| 6,350,760 B1 | 2/2002 | Bakshi et al. |
| 6,355,631 B1 | 3/2002 | Achard et al. |
| 6,376,506 B1 | 4/2002 | Broka et al. |
| 6,380,224 B1 | 4/2002 | Dax et al. |
| 6,384,080 B1 | 5/2002 | Oku et al. |
| 6,387,897 B1 | 5/2002 | Snutch |
| 6,423,519 B1 | 7/2002 | Bergnes et al. |
| 6,458,790 B2 | 10/2002 | Palucki et al. |
| 6,492,375 B2 | 12/2002 | Snutch |
| 6,525,042 B1 | 2/2003 | Kobayashi et al. |
| 6,559,146 B1 | 5/2003 | Annoura et al. |
| 6,562,978 B1 | 5/2003 | Imamura et al. |
| 6,613,572 B2 | 9/2003 | Matsuoka et al. |
| 6,617,322 B2 | 9/2003 | Snutch |
| 6,664,273 B2 | 12/2003 | Burnett et al. |
| 6,667,319 B2 | 12/2003 | Stamford et al. |
| 6,667,342 B1 | 12/2003 | Clarke et al. |
| 6,683,093 B2 | 1/2004 | Barta et al. |
| 6,699,891 B1 | 3/2004 | Kawanishi et al. |
| 6,734,176 B2 | 5/2004 | Achard et al. |
| 6,743,790 B2 | 6/2004 | Klingler et al. |
| 6,750,228 B1 | 6/2004 | Barta et al. |
| 6,841,552 B1 | 1/2005 | Dax et al. |
| 6,894,063 B2 | 5/2005 | Greenlee et al. |
| 6,946,476 B2 | 9/2005 | Stamford et al. |
| 6,962,917 B2 | 11/2005 | Davies et al. |
| 6,987,188 B2 | 1/2006 | Dax et al. |
| 6,995,144 B2 | 2/2006 | Ozaki et al. |
| 6,998,401 B2 | 2/2006 | Annoura et al. |
| 7,045,636 B2 | 5/2006 | Palani et al. |
| 7,056,942 B2 | 6/2006 | Hildesheim et al. |
| 7,067,507 B2 | 6/2006 | Pulley et al. |
| 7,109,207 B2 | 9/2006 | Burnett et al. |
| 7,132,443 B2 | 11/2006 | Haffner et al. |
| 7,183,413 B2 | 2/2007 | Lin et al. |
| 7,205,408 B2 | 4/2007 | Davies et al. |
| 7,262,206 B2 | 8/2007 | Heckel et al. |
| 7,268,150 B2 | 9/2007 | Hayakawa et al. |
| 7,405,210 B2 | 7/2008 | Bradley et al. |
| 7,449,482 B2 | 11/2008 | Cheng et al. |
| 7,534,892 B2 | 5/2009 | Nakatani |
| 7,544,690 B2 | 6/2009 | Sekiguchi et al. |
| 7,598,391 B2 | 10/2009 | Murray et al. |
| 7,786,308 B2 | 8/2010 | Drutu et al. |
| 7,868,205 B2 | 1/2011 | Moradei et al. |
| 7,951,801 B2 | 5/2011 | Hepperle et al. |
| 7,964,613 B2 | 6/2011 | Matsubara et al. |
| 2001/0029258 A1 | 10/2001 | Snutch |
| 2001/0056184 A1 | 12/2001 | Noda et al. |
| 2002/0013310 A1 | 1/2002 | Choi-Sledeski et al. |
| 2002/0055457 A1 | 5/2002 | Janus et al. |
| 2002/0092732 A1 | 7/2002 | Margaria |
| 2002/0094989 A1 | 7/2002 | Hale et al. |
| 2002/0115863 A1 | 8/2002 | Patel et al. |
| 2002/0128476 A1 | 9/2002 | Marquis, Jr. et al. |
| 2002/0151712 A1 | 10/2002 | Lin et al. |
| 2002/0176461 A1 | 11/2002 | Nihei et al. |
| 2003/0006081 A1 | 1/2003 | Burke et al. |
| 2003/0029258 A1 | 2/2003 | Davies et al. |
| 2003/0045530 A1 | 3/2003 | Snutch |
| 2003/0092732 A1 | 5/2003 | Yu et al. |
| 2003/0130265 A1 | 7/2003 | Pouzet et al. |
| 2003/0158186 A1 | 8/2003 | Malik et al. |
| 2003/0176461 A1 | 9/2003 | Egle et al. |
| 2003/0216380 A1 | 11/2003 | Josien et al. |
| 2003/0225060 A1 | 12/2003 | Ujjainwalla et al. |
| 2003/0229067 A1 | 12/2003 | Castelhano et al. |
| 2003/0232808 A1 | 12/2003 | Kobayashi et al. |
| 2003/0236283 A1 | 12/2003 | Radeke et al. |
| 2004/0006081 A1 | 1/2004 | Burrows et al. |
| 2004/0006089 A1 | 1/2004 | Thurieau et al. |
| 2004/0014745 A1 | 1/2004 | Yamada et al. |
| 2004/0067947 A1 | 4/2004 | Wathen et al. |
| 2004/0102431 A1 | 5/2004 | Boss et al. |
| 2004/0102450 A1 | 5/2004 | Ewing et al. |
| 2004/0152692 A1 | 8/2004 | Dhanak et al. |
| 2004/0186148 A1 | 9/2004 | Shankar et al. |
| 2004/0224901 A1 | 11/2004 | Chaturvedula et al. |
| 2004/0236283 A1 | 11/2004 | Tang |
| 2005/0014789 A1 | 1/2005 | Andrews et al. |
| 2005/0032773 A1 | 2/2005 | Piot-Grosjean et al. |
| 2005/0043535 A1 | 2/2005 | Aissaoui et al. |
| 2005/0070534 A1 | 3/2005 | Carruthers et al. |
| 2005/0085518 A1 | 4/2005 | Dai et al. |
| 2005/0119266 A1 | 6/2005 | Shi et al. |
| 2005/0153980 A1 | 7/2005 | Schadt et al. |
| 2005/0165065 A1 | 7/2005 | Pajouhesh et al. |
| 2005/0197336 A1 | 9/2005 | Anandan et al. |
| 2005/0239796 A1 | 10/2005 | Thurieau et al. |
| 2005/0245573 A1 | 11/2005 | Neitzel et al. |
| 2005/0250784 A1 | 11/2005 | Anandan et al. |
| 2005/0277647 A1 | 12/2005 | Link et al. |
| 2005/0282831 A1 | 12/2005 | Beauglehole et al. |
| 2006/0014761 A1 | 1/2006 | Morgan et al. |
| 2006/0014783 A1 | 1/2006 | Aissaoui et al. |
| 2006/0058287 A1 | 3/2006 | Axten et al. |
| 2007/0043081 A1 | 2/2007 | Bur et al. |
| 2007/0104644 A1 | 5/2007 | Cuthbertson et al. |
| 2007/0179180 A1 | 8/2007 | Busch-Petersen et al. |
| 2007/0293477 A1 | 12/2007 | Casillas et al. |
| 2008/0103139 A1 | 5/2008 | Ishizuka et al. |
| 2009/0048227 A1 | 2/2009 | Chakravarty et al. |
| 2009/0239910 A1 | 9/2009 | Chen et al. |
| 2009/0306136 A1 | 12/2009 | Matsumura et al. |
| 2010/0022595 A1 | 1/2010 | Chen et al. |
| 2010/0063030 A1 | 3/2010 | Kyle et al. |
| 2010/0216841 A1 | 8/2010 | Barrow et al. |
| 2010/0311792 A1 | 12/2010 | Shao et al. |
| 2011/0098281 A9 | 4/2011 | Kyle et al. |

FOREIGN PATENT DOCUMENTS

| | | |
|---|---|---|
| EP | 1 254 895 A1 | 11/2002 |
| EP | 1 702 916 A1 | 9/2006 |
| GB | 1 445 595 A | 8/1976 |
| GB | 2 000 136 A | 1/1979 |
| GB | 2 352 240 A | 1/2001 |
| JP | 5-201971 A | 8/1993 |
| JP | 2005-154380 A | 6/2005 |
| JP | 2005/154830 A | 6/2005 |
| JP | 2005/179351 A | 7/2005 |
| JP | 2006-83133 A | 3/2006 |
| JP | 2006-83137 A | 3/2006 |
| WO | WO 90/15600 A2 | 12/1990 |
| WO | WO 93/22283 A1 | 11/1993 |
| WO | WO 97/45119 A1 | 12/1997 |
| WO | WO 99/01451 A1 | 1/1999 |
| WO | WO 99/44596 A2 | 9/1999 |
| WO | WO 99/47508 A1 | 9/1999 |
| WO | WO 00/37059 A2 | 6/2000 |
| WO | WO 00/42011 A1 | 7/2000 |
| WO | WO 01/04087 A1 | 1/2001 |
| WO | WO 01/44179 A1 | 6/2001 |
| WO | WO 01/45709 A1 | 6/2001 |
| WO | WO 01/49670 A1 | 7/2001 |
| WO | WO 01/70708 A1 | 9/2001 |

(56) References Cited

FOREIGN PATENT DOCUMENTS

| | | |
|---|---|---|
| WO | WO 01/81308 A2 | 11/2001 |
| WO | WO 01/87839 A1 | 11/2001 |
| WO | WO 0187839 A1 * | 11/2001 |
| WO | WO 01/24786 A1 | 12/2001 |
| WO | WO 02/22592 A2 | 3/2002 |
| WO | WO 02/24649 A1 | 3/2002 |
| WO | WO 02/49648 A2 | 4/2002 |
| WO | WO 02/42257 A1 | 5/2002 |
| WO | WO 02/070479 A1 | 9/2002 |
| WO | WO 03/013527 A1 | 2/2003 |
| WO | WO 03/022277 A1 | 3/2003 |
| WO | WO 03/024456 A1 | 3/2003 |
| WO | WO 02/49648 A1 | 6/2003 |
| WO | WO 03/045977 A2 | 6/2003 |
| WO | WO 03/048154 A1 | 6/2003 |
| WO | WO 03/051868 A1 | 6/2003 |
| WO | WO 03/059265 A2 | 7/2003 |
| WO | WO03059265 A2 * | 7/2003 |
| WO | WO 03/079025 A2 | 9/2003 |
| WO | WO 03/084542 A1 | 10/2003 |
| WO | WO 2004/009549 A2 | 1/2004 |
| WO | WO 2004/055006 A1 | 7/2004 |
| WO | WO 2004/058709 A1 | 7/2004 |
| WO | WO 2004/058736 A1 | 7/2004 |
| WO | WO 2004/083167 A1 | 9/2004 |
| WO | WO 2004/105750 A1 | 12/2004 |
| WO | WO 2004/111014 A1 | 12/2004 |
| WO | WO 2005/004497 A1 | 1/2005 |
| WO | WO 2005/011697 A2 | 2/2005 |
| WO | WO 2005/030209 A1 | 4/2005 |
| WO | WO 2005/044797 A1 | 5/2005 |
| WO | WO 2005/090296 A2 | 9/2005 |
| WO | WO 2005/095418 A1 | 10/2005 |
| WO | WO 2005/097779 A1 | 10/2005 |
| WO | WO 2006/030211 A2 | 3/2006 |
| WO | WO 2006/105127 A2 | 10/2006 |
| WO | WO 2006/134481 A1 | 12/2006 |
| WO | WO 2007/052843 A1 | 5/2007 |
| WO | WO 2007/067617 A2 | 6/2007 |
| WO | WO 2007/075524 A2 | 7/2007 |
| WO | WO 2007/110449 A1 | 10/2007 |
| WO | WO 2007/118853 A1 | 10/2007 |
| WO | WO 2007/118854 A1 | 10/2007 |
| WO | WO 2008/050200 A1 | 5/2008 |
| WO | WO 2008/051873 A2 | 5/2008 |
| WO | WO 2008/061016 A1 | 5/2008 |
| WO | WO 2008/124118 | 10/2008 |
| WO | WO 2009/040659 A2 | 4/2009 |

OTHER PUBLICATIONS

West, Anthony R., Solid State Chemistry and its Applications, Wiley, New York, 1988, pp. 358 & 365.*
Chemical Abstracts Registry No. 402929-10-6 Mar. 27, 2002.*
Chemical Abstracts Registry No. 397244-98-3 Mar. 1, 2002.*
Bergeron, R.J., et al., "Polyamine Analogue Regulation of NMDA MK-801 Binding: a Structure-Activity Study," *J. Med. Chem.* 39:5257-5266, American Chemical Society (1996).
Brower, V., "New paths to pain relief," *Nat. Biotechnol.* 18:387-388, Nature America Publishing (2000).
Caulfield, W.L., et al., "The First Potent and Selective Inhibitors of the Glycine Transporter Type 2," *J. Med. Chem.* 44:2679-2682, American Chemical Society (2001).
Cox, B., "Calcium Channel Blockers and Pain Therapy," *Curr. Rev. Pain* 4:488-498, National Library of Medicine (2000).
Davila, H.M., "Molecular and Functional Diversity of Voltage-Gated Calcium Channels," *Ann. NY Acad. Sci.* 868:102-117, The New York Academy of Sciences (1999).
Dubel, S.J., et al., "Molecular cloning of the α-1 subunit of an ω-conotoxin-sensitive calcium channel," *Proc. Natl. Acad. Sci. U.S. A.* 89:5058-5062, National Academy of Sciences (1992).
Eidelman, O., and Cabantchik, Z.I., "Continuous monitoring of transport by fluorescence on cells and vesicles," *Biochim. Biophy. Acta* 988:319-334, Elsevier Science Publishers B.V. (1989).

Finney, Z.G., and Riley, T.N., "4-Anilidopiperidine Analgesics. 3. 1-Substituted 4-(Propananilino)perhydroazepines as Ring-Expanded Analogues," *J. Med. Chem.* 23:895-899, American Chemical Society (1980).
Gould, R.J., et al., "Antischizophrenic drugs of the diphenylbutylpiperidine type act as calcium channel antagonists," *Proc. Natl. Acad. Sci. USA* 80:5122-5125, National Academy of Sciences (1983).
Grinvald, A., et al., "Fluorescence Monitoring of Electrical Responses From Small Neurons and Their Processes," *Biophys. J.* 42:195-198, Biophysical Society (1983).
Grinvald, A., "Real-Time Optical Mapping of Neuronal Activity: From Single Growth Cones to the Intact Mammalian Brain," *Ann. Rev. Neurosci.* 8:263-305, Annual Reviews Inc. (1985).
Grynkiewicz, G., et al., "A New Generation of $Ca^{2+}$ Indicators with Greatly Improved Fluorescence Properties," *J. Biol. Chem.* 260:3440-3450, The American Chemical Society of Biological Chemists, Inc. (1985).
Hamill, O.P., et al., "Improved Patch-Clamp Techniques for High-Resolution Current Recording from Cells and Cell-Free Membrane Patches," *Pflügers Arch.* 391:85-100, Springer-Verlag (1981).
Hansen, H.C., et al., "Multistep Solution-Phase Parallel Synthesis of Spiperone Analogues," *Bioorg. Med. Chem. Letts.* 10:2435-2439, Elsevier Science Ltd. (2000).
Hosford, D.A., et al., "A radiohistochemical measure of [$^3$H]TCP binding to the activated NMDA-receptor-gated icon channel in rat brain," *Brain Res.* 616:192-200, Elsevier Science Publishers B.V. (1990).
Hu, L.-Y., et al., "The Discovery of [1-(4-Dimethylamino-benzyl)-piperidin-4-yl]-[4-(3,3-dimethylbutyl)-phenyl]-(3-methyl-but-2-enyl)-Amine, an N-type $Ca^{+2}$ Channel Blocker with Oral Activity for Analgesia," *Bioorg. Med. Chem.* 8:1203-1212, Elsevier Science (2000).
Hu, L-Y., et al., "Structure-Activity Relationship of N-Methyl-N-Aralkyl-Peptidylamines as Novel N-Type Calcium Channel Blockers," *Bioorg. Med. Chem. Lett.* 9:2151-2156, Elsevier Science Ltd. (1999).
Hu, L-Y., et al., "Synthesis of a Series of 4-Benzyloxyaniline Analogues as Neuronal N-Type Calcium Channel Blockers with Improved Anticonvulsant and Analgesic Properties," *J. Med. Chem.* 42:4239-4249, American Chemical Society (1999).
Hunskaar, S., et al., "Formalin test in mice, a useful technique for evaluating mild analgesics," *J. Neurosci. Meth.* 14:69-76, Elsevier Publishers B.V. (1985).
Ito, M., "Long-Term Depression," *Ann. Rev. Neurosci.* 12:85-102, Annual Reviews Inc. (1989).
Janis, R.A., and Triggle, D.J., "Drugs Acting on Calcium Channels," in *Calcium Channels: Their Properties, Functions, Regulations, and Clinical Relevance*, Hurwitz et al., eds., CRC Press, London, pp. 195-249 (1991).
Kim, H-L., et al., "Rat brain expresses an alternatively spliced form of the dihydropyridine- sensitive L-type calcium channel α2 subunit," *Proc. Natl. Acad. Sci. U.S.A.* 89:3251-3255, National Academy of Sciences (1992).
Kim, S.H., and Chung, J.M., "An experimental model for peripheral neuropathy produced by segmental spinal nerve ligation in the rat," *Pain* 50:355-363, Elsevier Science Publishers B.V. (1992).
Koch, W.J., et al., "cDNA Cloning of a Dihydropyridine-sensitive Calcium Channel from Rat Aorta. Evidence for the Existence of Alternatively Spliced Forms," *J. Biol. Chem.* 265:17786-17791, The American Society for Biochemistry and Molecular Biology, Inc. (1990).
Lin, Z., et al., "Identification of Functionally Distinct Isoforms of the N-Type $Ca^{2+}$ Channel in Rat Sympathetic Ganglia and Brain," *Neuron* 18:153-166, Cell Press (1997).
Loew, L.M., et al., "Charge-Shift Probes of Membrane Potential. A Probable Electrochromic Mechanism for p-Aminostrylpyridinium Probes on a Hemispherical Lipid Bilayer," *Biophys. J.* 34:353-365, Biophysical Society (1981).
Lowe, J.A., et al., "Nuclear Variation of Quinuclidine Substance P Antagonists: 2-Diphenylmethyl-1-azabicyclo[3.2.2]nonan-3-amines," *Bioorg. Med. Chem. Letts.* 3:921-924, Pregamon Press Ltd. (1993).

(56) References Cited

OTHER PUBLICATIONS

Lukyanetz, E.A., "Selective Blockade of N-Type Calcium Channels by Levetiracetam," *Epilepsia* 43:9-18, Blackwell Publishing (2002).

Neher, E., and Salcrnann, B., "The Patch Clamp Technique. A simple procedure can easily isolate ion channel on cell membranes. Its Nobel Prize-winning developers explain what the technique has revealed about cellular signaling," *Sci. Ameri.* 266:44-51, Scientific American (1992).

Nielsen, K.J., et al., "Structure-activity relationships of ω-conotoxins at N-type voltage-sensitive calcium channels," *J. Mol. Recognit.* 13:55-70, John Wiley & Sons, Ltd. (2000).

Nuglisch, J., et al., "Protective Effect of Nimodipine Against Ischemic Neuronal Damage in Rat Hippocampus Without Changing Postischemic Cerebral Blood Flow," *J. Cereb. Blood Flow Metab.* 10:654-659, Raven Press Ltd. (1990).

Pragnell, M., et al., "Cloning and tissue-specific expression of the brain calcium channel β-subunit," *FEBS Lett.* 291:253-258, Elsevier Science B.V. (1991).

Rolland, C., et al., "G-Protein-Coupled Receptor Affinity Prediction Based on the Use of Profiling Dataset: QSAR Design, Synthesis, and Experimental Validation," *J. Med. Chem.* 48:6563-6574, American Chemical Society (Sep. 2005).

Romero, M., et al., "New Advances in the Field of Calcium Channel Antagonists: Cardiovascular Effects and Structure-Activity Relationships," *Curr. Med. Chem. Cardiovasc. Hematol. Agents.* 1:113-141, Bentham Science Publishers Ltd. (Jun. 2003).

Scarpa, A., "Measurements of Cation Transport with Metallochromic Indicators," *Meth. Enzymol.* 56:301-338, Academic Press (1979).

Schwartz, A., et al., "Receptors for Calcium Antagonists," *Am. J. Cardiol.* 62:3G-6G, Cahners Publishing Company (1988).

Seko, T., et al., Structure-Activity Study and Analgesic Efficacy of Amino Acid Derivatives as N-Type Calcium Channel Blockers, *Bioorg. Med. Chem. Letts.* 11:2067-2070, Elsevier Science Ltd. (2001).

Seko, T., et al., "Structure-Activity Study of L-Cysteine-Based N-Type Calcium Channel Blockers: Optimization of N- and C-Terminal Substituents," *Bioorg. Med. Chem. Letts.* 12:915-918, Elsevier Science Ltd. (2002).

Seko, T., et al., "L-Cysteine Based N-type Calcium Channel Blockers: Structure-Activity Relationships of the C-Terminal Lipophilic Moiety, and Oral Analgesic Efficacy in Rat Pain Models," *Bioorg. Med. Chem. Letts.* 12:2267-2269, Elsevier Science Ltd. (2002).

Seko, T., et al., "Structure-Activity Study of L-Amino Acid-Based N-Type Calcium Channel Blockers," *Bioorg. Med. Chem.* 11:1901-1913, Elsevier Science Ltd. (Apr. 2003).

Song, Y., et al., "(S)-4-Methyl-2-(methylamino)pentanoic Acid [4,4-Bis(4-fluorophenyl)butyl]amide Hydrochloride, a Novel Calcium Channel Antagonist, Is Efficacious in Several Animal Models of Pain," *J. Med. Chem.* 43:3474-3477, American Chemical Society (2000).

Takahara, A., et al., "Neuronal $Ca^{2+}$ Channel Blocking Action of an Antihypertensive Drug, Cilnidipine, in IMR-32 Human Neuroblastoma Cells," *Hypertens Res.* 26:743-747, Research Publishing House (Sep. 2003).

Tsien, R.Y., "New Calcium Indicators and Buffers with High Selectivity against Magnesium and Protons: Design, Synthesis, and Properties of Prototype Structures," *Biochemistry* 19:2396-2404, American Chemical Society (1980).

Vanegas, H., and Schaible, H.-G., " Effects of antagonists to high-threshold calcium channels upon spinal mechanisms of pain, hyperalgesia and allodynia," *Pain* 85:9-18, Elsevier Science B.V. (2000).

Vasudevan, A., et al., "Identification of aminopiperidine benzamides as MCHrl antagonists," *Bioorg. Med. Chem. Letts.* 15:3412-3416, Elsevier Ltd. (Jun. 2005).

Wallace, M.S., "Calcium and Sodium Channel Antagonists for the Treatment of Pain," *Clin. J. Pain* 16:S80-S85, Lippincott Williams & Wilkins, Inc. (2000).

Wu, C.-F., et al., "Dissociated Neurons From Normal and Mutant *Drosophila* Larval Central Nervous System In Cell Culture," *J. Neurosci.* 3:1888-1899, Society of Neuroscience (1983).

Xia, M., et al., "State-dependent inhibition of L-type calcium channels: cell-based assay in high-throughput format," *Anal. Biochem.* 327:74-81, Elsevier Inc. (Apr. 2004).

International Search Report for International Application No. PCT/EP2005/011105, European Patent Office, Netherlands, mailed on Sep. 7, 2006.

Brower, V., "New paths to pain relief," *Nat. Biotechnol.* 18:387-391, Nature America Publishing, United States (2000).

Dialog File 351, Accession No. 15133660, Derwent WPI English language abstract for JP 2005/179351 A, accessed on Jun. 30, 2008.

"Alzheimer's disease," Aetna InteliHealth, accessed at: http://www.inteliheatlh.com/IH/ihtlH/WSIHW000/8303/9117/195703.html?d=dmtHealthAZ, accessed on Jul. 1, 2008, 4 Pages.

Bingham, A.L., et al., "Over one hundred solvates of sulfathiazole," *Chem. Commun.* 2001:603-604, The Royal Society of Chemistry, England (2001).

Bleicher, K.H., et al., "Parallel Solotion- and Solid-Phase Synthesis of Spiropyrrolo-Pyrroles as Novel Neurokinin Receptor Ligands," *Bioorg. Med. Chem. Lett.* 12:3073-3076, Elsevier Science Ltd., England (2002).

Bobich, J.A., et al., "Incubation of nerve endings with a physiological concentration of $Aβ_{1-42}$ activates CaV2.2(N-Type)-voltage operated calcium channels and acutely increases glutamate and noradrenaline release," *J. Alzheimer's Dis.* 6:243-255, IOS Press, Netherlands (2004).

Bundgaard, H., "Means to Enhance Penetration: Prodrugs as a means to improve the delivery of peptide drugs," *Adv. Drug Deliv. Rev.* 8:1-38, Elsevier Science Publishers, B.V., Netherlands (1992).

Caira, M.R., et al., "Preparation and Crystal Characterization of a Polymorph, a Monohydrate, and an Ethyl Acetate Solvate of the Antifungal Fluconazole," *J. Pharm. Sci.* 93:601-611, Wiley-Liss, Inc. and the American Pharmacists Association, United States (2004).

Castellano, A., et al., "Cloning and Expression of a Neuronal Calcium Channel β Subunit," *J. Biol. Chem.* 268:12359-12366, The American Society for Biochemistry and Molecular Biology, Inc., United States (1993).

Catterall, W.A. et al., "International Union of Pharmacology. XLVIII. Nomenclature and Structure-Function Relationships of Voltage-Gated Calcium Channels," *Pharmacol, Rev.* 57:411-425, The American Society for Pharmacology and Experimental Therapeutics, United States (2005).

Filer, C.N., "The Preparation and Characterization of Tritiated Neurochemicals," in *Isotopes in the Physical and Biomedical Sciences.* vol. 1 *Labelled Compounds (Part A)*, Buncel, E. and Jones, J.R., eds., p. 156-192, Elsevier Science Publishers B.V., Netherlands (1987).

Grigg, R. and Coulter, T., "Sequential 1,3-Dipoloar Cycloaddition-Palladium Catalysed Cyclisation. A Powerful New Tactical Combination.," *Tetrahedron Lett.* 32:1359-1362, Pergamon Press plc., England (1991).

Grinvald, A., et al., "Improved Fluorescent Probes For The Measurement of Rapid Changes In Membrane Potential," *Biophys. J.* 39:301-308, Biophysical Society, United States (1982).

Hanson, G.R., "Analgesic, Antipyretic and Anti-inflammatory Drugs," in *Remington: The Science and Practice of Pharmacy*. vol. II, 19th Edition, pp. 1196-1221, Gennaro, A., ed., Lippincott Williams & Wilkins, United States (1995).

Insel, P.A., "Analgesic-Antipyretic and Antiinflammatory Agents and Drugs Employed in the Treatment of Gout," in *Goodman & Gilman's The Pharmacological Basis of Therapeutics*, 9th Edition, p. 617-657, Hardman, J.G., et al., eds., The McGraw-Hill Companies, Inc., United States (1996).

Kakeya, N., et al., "Studies on Prodrugs of Cephalosporins. I Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid," *Chem. Pharm. Bull.* 32:692-698, Pharmaceutical Society of Japan, Japan (1984).

(56) References Cited

OTHER PUBLICATIONS

Karikomi, M., et al., "A novel synthesis of 3-aminoazetidines by ring transformation of 2-(bromomethyl)aziridines," *Tetrahedron Lett.* 41:10295-10298, Elsevier Science Ltd., Netherlands (2000).

Khosravani, H. and Zamponi, G.W., "Voltage-Gated Calcium Channels and Idiopathic Generalized Epilepsies," *Physiol. Rev.* 86:941-966, the American Physiological Society, United States (2006).

Levine, J. and Taiwo, Y., "Inflammatory pain," in *Textbook of Pain*, 3rd Edition, pp. 45-56, Wall, P.D. and Melzack, R., eds., Churchill Livingstone, United Kingdom (1994).

Marecek, J.F. and Burrows, C.J., "Synthesis of an Optically Active Spermine Macrocycle, (S)-6-(Hydroxymethyl)-1,5,10,14-Tetraazacyclooctadecane, and Its Complexation to ATP," *Tetrahedron Lett.* 27:5943-5946, Pergamon Journals Ltd., Great Britain (1986).

Martin, Y.C., et al., "Do Structurally Similar Molecules Have Similar Biological Activity?" *J. Med. Chem.* 45:4350-4358, American Chemical Society, United States (2002).

Murakami, M., et al., "Modified sympathetic regulation in N-type calcium channel null-mouse," *Biochem. Biophys. Res. Comm.* 354:1016-1020, Elsevier Inc., United States (2007).

Nielsen, N.M. and Bundgaard, H., "Glycolamide Esters as Biolabile Prodrugs of Carboxylic Acid Agents: Synthesis, Stability, Bioconversion, and Physicochemical Properties," *J. Pharm. Sci.* 77(4):285-298, the American Pharmaceutical Association, United States (1988).

Piró, J., et al., "Asymmetric synthesis of β-pseudopeptides from chiral 3,4-aziridinolactams," *Tetrahedron Asymmetry* 13:995-1004, Elsevier Science Ltd., England (2002).

Russell, M.G.N., et al., "3-[3-(Piperidin-1-yl)propyl]indoles as Highly Selective h5-$HT_{1D}$ Receptor Agonists," *J. Med. Chem.* 42:4981-5001, American Chemical Society, United States (1999).

Sasikumar, T.K., et al., "Tetrahydroisoquinolines as MCH-R1 antagonists," *Bioorg. Med. Chem. Lett.* 16:4917-4921, Elsevier Ltd., England (2006).

Sindelar, K., et al., "Neurotropic and Psychotropic Agents. LXVII. 1-[4,4-Bis(4-Fluorophenyl)Butyl]-4-Hydroxy-4-(3-Triflouro-Methyl-4-Chlorophenyl)Piperidine and Related Compounds: New Synthetic Approaches," *Collect. Czeckoslov. Chem. Commun.* 38:3879-3901, Nakladatelstvi Ceskoslovenski Akademie Ved, Czech Republic (1973).

Stein, C., et al., "Unilateral Inflammation of the Hindpaw in Rats as a Model of Prolonged Noxious Stimulation: Alterations in Behavior and Nociceptive Thresholds," *Pharmacol. Biochem. Behav.* 31:445-451, Pergamon Press plc., United States (1988).

Teodori, E., et al., "Design, Synthesis, and Preliminary Pharmacological Evaluation of 4-Aminopiperidine Derivatives as N-Type Calcium Channel Blockers Active on Pain and Neuropathic Pain," *J. Med. Chem.* 47:6070-6081, American Chemical Society, United States (2004).

Tomiyama, H., et al., "Cilnidipine More Highly Attenuates Cold Pressor Stress-Induced Platelet Activation in Hypertension than Does Amlodipine," *Hypertens. Res.* 24:679-684, The Society, England (2001).

van de Waterbeemd, H., et al., "Property-Based Design: Optimization of Drug Absorption and Pharmacokinetics,", *J. Med. Chem.* 44:1313-1333, American Chemical Society, United States (2001).

van Tonder, E.C., et al., "Preparation and Physicochemical Characterization of 5 Niclosamide Solvates and 1 Hemisolvate," *AAPS PharmSciTech* 5:Article 12, American Association of Pharmaceutical Scientists, United States (2004).

Vippagunta, S.R., et al., "Crystalline solids," *Adv. Drug Deliv. Rev.* 48:.3-26, Elsevier Science B.V., Netherlands (2001)

Williams, J.A., et al., "Ziconotide: an update and review," *Expert Opin. Pharmacother.* 9:1575-1583, Informa UK Ltd, United Kingdom (2008).

Wu, K.-M. and Farrelly, J.G., "Regulatory perspectives of Type II prodrug development and time-dependent toxicity management: Nonclinical Pharm/Tox analysis and the role of comparative toxicology," *Toxicology* 236:1-6, Elsevier Ireland Ltd., Ireland (2007).

Yamamoto, T., et al., "Discovery, structure-activity relationship study, and oral analgesic efficacy of cyproheptadine derivatives possessing N-type calcium channel inhibitory activity," *Bioorg. Med. Chem.* 14:5333-5339, Elsevier Ltd., England (2006).

Youngman, M.A., et al., "α-Substituted *N*-(Sulfonamido)alkyl-β-aminotetralins: Potent and Selective Neuropeptide Y Y5 Receptor Antagonists," *J. Med. Chem.* 43:346-350, American Chemical Society, United States (2000).

English language Abstract of Japanes Patent Publication No. JP 5-201971 A, European Patent Office, espacenet database—Worldwide (2001), 1 page.

English language Abstract of International Patent Publication No. WO 2004/083167 A1, European Patent Office, espacenet database—Worldwide (2004), 1 page.

English language Abstract of Japanese Patent Publication No. JP 2006-83133 A, European Patent Office, espacenet database—Worldwide (2006), 1 page.

English language Abstract of Japanese Patent Publication No. JP 2006-83137 A, European Patent Office, espacenet database—Worldwide (2006), 1 page.

English language Abstract of International Patent Publication No. WO 2007/052843 A1, European Patent Office, espacenet database—Worldwide (2007), 1 page.

File Chemcats Database, Accession No. 2013992854, "1-(2-Chlorobenzoyl)-4- [cyclopropyl (phenylsulfonyl) amino] piperidine," published May 3, 2004 (XP002450197), 8 pages.

File Chemcats Database, Accession No. 2019241436, "4-(Cycloprophyl(phenylsulfonyl) amino) -1- (1-(5-trifluoromethyl) pyridin-2-yl) piperidine-4-yl)carbonyl)piperidine," published Sep. 13, 2006 (XP002450198), 4 pages.

International Preliminary Report on Patentability and Written Opinion of the International Searching Authority for International Application No. PCT/EP2005/011105, The International Bureau of WIPO, Geneva, Switzerland, issued on Apr. 17, 2007, 6 pages.

International Search Report for International Patent Application No. PCT/EP2007/053053, European Patent Office, Rijswijk, Netherlands, mailed on Jul. 19, 2007, 6 pages.

International Search Report for International Patent Application No. PCT/EP2007/053620, European Patent Office, Rijswijk, Netherlands, mailed on Aug. 7, 2007, 4 Pages.

International Search Report for International Application No. PCT/EP2007/053622, European Patent Office, Rijswijk, Netherlands, mailed on Oct. 1, 2007, 4 pages.

International Preliminary Report on Patentability and Written Opinion of the International Searching Authority for International Application No. PCT/EP2007/053053, European Patent Office, Rijswijk, Netherlands, issued on Jun. 20, 2008, 94 pages.

International Search Report for International Application No. PCT/US2008/004490, European Patent Office, Rijswijk, Netherlands, mailed on Aug. 5, 2008, 4 pages.

International Preliminary Report on Patentability and Written Opinion of the International Searching Authority for International Application No. PCT/EP2007/053620, The International Bureau of WIPO, Geneva, Switzerland, issued on Oct. 14, 2008, 9 pages.

International Preliminary Report on Patentability and Written Opinion of the International Searching Authority for International Application No. PCT/EP2007/053622, The International Bureau of WIPO, Geneva, Switzerland, issued on Oct. 14, 2008, 7 pages.

International Search Report for International Patent Application No. PCT/IB2008/002575, European Patent Office, Rijswijk, Netherlands, mailed on Sep. 29, 2009, 6 pages.

International Preliminary Report on Patentability and Written Opinion of the International Searching Authority for International Application No. PCT/US2008/004490, The International Bureau of WIPO, Geneva, Switzerland, issued on Oct. 13, 2009, 7 pages.

International Preliminary Report on Patentability and Written Opinion of the International Searching Authority for International Application No. PCT/IB2008/002575, The International Bureau of WIPO, Geneva, Switzerland, issued on Mar. 30, 2010, 11 pages.

Office action mailed on Jul. 16, 2010, in U.S. Appl. No. 12/296,799, Chen et al., having a 35 U.S.C. § 371 (c) date of Jan. 30, 2009.

Office action mailed on Mar. 29, 2011, in U.S. Appl. No. 12/296,799, Chen et al., having a 35 U.S.C. § 371 (c) date of Jan. 30, 2009.

(56) References Cited

OTHER PUBLICATIONS

Office Action mailed on Mar. 30, 2011, in U.S. Appl. No. 12/296,788, Matsumura et al., having a 35 U.S.C. § 371 (c) date of Oct. 10, 2008.
Office Action mailed on Aug. 23, 2011, in U.S. Appl. No. 12/225,743, Chen et al., having a 35 U.S.C. § 371 (c) date of Mar. 26, 2009.
Office Action mailed on Dec. 13, 2011, in U.S. Appl. No. 12/225,743, Chen et al., having a 35 U.S.C. § 371 (c) date of Mar. 26, 2009.
STNEasy Database, Accession No. 2007:510466, English language abstract for Miura, S., et al., "Preparation of heterocyclic amide compounds as FXR inhibitors," WIPO Patent Publication No. WO 2007/052843 A1 (XP002444167), 3 pages.
Unverified English language abstract for Japanese Patent Publication No. JP 2005/154380 A, espacenet Database, European Patent Office, 2 pages (2005).
Kehlet, H., et al., "Persistent postsurgical pain: risk factors and prevention," *Lancet* 367:1618-1625, Lancet Publishing Group, England (2006).
McGivern, J.G., "Ziconotide: a review of its pharmacology and use in the treatment of pain," *Neuropsychiatric Disease and Treatment* 3(1):69-85, Dove Medical Press Limited, United States (Feb. 2007).
Melemeni, A., et al., "Gabapentin for acute and chronic post-surgical pain," *Signa Vitae 2 Suppl* 1:42-51, Pharmamed Mado Ltd., Croatia (May 2007).
Montazeri, K., et al., "Pre-emptive gabapentin significantly reduces postoperative pain and morphine demand following lower extremity orthopaedic surgery," *Singapore Med. J.*, 48(8):748-751, Singapore Medical Assn., Signapore (Aug. 2007).
Triggle, D.J., "Calcium channel antagonist: Clinical uses—Past, present and future," *Biochemical Pharmacology* 74:1-9, Elsevier Inc., England (Jun. 2007; Epub. Jan. 2007).
Notice of Allowance mailed Mar. 30, 2012, in U.S. Appl. No. 12/225,743, Chen et al., having a 35 U.S.C. § 371 (c) dated of Mar. 26, 2009.
Office Action mailed Jan. 3, 2012, in U.S. Appl. No. 12/296,788, Matsummura et al., having a 35 U.S.C. § 371 (c) date of Oct. 10, 2008.
Office Action mailed Feb. 1, 2012, in U.S. Appl. No. 12/595,066, Kyle et al., having a 35 U.S.C. § 371 (c) dated of Oct. 8, 2009.
Office Action mailed Jul. 5, 2012, in U.S. Appl. No. 12/595,066, Kyle et al., having a 35 U.S.C. § 371 (c) dated of Oct. 8, 2009.
Office Action mailed Jul. 12, 2012, in U.S. Appl. No. 12/599,608, Shao et al., having a 35 U.S.C. § 371 (c) date of Nov. 10, 2009.

\* cited by examiner

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
caccatggtc cgcttcgggg ac                                          22

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
ccgttcagtg gcctcctcc                                              19

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer

<400> SEQUENCE: 3
ctagcaccag tgatcctggt ctg                                         23

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
agtgcgttgt gagcgcagta                                             20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
caccatggtc cagaagagcg g                                           21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

```
<400> SEQUENCE: 6
tctcagcgga tgtagacgcc t                                              21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
caccatgtat gacgactcct ac                                             22

<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ggtggtcagt agctgtcctt agg                                            23

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
caccatggct gctggctgcc t                                              21

<210> SEQ ID NO 10
<211> LENGTH: 25
<212> TYPE: DNA
<213> ORGANISM: Artificial Sequence
<220> FEATURE:
<223> OTHER INFORMATION: Synthetic Primer

<400> SEQUENCE: 10
agagggtcac catagatagt gtctg                                          25

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
caccatgatt cgggccttcg ct                                             22

<210> SEQ ID NO 12
<211> LENGTH: 25
<212> TYPE: DNA
<213> ORGANISM: Artificial Sequence
<220> FEATURE:
<223> OTHER INFORMATION: Synthetic Primer

<400> SEQUENCE: 12
agcctgcgga ctacaggttg ctgac                                          25
```

4-PHENYLSULFONAMIDOPIPERIDINES AS CALCIUM CHANNEL BLOCKERS

BACKGROUND OF THE INVENTION

1. Field of the Invention

This invention is in the field of medicinal chemistry. The invention relates to novel piperidinyl compounds and the discovery that these compounds act as blockers of calcium ($Ca^{2+}$) channels. In particular, the invention relates to a high-throughput screening assay useful for identifying such compounds.

2. Background Art

Calcium ions play fundamental roles in the regulation of many cellular processes. It is therefore essential that their intracellular levels be maintained under strict, yet dynamic control (Davila, H. M., *Annals of the New York Academy of Sciences*, pp. 102-117 (1999)). Voltage-gated calcium channels (VGCC) serve as one of the important mechanisms for fast calcium influx into the cell. Calcium channels are hetero-oligomeric proteins consisting of a pore-forming subunit ($\alpha 1$), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) R-type channels; and (iii) low voltage-activated (LVA) T-type channels (Davila, supra). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (Hu et al, *Bioorganic & Medicinal Chemistry* 8:1203-1212 (2000)). N-type channels are found mainly in central and peripheral neurons, being primarily located on presynaptic nerve terminals. These channels regulate the calcium flux required for depolarization-evoked release of a transmitter from synaptic endings. The transmission of pain signals from periphery to the central nervous system (CNS) is mediated by N-type calcium channels located in the spinal cord (Song et al., *J. Med. Chem.* 43:3474-3477 (2000)).

The six types of calcium channels (i.e., L, N, P, Q, R, and T) are expressed throughout the nervous system (Wallace, M. S., *The Clinical Journal of Pain* 16:580-585 (2000)). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (supra) suggests that based on animal models, N-type calcium channel antagonists have a greater analgesic potency than sodium channel antagonists.

N-type calcium channel blockers have usefulness for neuroprotection and analgesia. Ziconotide, which is a selective N-type calcium channel blocker, has been found to have analgesic activity in animal models and neuroprotective activity in focal and global ischemia models (Song et al., supra). Examples of known calcium channel blockers include flunarizine, fluspirilene, cilnipide, PD 157767, SB-201823, SB-206284, NNC09-0026, and PD 151307 (Hu et al, supra).

Blockade of N-type channels can prevent and/or attenuate subjective pain as well as primary and/or secondary hyperalgesia and allodynia in a variety of experimental and clinical conditions (Vanegas, H. et al, *Pain* 85:9-18 (2000)). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (Song et al., supra). Inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

Movement of physiologically relevant substrates through ion channels can be traced by a variety of physical, optical, or chemical techniques (Stein, W. D., *Transport and Diffusion Across Cell Membranes*, 1986, Academic Press, Orlando, Fla.). Assays for modulators of ion channels include electrophysiological assays, cell-by-cell assays using microelectrodes (Wu, C.-F., Suzuki, N., and Poo, M. M. *J. Neurosci* 3(9):1888-99 (1983)), i.e., intracellular and patch clamp techniques (Neher, E. and Sakmann, B., *Sci. Amer.* 266:44-51 (1992)), and radioactive tracer ion techniques. The patch clamp and whole cell voltage clamp, current clamp, and two-electrode voltage clamp techniques require a high degree of spatial precision when placing the electrodes. Functional assays can be conducted to measure whole-cell currents with the patch clamp technique. However, the throughput is very limited in number of assays per day.

Radiotracer ions have been used for biochemical and pharmacological investigations of channel-controlled ion translocation in cell preparations (Hosford, D. A. et al, *Brain Res.* 516:192-200 (1990)). In this method, the cells are exposed to a radioactive tracer ion and an activating ligand for a period of time, the cells are then washed, and counted for radioactive content. Radioactive isotopes are well known (Evans, E. A., Muramtsu, M. *Radiotracer Techniques and Applications*, M. Dekker, New York (1977)) and their uses have permitted detection of target substances with high sensitivity. However, radioactive isotopes require many safety precautions. The use of alternative and safer non-radioactive labeling agents has thus increased in recent years.

Optical methods using fluorescence detection are suitable alternatives to the patch-clamp and radioactive tracer techniques. Optical methods permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. et al., *Biophys. Acta* 988:319-334 (1989)). The general principle of monitoring transport by fluorescence is based on having compartment-dependent variations in fluorescence properties associated with translocation of compounds.

Optical detection of electrical activity in nerve cells is conducted using voltage-sensitive membrane dyes and arrays of photodetectors (Grinvald, A., *Annu. Rev. Neurosci.* 8:263-305 (1985); Loew, L. M., and Simpson, L. L., *Biopkys. J* 34:353-65 (1981); Grinvald, A. et al., *Biophys. J.* 39:301-08 (1983) and Grinvald, A. et al., *Biophys. J.* 42:195-98 (1983)). Optical methods have been developed for measuring calcium ion flux (Scarpa, A., *Methods of Enzymology* 56:301 (1979), Academic Press, Orlando, Fla.; Tsien, R. Y., *Biochemistry* 19:2396 (1980); Grynkiewicz, G. et al., *J. Biol. Chem.* 260: 3440 (1985)). The flux of calcium ions is typically monitored using calcium-sensitive fluorescent dyes, such as Fluo-3, Fluo-4, Calcium green, and others. (Molecular Probes Inc., Handbook of Fluorescent Probes and Research Chemicals, 7th ed., chapt 1, Eugene, Oreg.).

A need exists for novel assays that can identify compounds that modulate or block the movement of calcium ions through voltage-gated calcium channels, including N-type calcium channels.

BRIEF SUMMARY OF THE INVENTION

The present invention is related to the use of piperidinyl compounds represented by Formula I, below, as blockers of calcium ($Ca^{2+}$) channels. Specifically, it has been found that compounds of Formula I are selective N-type calcium channel blockers.

The invention is also related to treating, preventing or ameliorating a disorder responsive to the blockade of calcium channels in a mammal suffering from excess activity of said channels by administering an effective amount of a compound of Formula I as described herein. Specifically, the invention is related to treating, preventing or ameliorating a disorder responsive to the blockade of N-type calcium channels in a mammal suffering from excess activity of said channels by administering an effective amount of a compound of Formula I as described herein.

A number of compounds useful in the present invention have not been heretofore reported. Thus, one aspect of the present invention is directed to novel piperidinyl compounds of Formula I.

Another aspect of the present invention is directed to the use of the novel compounds of Formula I as blockers of N-type calcium channels.

An aspect of the present invention is directed to the novel compounds of Formula X, below, and pharmaceutical compositions thereof, and their use as blockers of calcium channels, and especially N-type calcium channels.

A further aspect of the present invention is to provide a method for treating, preventing or ameliorating stroke, head trauma, epilepsy, pain (e.g., acute pain, or chronic pain, which includes but is not limited to neuropathic pain and inflammatory pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound of Formula I to a mammal in need of such treatment, prevention or amelioration.

A further aspect of the present invention is to provide a pharmaceutical composition useful for treating, preventing or ameliorating a disorder responsive to the blockade of calcium ion channels, especially N-type calcium ion channels, said pharmaceutical composition containing an effective amount of a compound of Formula I in a mixture with one or more pharmaceutically acceptable carriers.

A further aspect of the present invention is to provide $^3H$ or $^{14}C$ radiolabeled compounds of Formula I or X and their use as radioligands for their binding site on the calcium channel.

The present invention is also related to a high-throughput assay for screening compounds to identify modulators or blockers of calcium ($Ca^{2+}$) channels. The assay of the present invention is preferably employed to screen for blockers of calcium channels. In one embodiment, the assay of the present invention is useful for screening compounds that block N-type calcium channels. The assay of the present invention is particularly suited for identifying compounds that bind to N-type calcium channels, which are in the inactive state.

The invention is also directed to the use of the novel compounds that are identified by the assay described herein as blockers of N-type calcium channels.

The invention is further related to treating, preventing or ameliorating a disorder responsive to the blockade of calcium channels in a mammal suffering from excess activity of said channels by administering an effective amount of a compound identified using the assay described herein.

Another aspect of the present invention is directed to compounds identified by the assay described herein as blockers of N-type calcium channels, and pharmaceutical compositions thereof, and the use of the pharmaceutical composition as blockers of calcium channels, and especially N-type calcium channels.

A further aspect of the present invention is to provide a method for treating, preventing or ameliorating stroke, head trauma, epilepsy, pain (e.g., acute pain, or chronic pain, which includes but is not limited to neuropathic pain and inflammatory pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound identified as a blocker of N-type calcium channels using the assay described herein to a mammal in need of such treatment, prevention or amelioration.

A further aspect of the present invention is to provide a pharmaceutical composition useful for treating, preventing or ameliorating a disorder responsive to the blockade of N-type calcium channels, said pharmaceutical composition containing an effective amount of a compound identified as a blocker of N-type calcium channels using the assay described herein in a mixture with one or more pharmaceutically acceptable carriers.

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DETAILED DESCRIPTION OF THE INVENTION

One aspect of the present invention is based on the discovery that piperidinyl compounds of Formula I act as blockers of $Ca^{2+}$ channels. In view of this discovery, compounds of Formula I are seen as useful for treating disorders responsive to the blockade of calcium ion channels. In one aspect, it has been found that compounds of Formula I selectively block N-type calcium ion channels and, thus, are useful for treating disorders responsive to the selective blockade of N-type calcium ion channels.

The compounds useful in this aspect of the invention are piperidinyl compounds represented by Formula I:

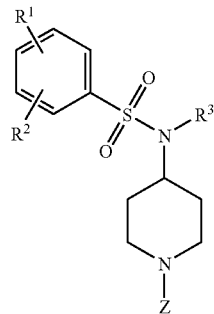

or a pharmaceutically acceptable salt, prodrug or solvate thereof, wherein:

$R^1$ and $R^2$ are each independently selected from the group consisting of hydrogen, alkyl, haloalkyl, halogen, alkoxy, haloalkoxy, cyano, nitro, amino, and hydroxy;

$R^3$ is selected from the group consisting of alkyl, alkenyl, cycloalkyl, cycloalkylalkyl, alkoxyalkyl, hydroxyalkyl, 2-tetrahydrofuranyl, 3-tetrahydrofuranyl, 2-tetrahydrofuranylalkyl, 3-tetrahydrofuranylalkyl, alkylsulfonylaminoalkyl, and aminocarbonylalkyl;

Z is selected from the group consisting of $Z^1$, $Z^2$, $Z^3$, and $Z^4$, wherein:

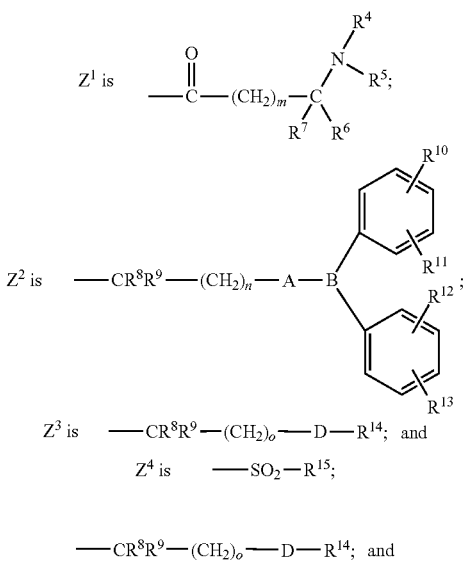

$Z^3$ is $$—CR^8R^9—(CH_2)_o—D—R^{14};\text{ and}$$

$R^4$ and $R^5$ are each independently selected from the group consisting of hydrogen, alkyl, alkenyl, hydroxyalkyl, haloalkyl, alkylthiol, aminoalkyl and phenyl; or $R^4$ and $R^5$ together with the nitrogen atom to which they are attached form a 5- or 6-membered heterocyclic ring wherein one or more carbon atoms of the heterocyclic ring are optionally replaced with $NR^{16}$, O, or S, wherein $R^{16}$ is hydrogen or $C_{1-3}$ alkyl;

$R^6$ is hydrogen and $R^7$ is selected from the group consisting of
hydrogen;
alkyl;
hydroxyalkyl;
alkoxyalkyl;
haloalkyl;
aminoalkyl;
cycloalkyl;
phenyl optionally substituted with one or two substituents independently selected from the group consisting of alkyl, cycloalkyl, halogen, cyano, amino, alkylamino, dialkylamino, hydroxy, nitro, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, haloalkyl, and alkoxy; and
benzyloxyalkyl; or $R^6$ and $R^7$ together with the carbon atom to which they are attached form a $C_{3-7}$ cycloalkyl group; or $R^7$ is hydrogen; $R^4$ is hydrogen or $C_{1-3}$ alkyl; and $R^5$ and $R^6$ together form a bridge $—CH_2—CH_2—CH_2—$ or $—CH_2—CHG^1-CHG^2-CH_2—$, wherein $G^1$ and $G^2$ are both hydrogen or together with the carbon atoms to which they are attached form a fused phenyl group;

$R^3$ and $R^9$ are both hydrogen or together form =O;

$R^{10}$, $R^{11}$, $R^{12}$ and $R^{13}$ are each independently selected from the group consisting of hydrogen, alkyl, alkoxy, halogen, haloalkyl, hydroxy, hydroxyalkyl, cyano, amino, aminoalkyl, alkylamino, and dialkylamino;

$R^{14}$ is selected from the group consisting of
phenyl optionally substituted with one or two substituents independently selected from the group consisting of alkyl, alkoxy, halogen, haloalkyl, hydroxy, hydroxyalkyl, cyano, amino, aminoalkyl, alkylamino, and dialkylamino;
naphthyl optionally substituted with one or two substituents independently selected from the group consisting of alkyl, alkoxy, halogen, haloalkyl, hydroxy, hydroxyalkyl, cyano, amino, aminoalkyl, alkylamino, and dialkylamino;
quinolinyl;
pyridyl;
phenyl substituted with phenyl, benzyl, phenoxy, or benzyloxy, wherein each phenyl ring is optionally substituted with one or two substituents independently selected from the group consisting of halogen, haloalkyl, alkyl, alkoxy, hydroxy, amino and cyano; and
alkyl, preferably n-propyl.

$R^{15}$ is phenyl or naphthyl, either of which is optionally substituted with one or two substituents independently selected from the group consisting of alkyl, alkoxy, halogen, haloalkyl, amino, alkylamino and dialkylamino;

A is O, $CH_2$, or absent (a covalent bond), and B is CH, provided that when A is O, then $R^8$ and $R^9$ are both hydrogen; or A-B is CH=C;

D is C=O, —CH=CH—, or absent (a covalent bond);

m is 0 or 1;

n is 0, 1, 2, 3, 4, or 5; and o is 0, 1, 2, or 3;

with the proviso that when Z is $Z^2$, $R^3$ is alkyl, $R^8$ and $R^9$ are both hydrogen, A is $CH_2$, B is CH and n is 1, then at least one of $R^{10}$, $R^{11}$, $R^{12}$, or $R^{13}$ is other than hydrogen.

In compounds of Formula I where Z is $Z^1$, the carbon to which the —$NR^4R^5$ group is attached can be a chiral center. Accordingly, the configuration at that carbon atom can be (R) or (S), with (S) being preferred.

Since the compounds of Formula I are blockers of calcium ($Ca^{2+}$) channels, a number of diseases and conditions mediated by calcium ion influx can be treated by employing these compounds. Therefore, the present invention provides a method of treating, preventing or ameliorating stroke, head trauma, epilepsy, pain (e.g., chronic pain, neuropathic pain, inflammatory pain, or acute pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In each instance, such methods of treatment, prevention, or amelioration require administering to an animal in need of such treatment, prevention or amelioration an effective amount of a calcium channel blocker of the present invention, or a pharmaceutically acceptable salt, prodrug or solvate thereof.

In one embodiment, compounds useful in the present invention are piperidinyl compounds represented by Formula II:

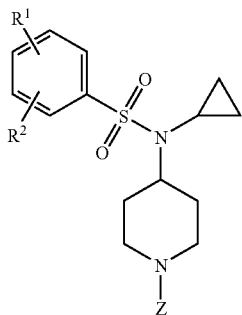

II or a pharmaceutically acceptable salt, prodrug, or solvate thereof, wherein $R^1$, $R^2$, and Z are as defined above.

In one aspect of the present invention, compounds useful in the present invention are piperidinyl compounds represented by Formula III:

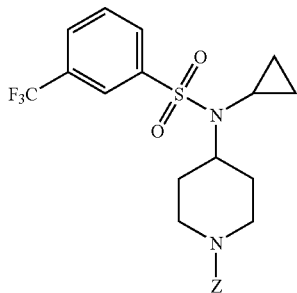

III or a pharmaceutically acceptable salt, prodrug, or solvate thereof, wherein Z is as defined above.

Preferably, in compounds of Formulae I and II, $R^1$ and $R^2$ are each independently selected from the group consisting of hydrogen, halogen, alkyl, haloalkyl, cyano, alkoxy, haloalkoxy, and nitro. More preferably, $R^1$ and $R^2$ are each independently selected from the group consisting of hydrogen, halogen, $C_{1-6}$ alkyl, halo($C_{1-6}$)alkyl, cyano, $C_{1-6}$ alkoxy, halo($C_{1-6}$)alkoxy, and nitro; and more preferably independently selected from the group consisting of hydrogen, halogen, $C_{1-3}$ alkyl, halo($C_{1-3}$)alkyl, cyano, $C_{1-3}$ alkoxy, halo($C_{1-3}$)alkoxy, and nitro. Advantageously, $R^1$ and $R^2$ are independently hydrogen, methyl, ethyl, fluoro, chloro, trifluoromethyl, difluoromethyl, fluoromethyl, cyano, nitro, methoxy or difluoromethoxy. More preferably, $R^1$ is hydrogen and $R^2$ is trifluoromethyl, or both $R^1$ and $R^2$ are hydrogen. Preferably, $R^2$ is in the meta-position of the phenyl ring.

Preferably, $R^3$ is selected from the group consisting of alkyl, cycloalkyl, cycloalkylalkyl, 3-tetrahydrofuranyl, 2-tetrahydrofuranylalkyl, alkoxyalkyl, hydroxyalkyl, alkylsulfonylaminoalkyl and aminocarbonylalkyl; more preferably selected from $C_{1-6}$ alkyl, $C_{3-6}$ cycloalkyl, 3-tetrahydrofuranyl, 2-tetrahydrofuranyl($C_{1-3}$)alkyl, $C_{3-6}$ cycloalkyl($C_{1-3}$)alkyl, $C_{1-3}$ alkoxy($C_{1-6}$)alkyl, hydroxy($C_{1-6}$)alkyl, $C_{1-3}$ alkylsulfonylamino($C_{1-3}$)alkyl, and aminocarbonyl($C_{1-3}$)alkyl. Advantageously, $R^3$ is selected from the group consisting of methyl, ethyl, iso-pentyl, iso-butyl, iso-propyl, cyclopropyl, cyclobutyl, cyclopentyl, cyclopropylmethyl, cyclopropylethyl, methoxymethyl, methoxyethyl, hydroxymethyl, hydroxyethyl, 3-tetrahydrofuranyl, 2-tetrahydrofuranylmethyl, 2-tetrahydrofuranylethyl, methylsulfonamidomethyl, methylsulfonamidoethyl, aminocarbonylmethyl, and aminocarbonylethyl. More advantageously, $R^3$ is cyclopropyl, methyl, iso-propyl, or iso-butyl, especially cyclopropyl.

In compounds of Formulae I-III, $R^4$ and $R^5$ are preferably each independently selected from the group consisting of hydrogen, alkyl, hydroxyalkyl, and phenyl; more preferably independently selected from hydrogen, $C_{1-6}$ alkyl, hydroxy($C_{1-6}$)alkyl, and phenyl; more preferably independently selected from hydrogen, $C_{1-3}$ alkyl, hydroxy($C_{1-3}$)alkyl, and phenyl; and more preferably independently selected from hydrogen, methyl, ethyl, hydroxymethyl, hydroxyethyl, and phenyl; or $R^4$ and $R^5$ together with the nitrogen atom to which they are attached form a 5- or 6-membered heterocyclic ring selected from the group consisting of oxazolidinyl, isoxazolidinyl, pyrrolidinyl, pyrazolidinyl, imidazolidinyl, hexahydropyrimidinyl, piperidinyl, piperazinyl, 4-methylpiperazinyl, morpholinyl, thiomorpholinyl, and tetrahydropyridyl. Advantageously, $R^4$ and $R^5$ are independently hydrogen, methyl or hydroxyethyl, or $R^4$ and $R^5$ together with the nitrogen atom to which they are attached form 1-pyrrolidinyl, 4-thiomorpholinyl, piperazinyl, or 4-methylpiperazinyl.

When $R^6$ is hydrogen, $R^7$ is preferably selected from the group consisting of alkyl; hydroxyalkyl; cycloalkyl; phenyl optionally substituted with one or two substituents independently selected from the group consisting of alkyl, cycloalkyl, halogen, cyano, amino, alkylamino, dialkylamino, hydroxy, nitro, haloalkyl, and alkoxy; benzyl optionally substituted with one or two substituents independently selected from the group consisting of alkyl, cycloalkyl, halogen, cyano, amino, alkylamino, dialkylamino, hydroxy, nitro, haloalkyl, and alkoxy; and benzyloxyalkyl. More preferably, $R^7$ is selected from the group consisting of straight chain $C_{1-6}$ alkyl; branched chain $C_{3-6}$ alkyl; hydroxy($C_{1-6}$)alkyl; $C_{3-6}$ cycloalkyl; phenyl optionally substituted with one or two substituents independently selected from the group consisting of $C_{1-6}$ alkyl, $C_{3-6}$ cycloalkyl, halogen, cyano, amino, $C_{1-3}$ alkylamino, di($C_{1-3}$)alkylamino, hydroxy, nitro, halo($C_{1-6}$)alkyl, and $C_{1-6}$ alkoxy; benzyl optionally substituted with one or two substituents independently selected from the group consisting of $C_{1-6}$ alkyl, $C_{3-6}$ cycloalkyl, halogen, cyano, amino, $C_{1-3}$ alkylamino, di($C_{1-3}$)alkylamino, hydroxy, nitro, halo($C_{1-6}$)alkyl, and $C_{1-6}$ alkoxy; and benzyloxy($C_{1-3}$)alkyl. Advantageously, $R^7$ is methyl; propyl; iso-propyl; butyl; tert-butyl; sec-butyl; iso-butyl; hydroxymethyl; 1-hydroxyethyl; phenyl optionally substituted with one or two substituents independently selected from the group consisting of methyl ethyl, propyl, iso-propyl, butyl, tert-butyl, halogen, cyano, amino, methylamino, dimethylamino, hydroxy, nitro, and trifluoromethyl; benzyl optionally substituted with one or two substituents independently selected from the group consisting of methyl ethyl, propyl, iso-propyl, butyl, tert-butyl, halogen, cyano, amino, methylamino, dimethylamino, hydroxy, nitro, and trifluoromethyl; 1-benzyloxyethyl; cyclopentyl; cyclohexyl; cyclopentylmethyl; or cyclohexylmethyl.

In one preferred aspect, when $R^6$ is hydrogen and $R^7$ is alkyl, $R^4$ and $R^5$ together form a 5- or 6-membered heterocycle as described above, or $R^4$ and $R^5$ are independently hydrogen, alkyl, or hydroxyalkyl.

Useful compounds include those where $R^6$ and $R^7$ together with the carbon atom to which they are attached form a $C_{3-6}$ cycloalkyl group, which is preferably cyclopentyl or cyclohexyl.

Useful compounds include those where $R^7$ is hydrogen, $R^4$ is hydrogen, methyl or ethyl, and $R^5$ and $R^6$ together form a bridge —$CH_2$—$CH_2$—$CH_2$— or —$CH_2$—$CHG^1$-$CHG^2$-$CH_2$—, wherein $G^1$ and $G^2$ are both hydrogen or together with the carbon atoms to which they are attached form a fused phenyl group. Advantageously, $R^5$ and $R^6$ together form —$CH_2$—$CH_2$—$CH_2$—.

Useful compounds include those where $R^8$ and $R^9$ are both hydrogen when Z is $Z^2$, A is $CH_2$ or absent and B is CH. Other useful compounds include those where $R^8$ and $R^9$ form =O when Z is $Z^2$, A is $CH_2$ or absent and B is CH, or A-B is CH=C. Additional useful compounds include those where Z is $Z^2$, $R^8$ and $R^9$ are both hydrogen and A is O.

Preferably, $R^{10}$, $R^{11}$, $R^2$, and $R^{13}$ are each independently selected from the group consisting of hydrogen, halogen, $C_{1-6}$ alkyl, $C_{1-6}$ alkoxy, halogen, halo($C_{1-6}$)alkyl, hydroxy, hydroxy($C_{1-6}$)alkyl, cyano, amino, amino($C_{1-6}$)alkyl, $C_{1-3}$ alkylamino, and di($C_{1-3}$)alkylamino. More preferably, $R^{10}$, $R^{11}$, $R^{12}$, and $R^{13}$ are each independently selected from the group consisting of hydrogen, halogen, $C_{1-4}$ alkyl, $C_{1-3}$ alkoxy, halo, halo($C_{1-3}$)alkyl, cyano, amino, amino ($C_{1-3}$) alkyl, $C_{1-3}$ alkylamino, and di($C_{1-3}$)alkylamino. Advantageously, $R^{10}$, $R^{11}$, $R^{12}$, and $R^{13}$ are each independently selected from the group consisting of hydrogen, halogen, methyl, ethyl, methoxy, ethoxy, trifluoromethyl, cyano, amino, methylamino, and dimethylamino, and especially halogen. Preferably, $R^{10}$ and $R^{12}$ are both hydrogen. Preferably, either or both $R^{11}$ and $R^{13}$ are at the para-position of their respective phenyl rings.

Preferably, $R^{14}$ is selected from the group consisting of phenyl optionally substituted with one or two substituents independently selected from the group consisting of alkyl, alkoxy, halogen, haloalkyl, hydroxy, hydroxyalkyl, cyano, amino, aminoalkyl, alkylamino, and dialkylamino; phenyl substituted with phenyl, benzyl, phenoxy or benzyloxy, wherein each phenyl ring is optionally substituted with one or two substituents selected from the group consisting of halogen, haloalkyl, alkyl, alkoxy, hydroxy, amino, and cyano; naphthyl; quinolinyl; and pyridyl.

Useful compounds include those where $R^{14}$ is phenyl optionally substituted with one or two substituents independently selected from the group consisting of alkyl, alkoxy, halogen, haloalkyl, hydroxy, hydroxyalkyl, cyano, amino, aminoalkyl, alkylamino, and dialkylamino; preferably independently selected from the group consisting of alkyl, alkoxy, halo, haloalkyl, hydroxy, cyano, alkylamino, and dialkylamino; and more preferably independently selected from the group consisting of $C_{1-6}$ alkyl, $C_{1-6}$ alkoxy, halo, halo($C_{1-3}$) alkyl, hydroxy, cyano, $C_{1-3}$ alkylamino, and di($C_{1-3}$)alkylamino. Advantageously, $R^{14}$ is a phenyl group substituted with one or two substituents independently selected from the group consisting of methyl, ethyl, iso-propyl, tert-butyl, methoxy, ethoxy, fluoro, trifluoromethyl, methylamino, and dimethylamino.

Useful compounds include those where $R^{14}$ is phenyl substituted, preferably at the para-position, with phenyl, benzyl, phenoxy or benzyloxy any of which are unsubstituted or substituted with halogen, haloalkyl, alkyl, alkoxy, hydroxy, amino, or cyano, and preferably substituted with halogen.

Useful compounds also include those where $R^{14}$ is naphthyl, quinolinyl or pyridyl, any of which are unsubstituted.

Useful compounds also include those where $R^8$ and $R^9$ together form =O, o is 0, D is —CH=CH— and $R^{14}$ is n-propyl.

Preferably, $R^8$ and $R^9$ are both hydrogen when $R^{14}$ is one of naphthyl;
quinolinyl;
pyridyl;
phenyl substituted with phenyl optionally substituted with halogen, haloalkyl, alkyl, alkoxy, hydroxy, amino, or cyano;
phenyl substituted with benzyl optionally substituted with halogen, haloalkyl, alkyl, alkoxy, hydroxy, amino, or cyano;
phenyl substituted with phenoxy optionally substituted with halogen, haloalkyl, alkyl, alkoxy, hydroxy, amino, or cyano; or
phenyl substituted with benzyloxy optionally substituted with halogen, haloalkyl, alkyl, alkoxy, hydroxy, amino, or cyano.

Preferably, $R^{15}$ is phenyl substituted with one or two substituents independently selected from the group consisting of alkyl, alkoxy, halogen, haloalkyl, amino, alkylamino and dialkylamino. Useful compounds include those where $R^{15}$ is phenyl substituted with $C_{1-6}$ alkyl, $C_{1-6}$ alkoxy, halogen, halo ($C_{1-3}$)alkyl, amino, $C_{1-3}$ alkylamino or di($C_{1-3}$)alkylamino; and more preferably substituted with propyl, butyl, pentyl, propoxy, butoxy, pentoxy, fluoro, chloro, trifluoromethyl, amino, methylamino or dimethylamino. Useful compounds also include those where $R^{15}$ is naphthyl substituted with amino, alkylamino or dialkylamino; preferably substituted with amino, $C_{1-3}$ alkylamino or di($C_{1-3}$)alkylamino; and more preferably substituted with amino, methylamino or dimethylamino.

Useful compounds include those where $R^8$ and $R^9$ are both hydrogen or together form =O and D is absent or —CH=CH—. Useful compounds include those where $R^8$ and $R^9$ form =O and D is C=O.

Preferably, n is 0, 1 or 2.
Preferably, o is 0, 1 or 2.
The invention also relates to piperidinyl compounds represented by Formula IV:

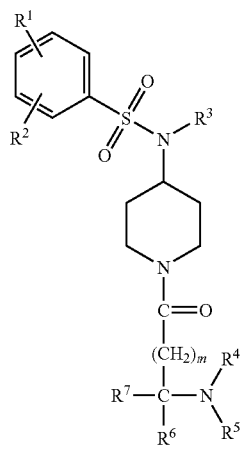

IV or a pharmaceutically acceptable salt, prodrug or solvate thereof, wherein:
$R^1$ and $R^2$ are each independently selected from the group consisting of hydrogen, alkyl, haloalkyl, halogen, alkoxy, haloalkoxy, cyano, nitro, amino, and hydroxy;

$R^3$ is selected from the group consisting of alkyl, alkenyl, cycloalkyl, cycloalkylalkyl, alkoxyalkyl, hydroxyalkyl, 2-tetrahydrofuranyl, 3-tetrahydrofuranyl, 2-tetrahydrofuranylalkyl, 3-tetrahydrofuranylalkyl, alkylsulfonylaminoalkyl, and aminocarbonylalkyl;

$R^4$ and $R^5$ are each independently selected from the group consisting of hydrogen, alkyl, alkenyl, hydroxyalkyl, haloalkyl, alkylthiol, aminoalkyl and phenyl; or $R^4$ and $R^5$ together with the nitrogen atom to which they are attached form a 5- or 6-membered heterocyclic ring wherein one or more carbon atoms of the heterocyclic ring are optionally replaced with $NR^{16}$, O, or S, wherein $R^{16}$ is hydrogen or $C_{1-3}$ alkyl;

$R^6$ is hydrogen and $R^7$ is independently selected from the group consisting of
hydrogen;
alkyl;
hydroxyalkyl;
alkoxyalkyl;
haloalkyl;
aminoalkyl;
cycloalkyl;
phenyl optionally substituted with one or two substituents independently selected from the group consisting of alkyl, cycloalkyl, halo, cyano, amino, alkylamino, dialkylamino, hydroxy, nitro, haloalkyl, and alkoxy;
benzyl optionally substituted with one or two substituents independently selected from the group consisting of alkyl, cycloalkyl, halo, cyano, amino, alkylamino, dialkylamino, hydroxy, nitro, haloalkyl, and alkoxy; and
benzyloxyalkyl; or $R^6$ and $R^7$ together with the carbon atom to which they are attached form a $C_{3-7}$ cycloalkyl group; or $R^7$ is hydrogen, $R^4$ is hydrogen or $C_{1-3}$ alkyl, and $R^5$ and $R^6$ together form a bridge —$CH_2$—$CH_2$—$CH_2$— or —$CH_2$—$CHG^1$-$CHG^2$-$CH_2$—, wherein $G^1$ and $G^2$ are both hydrogen or together with the carbon atoms to which they are attached form a fused phenyl group; and m is 0 or 1.

Preferred values for $R^1$-$R^7$ and m are those described above for Formula I. In one aspect, preferred compounds falling within the scope of Formula IV include those represented by Formula V:

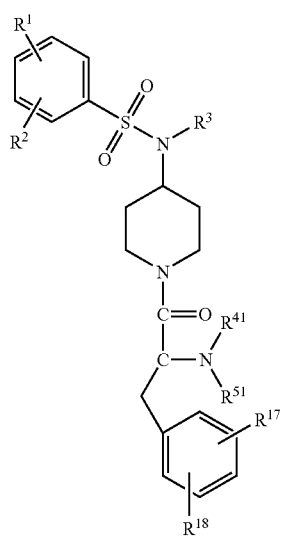

or a pharmaceutically acceptable salt, prodrug, or solvate thereof, wherein:

$R^1$-$R^3$ are as described for Formula IV;

$R^{41}$ and $R^{51}$ are each independently selected from the group consisting of hydrogen, alkyl, alkenyl, hydroxyalkyl, haloalkyl, and aminoalkyl; and $R^{17}$ and $R^{18}$ are each independently selected from the group consisting of hydrogen, alkyl, cycloalkyl, halogen, cyano, amino, alkylamino, dialkylamino, hydroxy, nitro, haloalkyl, and alkoxy.

Preferably, $R^{41}$ and $R^{51}$ are each independently selected from the group consisting of hydrogen, alkyl, and hydroxyalkyl; and more preferably independently selected from hydrogen and alkyl. Useful compounds include those where $R^{41}$ and $R^{51}$ both are hydrogen, or $R^{41}$ is hydrogen and $R^{51}$ is $C_{1-3}$ alkyl, preferably methyl.

Preferably, $R^{17}$ and $R^{18}$ are each independently selected from the group consisting of hydrogen, $C_{1-6}$ alkyl, $C_{3-6}$ cycloalkyl, halogen, cyano, amino, $C_{1-3}$ alkylamino, di($C_{1-3}$) alkylamino, hydroxy, nitro, halo($C_{1-6}$)alkyl, and $C_{1-6}$ alkoxy; more preferably independently selected from the group consisting of hydrogen, $C_{1-4}$ alkyl, halogen, cyano, amino, $C_{1-3}$ alkylamino, di($C_{1-3}$)alkylamino, hydroxy, nitro, halo($C_{1-3}$) alkyl, and $C_{1-4}$ alkoxy; and more preferably independently selected from the group consisting of hydrogen, methyl, isopropyl, tert-butyl, cyano, fluoro, amino, methylamino, dimethylamino, nitro, trifluoromethyl, methoxy, iso-propoxy, and tert-butoxy. Useful compounds of Formula V include those where $R^{17}$ and $R^{18}$ are both hydrogen, or $R^{17}$ is hydrogen and $R^{18}$ is methyl, tert-butyl, cyano, fluoro, methylamino, dimethylamino, trifluoromethyl or methoxy, and especially cyano.

In one aspect, preferred compounds falling within the scope of Formula IV include those represented by Formula VI:

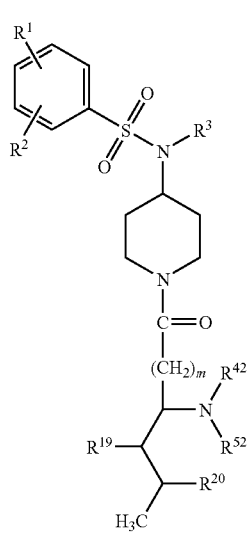

or a pharmaceutically acceptable salt, prodrug, or solvate thereof, wherein:

$R^1$-$R^3$ and m are as defined above for Formula I;

$R^{42}$ and $R^{52}$ are each independently selected from the group consisting of hydrogen, alkyl, alkenyl, hydroxyalkyl, haloalkyl, alkylthiol, and aminoalkyl; or $R^{42}$ and $R^{52}$ together with the nitrogen atom to which they are attached form a 5- or a 6-membered heterocyclic ring wherein one or more carbon atoms of the heterocyclic ring are optionally replaced with $NR^{16}$, O or S, wherein $R^{16}$ is hydrogen or $C_{1-3}$ alkyl; and $R^{19}$ and $R^{20}$ are independently H or $CH_3$.

Preferred values for $R^1$-$R^3$ are those described for Formula I. Preferably, $R^{42}$ and $R^{52}$ are each independently selected from the group consisting of hydrogen, alkyl, and hydroxyalkyl; more preferably selected from hydrogen, $C_{1-6}$ alkyl, and hydroxy($C_{1-6}$)alkyl; more preferably independently selected from hydrogen, $C_{1-3}$ alkyl, and hydroxy($C_{1-3}$)alkyl; and more preferably independently selected from hydrogen, methyl, ethyl, hydroxymethyl and hydroxyethyl; or $R^{42}$ and $R^{52}$ together with the nitrogen atom to which they are attached form a 5- or 6-membered heterocyclic ring selected from the group consisting of oxazolidinyl, isoxazolidinyl, pyrrolidinyl, pyrazolidinyl, imidazolidinyl, hexahydropyrimidinyl, piperidinyl, piperazinyl, 4-methylpiperazinyl, morpholinyl, thiomorpholinyl, and tetrahydropyridyl. Advantageously, $R^{42}$ and $R^{52}$ are independently hydrogen, methyl or hydroxyethyl; or $R^{42}$ and $R^{52}$ together with the nitrogen atom to which they are attached form 1-pyrrolidinyl, 4-thiomorpholinyl, or 4-methylpiperazinyl.

Useful compounds of Formula VI include those where one of $R^{19}$ or $R^{20}$ is $CH_3$. Other useful compounds of Formula VI include those where $R^{19}$ and $R^{20}$ are both H when $R^{42}$ and $R^{52}$ together form a 5- or 6-membered heterocyclic ring. Also, useful compounds of Formula VI include those where $R^{42}$ and $R^{52}$ are both hydrogen, or $R^{42}$ is hydrogen and $R^{52}$ is alkyl, and especially methyl. Preferably, m is 1 in compounds of Formula VI.

Another group of compounds useful in this aspect of the invention are piperidinyl compounds represented by the general Formula VII:

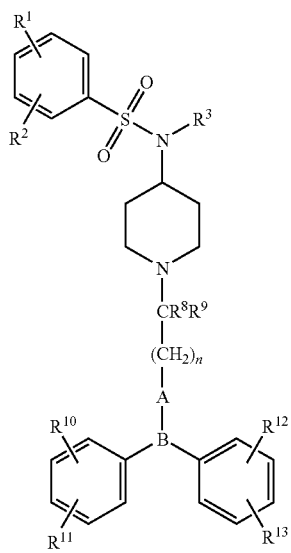

VII or a pharmaceutically acceptable salt, prodrug or solvate thereof, wherein:

$R^1$-$R^3$ are as defined previously for Formulae I-III;

$R^8$ and $R^9$ are both hydrogen or together form =O;

$R^{10}$, $R^{11}$, $R^{12}$ and $R^{13}$ are each independently selected from the group consisting of hydrogen, alkyl, alkoxy, halogen, haloalkyl, hydroxy, hydroxyalkyl, cyano, amino, aminoalkyl, alkylamino, and dialkylamino;

A is O, $CH_2$, or absent (a covalent bond), and B is CH, provided that when A is O, then $R^8$ and $R^9$ are both hydrogen; or A-B is CH=C; and n is 0, 1, 2, 3, 4, or 5.

In Formula VII, preferred values for $R^1$-$R^3$, $R^8$-$R^{13}$, A, B, and n are those described above for Formula I.

Further, compounds useful in the present invention are piperidinyl compounds of Formula VIII:

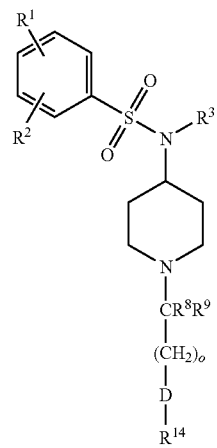

VIII or a pharmaceutically acceptable salt, prodrug or solvate thereof, wherein:

$R^1$-$R^3$, $R^8$, $R^9$, $R^{14}$, D, and o are as defined previously for Formula I. In Formula VIII, preferred values for $R^1$-$R^3$, $R^8$, $R^9$, $R^{14}$, D, and o are those described above for Formula I.

Additional compounds useful in the present invention are piperidinyl compounds represented by Formula IX:

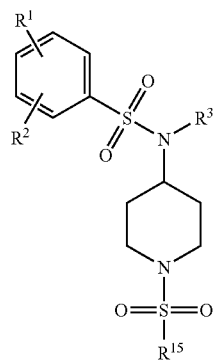

IX or a pharmaceutically acceptable salt, prodrug or solvate thereof, wherein:

$R^1$-$R^3$ and $R^{15}$ are as defined previously for Formula I. In Formula IX, preferred values for $R^1$-$R^3$ and $R^{15}$ are those described above for Formula I.

It has also been found that intermediates having the structure of Formula X have calcium channel blocking activity. Accordingly, the present invention is directed to compounds of Formula X as follows:

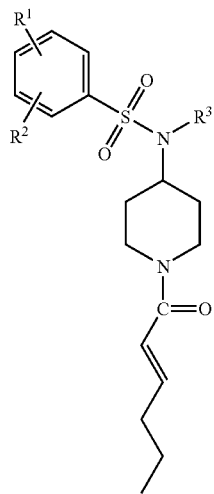

or a pharmaceutically acceptable salt, prodrug or solvate thereof, wherein:

R¹-R³ are as defined previously for Formula I. In Formula X, preferred values for R¹-R³ are those described above for Formula I.

Exemplary preferred compounds useful in the present invention include:

N-{1-[3-(4-cyanophenyl)-2-methylaminopropionyl]piperidin-4-yl}-N-cyclopropyl-3-trifluoromethylbenzenesulfonamide;
N-{1-[2-amino-3-(4-cyanophenyl)propionyl]piperidin-4-yl}-N-cyclopropyl-3-trifluoromethylbenzenesulfonamide;
N-[1-(2-amino-3-m-tolylpropionyl)piperidin-4-yl]-N-cyclopropyl-3-trifluoromethylbenzenesulfonamide;
N-{1-[2-amino-3-(4-fluorophenyl)propionyl]piperidin-4-yl}-N-cyclopropyl-3-trifluoromethylbenzenesulfonamide;
N-cyclopropyl-N-[1-(2-methylamino-3-phenylpropionyl)-piperidin-4-yl]-3-trifluoromethylbenzenesulfonamide;
N-[1-(2-amino-3-o-tolylpropionyl)piperidin-4-yl]-N-cyclopropyl-3-trifluoromethylbenzenesulfonamide;
N-{1-[2-amino-3-(4-tert-butylphenyl)propionyl]piperidin-4-yl}-N-cyclopropyl-3-trifluoromethylbenzenesulfonamide;
N-cyclopropyl-N-[1-(2-methylamino-3-o-tolylpropionyl)piperidin-4-yl]-3-trifluoromethylbenzenesulfonamide;
N-cyclopropyl-N-[1-(2-methylamino-3-m-tolylpropionyl)piperidin-4-yl]-3-trifluoromethylbenzenesulfonamide;
N-cyclopropyl-N-{1-[3-(4-fluorophenyl)-2-methylaminopropionyl]-piperidin-4-yl}-3-trifluoromethylbenzenesulfonamide;
N-cyclopropyl-N-{1-[3-(4-tert-butylphenyl)-2-methylamino-propionyl]piperidin-4-yl}-3-trifluoromethylbenzenesulfonamide;
N-cyclopropyl-N-[1-(3-thiomorpholin-4-yl-hexanoyl)piperidin-4-yl]-3-trifluoromethylbenzenesulfonamide;
N-methyl-N-[1-(4-methyl-2-methylaminopentanoyl)piperidin-4-yl]-3-trifluoromethylbenzenesulfonamide;
N-cyclopropyl-N-[1-(3-pyrrolidin-1-yl-hexanoyl)piperidin-4-yl]-3-trifluoromethylbenzenesulfonamide;
N-cyclopropyl-N-[1-(3-morpholin-4-ylhexanoyl)piperidin-4-yl]-3-trifluoromethylbenzenesulfonamide;
N-cyclopropyl-N-{1-[3-(4-methylpiperazin-1-yl)hexanoyl]piperidin-4-yl}-3-trifluoromethylbenzenesulfonamide;
N-cyclopropyl-N-{1-[3-(piperidin-1-yl)hexanoyl]piperidin-4-yl}3-trifluoromethylbenzenesulfonamide;
N-[1-(3-amino-5-methylhexanoyl)piperidin-4-yl]-N-cyclopropyl-3-trifluoromethylbenzenesulfonamide;
N-cyclopropyl-N-[1-(3-methylamino-5-methylhexanoyl)-piperidin-4-yl]-3-trifluoromethylbenzenesulfonamide;
N-[1-(3-amino-4-methylpentanoyl)piperidin-4-yl]-N-cyclopropyl-3-trifluoromethylbenzenesulfonamide;
N-cyclopropyl-N-[1-(3-methylamino-4-methylpentanoyl)-piperidin-4-yl]-3-trifluoromethylbenzenesulfonamide;
N-cyclopropyl-N-[1-(4-methyl-2-methylaminopentanoyl)-piperidin-4-yl]-3-trifluoromethylbenzenesulfonamide;
N-cyclopropyl-N-[1-(2-dimethylamino-4-methylpentanoyl)-piperidin-4-yl]-3-trifluoromethylbenzenesulfonamide;
N-cyclopropyl-N-[1-(3-methyl-2-methylaminopentanoyl)-piperidin-4-yl]-3-trifluoromethylbenzenesulfonamide;
N-[1-(2-aminopentanoyl)piperidin-4-yl]-N-cyclopropyl-3-trifluoromethylbenzenesulfonamide;
N-isopropyl-N-[1-(4-methyl-2-methylaminopentanoyl)piperidin-4-yl]-3-trifluoromethylbenzenesulfonamide;
N-cyclopropyl-N-[1-(2-methylaminopentanoyl)piperidin-4-yl]-3-trifluoromethylbenzenesulfonamide;
N-[1-(2-amino-3,3-dimethylbutanoyl)piperidin-4-yl]-N-cyclopropyl-3-trifluoromethylbenzenesulfonamide;
N-cyclopropyl-N-{1-3 [(2-hydroxyethylamino)hexanoyl]piperidin-4-yl}-3-trifluoromethylbenzenesulfonamide;
N-[1-(2-amino-2-cyclohexylethanoyl)piperidin-4-yl]-N-cyclopropyl-3-trifluoromethylbenzenesulfonamide;
N-[1-(2-amino-2-cyclohexylethanoyl)piperidin-4-yl]-N-cyclopropyl-3-trifluoromethylbenzenesulfonamide;
N-cyclopropyl-N-[1-(3-dimethylaminohexanoyl)piperidin-4-yl]-3-trifluoromethylbenzenesulfonamide;
N-cyclopropyl-N-[1-(2-methylamino-2-phenylethanoyl)piperidin-4-yl]-3-trifluoromethylbenzenesulfonamide; or
N-1-butyl-N-[1-(4-methyl-2-methylaminopentanoyl)piperidin-4-yl]-3-trifluoromethylbenzenesulfonamide;
N-[1-(2-amino-4-methylpentanoyl)piperidin-4-yl]-N-cyclopropyl-benzenesulfonamide;
N-(2-hydroxyethyl)-N-[1-(4-methyl-2-methylaminopentanoyl)-piperidin-4-yl]-3-trifluoromethylbenzenesulfonamide;
N-cyclopropyl-N-[1-(4-methyl-2-methylaminopentanoyl)-piperidin-4-yl]-4-trifluoromethylbenzenesulfonamide;
N-cyclopropyl-N-[1-(4-methyl-2-methylaminopentanoyl)-piperidin-4-yl]-2-fluorobenzenesulfonamide;
N-cyclopropyl-N-[1-(4-methyl-2-methylaminopentanoyl)-piperidin-4-yl]-2-trifluoromethylbenzenesulfonamide;
N-cyclopropyl-N-[1-(2-methylaminopropionyl)piperidin-4-yl]-3-trifluoromethylbenzenesulfonamide;
N-cyclopropyl-N-[1-(2-methylaminoethanoyl)piperidin-4-yl]-3-trifluoromethylbenzenesulfonamide;
N-1-pentyl-N-[1-(4-methyl-2-methylaminopentanoyl)piperidin-4-yl]-3-trifluoromethylbenzenesulfonamide;
N-cyclopropyl-N-[1-(4-methyl-2-methylaminopentanoyl)-piperidin-4-yl]-3-methoxybenzenesulfonamide;
N-cyclopropyl-N-[1-(4-methyl-2-methylaminopentanoyl)-piperidin-4-yl]-3-difluoromethoxybenzenesulfonamide;
N-cyclopropyl-N-[1-(4-methyl-2-methylaminopentanoyl)-piperidin-4-yl]-3-cyanobenzenesulfonamide;

N-cyclopropyl-N-[1-(4-methyl-2-methylaminopentanoyl)-piperidin-4-yl]-3-chlorobenzenesulfonamide;
N-cyclopropyl-N-[1-(4-methyl-2-methylaminopentanoyl)-piperidin-4-yl]-3-methylbenzenesulfonamide;
N-cyclopropyl-N-[1-(4-methyl-2-methylaminopentanoyl)-piperidin-4-yl]-3-nitrobenzenesulfonamide;
N-cyclopropyl-N-[1-(3-hydroxy-2-methylaminopropanoyl)-piperidin-4-yl]-3-trifluoromethylbenzenesulfonamide;
N-[1-(1-aminocyclopentan-1-carbonyl)piperidin-4-yl]-N-cyclopropyl-3-trifluoromethylbenzenesulfonamide;
N-cyclopropyl-N-[1-(1,2,3,4-tetrahydroisoquinolin-3-carbonyl)piperidin-4-yl]-3-trifluoromethylbenzenesulfonamide;
N-cyclopropyl-N-[1-(piperidin-2-oyl)piperidin-4-yl]-3-trifluoromethyl-benzenesulfonamide;
N-[1-(3-benzyloxy-2-methylaminopropanoyl)-piperidin-4-yl]-N-cyclopropyl-3-trifluoromethylbenzenesulfonamide;
N-cyclopropyl-N-[1-(N-methylpyrrolidin-2-carbonyl)piperidin-4-yl]-3-trifluoromethylbenzenesulfonamide;
N-cyclopropyl-N-[1-(pyrrolidin-2-carbonyl)piperidin-4-yl]-3-trifluoromethylbenzenesulfonamide;
N-[1-(2-cyclohexyl-2-methylaminoethanoyl)piperin-4-yl]-N-cyclopropyl-3-trifluoromethylbenzenesulfonamide;
N-cyclopropylmethyl-N-[1-(2-methylamino-4-methylpentanoyl)-piperidin-4-yl]-3-trifluoromethylbenzenesulfonamide;
N-cyclopropyl-N-[1-(4-dimethylaminobenzyl)piperidin-4-yl]-3-trifluoromethylbenzenesulfonamide;
N-cyclopropyl-N-{1-[(3-trifluoromethyl-4-methoxy)benzoyl]piperidin-4-yl}-3-trifluoromethylbenzenesulfonamide;
N-cyclopropyl-N-[1-(2-dimethylamino-3,3-dimethylbutanoyl)-piperidin-4-yl]-3-trifluoromethylbenzenesulfonamide; and
N-cyclopropyl-N-[1-(1-phenylaminocyclohexan-1-oyl)piperidin-4-yl]-3-trifluoromethylbenzenesulfonamide;
or a pharmaceutically acceptable salt, prodrug or solvate thereof.

Other exemplary preferred compounds useful in the present invention include:
(2S) N-cyclopropyl-N-[1-(2-methylamino-3-phenylpropionyl)-piperidin-4-yl]-3-trifluoromethylbenzenesulfonamide;
(2S) N-methyl-N-[1-(4-methyl-2-methylaminopentanoyl) piperidin-4-yl]-3-trifluoromethylbenzenesulfonamide;
(3S) N-[1-(3-amino-5-methylhexanoyl)piperidin-4-yl]-N-cyclopropyl-3-trifluoromethylbenzenesulfonamide;
(3S) N-cyclopropyl-N-[1-(3-methylamino-5-methylhexanoyl)-piperidin-4-yl]-3-trifluoromethylbenzenesulfonamide;
(3S) N-[1-(3-amino-4-methylpentanoyl)piperidin-4-yl]-N-cyclopropyl-3-trifluoromethylbenzenesulfonamide;
(3S) N-cyclopropyl-N-[1-(3-methylamino-4-methylpentanoyl)-piperidin-4-yl]-3-trifluoromethylbenzenesulfonamide;
(2S) N-cyclopropyl-N-[1-(4-methyl-2-methylaminopentanoyl)-piperidin-4-yl]-3-trifluoromethylbenzenesulfonamide;
(2R) N-cyclopropyl-N-[1-(4-methyl-2-methylaminopentanoyl)-piperidin-4-yl]-3-trifluoromethylbenzenesulfonamide;
(2S) N-cyclopropyl-N-[1-(2-dimethylamino-4-methylpentanoyl)-piperidin-4-yl]-3-trifluoromethylbenzenesulfonamide;
(2R) N-cyclopropyl-N-[1-(2-dimethylamino-4-methylpentanoyl)-piperidin-4-yl]-3-trifluoromethylbenzenesulfonamide;
(2S) N-cyclopropyl-N-[1-(3-methyl-2-methylaminopentanoyl)-piperidin-4-yl]-3-trifluoromethylbenzenesulfonamide;
(2S) N-[1-(2-aminopentanoyl)piperidin-4-yl]-N-cyclopropyl-3-trifluoromethylbenzenesulfonamide;
(2S) N-isopropyl-N-[1-(4-methyl-2-methylaminopentanoyl) piperidin-4-yl]-3-trifluoromethylbenzenesulfonamide;
(2S) N-cyclopropyl-N-[1-(2-methylaminopentanoyl)piperidin-4-yl]-3-trifluoromethylbenzenesulfonamide;
(2S) N-[1-(2-amino-3,3-dimethylbutanoyl)piperidin-4-yl]-N-cyclopropyl-3-trifluoromethylbenzenesulfonamide;
(2S) N-[1-(2-amino-2-cyclohexylethanoyl)piperidin-4-yl]-N-cyclopropyl-3-trifluoromethylbenzenesulfonamide;
(2R) N-[1-(2-amino-2-cyclohexylethanoyl)piperidin-4-yl]-N-cyclopropyl-3-trifluoromethylbenzenesulfonamide;
(2S) N-cyclopropyl-N-[1-(2-methylamino-2-phenylethanoyl)piperidin-4-yl]-3-trifluoromethylbenzenesulfonamide;
(2S) N-1-butyl-N-[1-(4-methyl-2-methylaminopentanoyl) piperidin-4-yl]-3-trifluoromethylbenzenesulfonamide;
(2R) N-[1-(2-amino-4-methylpentanoyl)piperidin-4-yl]-N-cyclopropyl-benzenesulfonamide;
(2S) N-(2-hydroxyethyl)-N-[1-(4-methyl-2-methylaminopentanoyl)-piperidin-4-yl]-3-trifluoromethylbenzenesulfonamide;
(2S) N-cyclopropyl-N-[1-(4-methyl-2-methylaminopentanoyl)-piperidin-4-yl]-4-trifluoromethylbenzenesulfonamide;
(2S) N-cyclopropyl-N-[1-(4-methyl-2-methylaminopentanoyl)-piperidin-4-yl]-2-fluorobenzenesulfonamide;
(2S) N-cyclopropyl-N-[1-(4-methyl-2-methylaminopentanoyl)-piperidin-4-yl]-2-trifluoromethylbenzenesulfonamide;
(2S) N-cyclopropyl-N-[1-(2-methylaminopropionyl)piperidin-4-yl]-3-trifluoromethylbenzenesulfonamide;
(2S) N-1-pentyl-N-[1-(4-methyl-2-methylaminopentanoyl) piperidin-4-yl]-3-trifluoromethylbenzenesulfonamide;
(2S) N-cyclopropyl-N-[1-(4-methyl-2-methylaminopentanoyl)-piperidin-4-yl]-3-methoxybenzenesulfonamide;
(2S) N-cyclopropyl-N-[1-(4-methyl-2-methylaminopentanoyl)-piperidin-4-yl]-3-difluoromethoxybenzenesulfonamide;
(2S) N-cyclopropyl-N-[1-(4-methyl-2-methylaminopentanoyl)-piperidin-4-yl]-3-cyanobenzenesulfonamide;
(2S) N-cyclopropyl-N-[1-(4-methyl-2-methylaminopentanoyl)-piperidin-4-yl]-3-chlorobenzenesulfonamide;
(2S) N-cyclopropyl-N-[1-(4-methyl-2-methylaminopentanoyl)-piperidin-4-yl]-3-methylbenzenesulfonamide;
(2S) N-cyclopropyl-N-[1-(4-methyl-2-methylaminopentanoyl)-piperidin-4-yl]-3-nitrobenzenesulfonamide;
(2S) N-cyclopropyl-N-[1-(3-hydroxy-2-methylaminopropanoyl)-piperidin-4-yl]-3-trifluoromethylbenzenesulfonamide;
(2S) N-[1-(1-aminocyclopentan-1-carbonyl)piperidin-4-yl]-N-cyclopropyl-3-trifluoromethylbenzenesulfonamide;
(2S) N-[1-(3-benzyloxy-2-methylaminopropanoyl)-piperidin-4-yl]-N-cyclopropyl-3-trifluoromethylbenzenesulfonamide;
(2S) N-cyclopropyl-N-[1-(pyrrolidin-2-carbonyl)piperidin-4-yl]-3-trifluoromethylbenzenesulfonamide;
(2S) N-[1-(2-cyclohexyl-2-methylaminoethanoyl)piperin-4-yl]-N-cyclopropyl-3-trifluoromethylbenzenesulfonamide;
(2S) N-cyclopropylmethyl-N-[1-(2-methylamino-4-methylpentanoyl)-piperidin-4-yl]-3-trifluoromethylbenzenesulfonamide;

(2S) N-cyclopentyl-N-[1-(4-methyl-2-methylamino-pentanoyl)-piperidin-4-yl]-3-trifluoromethylbenzenesulfonamide;

(2S) N-[1-(4-methyl-2-methylaminopentanoyl)piperidin-4-yl]-N-(tetrahydrofuran-3-yl)-3-trifluoromethylbenzenesulfonamide, and (2S) N-cyclopropyl-N-[1-(2-dimethylamino-3,3-dimethylbutanoyl)-piperidin-4-yl]-3-trifluoromethylbenzenesulfonamide;

(2S) N-(2-methoxyethyl)-N-[1-(4-methyl-2-methylaminopentanoyl)-piperidin-4-yl]-3-trifluoromethylbenzenesulfonamide;

(2S) N-[1-(4-methyl-2-methylaminopentanoyl)piperidin-4-yl]-N-(tetrahydrofuran-2-yl)methyl-3-trifluoromethylbenzenesulfonamide;

(2S) N-cyclopropyl-N-[1-(4-methyl-2-methylaminopentanoyl)-piperidin-4-yl]-3-fluorobenzenesulfonamide;

(2S) N-[1-(2-amino-4-methylpentanoyl)piperidin-4-yl]-N-cyclopropyl-benzenesulfonamide;

or a pharmaceutically acceptable salt, prodrug or solvate thereof.

Other exemplary compounds useful in the present invention include:

N-cyclopropyl-N-{1-[4,4-bis(4-fluorophenyl)butyl]piperidin-4-yl}-3-trifluoromethylbenzenesulfonamide;

N-cyclopropyl-N-{1-[4,4-bis(4-fluorophenyl)butyl]piperidin-4-yl}benzenesulfonamide;

N-cyclopropyl-N-{1-[4,4-bis(4-fluorophenyl)butyl]piperidin-4-yl}-3-chlorobenzenesulfonamide;

N-cyclopropyl-N-{1-[4,4-bis(4-fluorophenyl)but-3-enoyl]piperidin-4-yl}-3-trifluoromethylbenzenesulfonamide;

N-cyclopropyl-N-{1-[4,4-bis(4-fluorophenyl)but-3-enoyl]piperidin-4-yl}benzenesulfonamide;

N-cyclopropyl-N-{1-[4,4-bis(4-fluorophenyl)butanoyl]piperidin-4-yl}-3-trifluoromethylbenzenesulfonamide;

N-cyclopropyl-N-{1-[4,4-bis(4-fluorophenyl)butanoyl]piperidin-4-yl}benzenesulfonamide;

N-cyclopropyl-N-{1-[4,4-bis(4-fluorophenyl)butanoyl]piperidin-4-yl}-3-fluorobenzenesulfonamide;

N-cyclopropyl-N-[1-(2,2-diphenylethyl)piperidin-4-yl]benzenesulfonamide;

N-cyclopropyl-N-[1-(3,3-diphenylpropanoyl)piperidin-4-yl]-3-trifluoromethylbenzenesulfonamide N-cyclopropyl-N-{1-[4,4-bis(4-fluorophenyl)butanoyl]piperidin-4-yl}-2-trifluoromethylphenylbenzenesulfonamide;

N-cyclopropyl-N-{1-[2-bis(4-fluorophenyl)methoxyethyl]piperidin-4-yl}benzenesulfonamide; and N-cyclopropyl-N-{1-[2-bis(4-fluorophenyl)methoxyethyl]piperidin-4-yl}-3-trifluoromethylbenzenesulfonamide;

or a pharmaceutically acceptable salt, prodrug, or solvate thereof.

Other exemplary compounds useful in the present invention include:

N-cyclopropyl-N-[1-(napht-2-ylmethyl)piperidin-4-yl]benzene-sulfonamide;

N-cyclopropyl-N-[1-(4-phenylbenzyl)piperidin-4-yl]benzene-sulfonamide;

N-cyclopropyl-N-[1-(4-isopropylbenzyl)piperidin-4-yl]benzene-sulfonamide;

N-cyclopropyl-N-[1-(4-trifluoromethyl-4-methoxybenzyl)piperidin-4-yl]benzenesulfonamide;

N-cyclopropyl-N-[1-(4-dimethylaminobenzyl)piperin-4-yl]-3-trifluoromethylbenzenesulfonamide;

N-cyclopropyl-N-[1-(4-tert-butylbenzyl)piperidin-4-yl]benzene-sulfonamide;

N-cyclopropyl-N-[1-(4-trifluoromethyl-4-methoxybenzyl)piperidin-4-yl]-3-trifluoromethylbenzenesulfonamide;

N-cyclopropyl-N-[1-(3-methyl-4-methoxybenzyl)piperidin-4-yl]-3-trifluoromethylbenzenesulfonamide;

N-cyclopropyl-N-[1-(3-methyl-4-methoxybenzyl)piperidin-4-yl]-benzenesulfonamide;

N-cyclopropyl-N-[1-(3-pyridylmethyl)piperidin-4-yl]-3-trifluoromethylbenzenesulfonamide;

N-cyclopropyl-N-[1-(4-quinolinylmethyl)piperidin-4-yl]-3-trifluoromethylbenzenesulfonamide;

N-cyclopropyl-N-[1-(4-methoxybenzyl)piperidin-4-yl]-3-trifluoromethylbenzenesulfonamide;

N-cyclopropyl-N-{1-[4-(4-fluorophenyl)-4-oxobutyl]piperidin-4-yl}benzenesulfonamide;

N-cyclopropyl-N-{1-[(3-trifluoromethyl-4-methoxy)phenyl-methanoyl]piperidin-4-yl}-3-trifluoromethylbenzenesulfonamide;

N-cyclopropyl-N-{1-[4-(4-fluorophenyl)-4-oxobutanoyl]piperidin-4-yl}-3-trifluoromethylbenzenesulfonamide;

N-cyclopropyl-N-{1-[4-(4-fluorophenyl)-4-oxobutanoyl]piperidin-4-yl}benzenesulfonamide;

N-[1-(4-benzyloxybenzyl)piperidin-4-yl]-N-cyclopropyl-benzenesulfonamide;

N-cyclopropyl-N-[1-(4-methoxybenzyl)piperidin-4-yl]benzenesulfonamide;

N-cyclopropyl-N-{1-[3-(4-dimethylaminophenyl)propen-2-yl]piperidin-4-yl}benzenesulfonamide;

N-cyclopropyl-N-[1-(4-dimethylaminobenzyl)piperidin-4-yl]benzenesulfonamide;

N-cyclopropyl-N-{1-[4-(4-fluorophenoxy)benzoyl)]piperidin-4-yl}-3-trifluoromethylbenzenesulfonamide; and N-cyclopropyl-N-[1-(4-dimethylaminobenzoyl)piperidin-4-yl]-3-trifluoromethylbenzenesulfonamide;

or a pharmaceutically acceptable salt, prodrug or solvate thereof.

Other exemplary compounds useful in the present invention include:

N-[1-(4-butoxyphenylsulfonyl)piperidin-4-yl]-N-cyclopropyl-benzenesulfonamide;

N-cyclopropyl-N-[1-(4-propylphenylsulfonyl)piperidin-4-yl]-3-trifluoromethylbenzenesulfonamide;

N-[1-(4-butoxyphenylsulfonyl)piperidin-4-yl]-N-cyclopropyl-3-trifluoromethylbenzenesulfonamide;

N-cyclopropyl-N-[1-(4-propylphenylsulfonyl)piperidin-4-yl]benzenesulfonamide; and N-cyclopropyl-N-[1-(5-dimethylaminonaphthylsulfonyl)piperidin-4-yl]benzenesulfonamide, or a pharmaceutically acceptable salt, prodrug, or solvate thereof.

Useful cycloalkyl groups are $C_{3-12}$ cycloalkyl. Typical cycloalkyl groups include cyclopropyl, cyclobutyl, cyclopentyl, cyclohexyl, cycloheptyl, and cyclooctyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, iso-butyl, 3-pentyl, hexyl and octyl groups.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec-butenyl.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl and trichloromethyl groups).

Useful hydroxyalkyl groups include $C_{1-10}$ alkyl groups substituted by hydroxy (e.g., hydroxymethyl, hydroxyethyl, hydroxypropyl and hydroxybutyl groups).

Useful alkoxy groups include oxygen substituted by one of the $C_{1-10}$ alkyl groups mentioned above.

Useful haloalkoxy groups include oxygen substituted by one of the $C_{1-10}$ haloalkyl groups mentioned above (e.g., fluoromethoxy, difluoromethoxy, and trifluoromethoxy).

The terms "heterocyclic" and "heterocyclo" are used herein to mean saturated or wholly or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. Examples include, but are not limited to, pyrrolidine, piperidine, piperazine, morpholine, imidazoline, pyrazolidine, benzodiazepines, and the like.

Useful alkylamino and dialkylamino groups are $-NHR^{21}$ and $-NR^{21}R^{22}$, wherein $R^{21}$ and $R^{22}$ are $C_{1-10}$ alkyl groups.

Useful alkylsulfonylaminoalkyl groups include any of the above-mentioned $C_{1-10}$ alkyl groups substituted by an alkyl-$SO_2-NH-$ group.

Useful aminocarbonylalkyl groups include any of the above-mentioned $C_{1-10}$ alkyl groups substituted with an aminocarbonyl group, i.e., $-C(O)NH_2$.

Useful alkylthiol groups include any of the above-mentioned $C_{1-10}$ alkyl groups substituted by a $-SH$ group.

An amino group is $-NH_2$.

The invention disclosed herein is also meant to encompass prodrugs of the disclosed compounds. Prodrugs are considered to be any covalently bonded carriers that release the active parent drug in vivo. Examples of prodrugs include esters or amides of Formulae I-X with hydroxyalkyl or aminoalkyl as a substituent, and these may be prepared by reacting such compounds with anhydrides such as succinic anhydride.

The invention disclosed herein is also meant to encompass the in vivo metabolic products of the disclosed compounds. Such products may result, for example, from the oxidation, reduction, hydrolysis, amidation, esterification and the like, of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Isotopically-labeled compounds of the present invention can be prepared by methods known in the art.

The present invention is also directed specifically to $^3H$ and $^{14}C$ radiolabeled compounds of Formula I or X, and their use as radioligands for their binding site on the calcium channel. For example, one use of the labeled compounds of the invention is the characterization of specific receptor binding. Another use of the labeled compounds of the present invention is an alternative to animal testing for the evaluation of structure-activity relationships. The receptor assay is performed at a fixed concentration of a labeled compound of Formula I or X and at increasing concentrations of a test compound in a competition assay. Tritiated compounds of Formula I or X can be prepared by introducing tritium into the compound of Formula I or X, for example, by catalytic dehalogenation with tritium. This method includes reacting a suitably halogen-substituted precursor of a compound of Formula I or X with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Some of the compounds disclosed herein may contain one or more asymmetric centers and may thus give rise to enantiomers, diastereomers, and other stereoisomeric forms. The present invention is meant to encompass all such possible forms, as well as their racemic and resolved forms and mixtures thereof. The individual enantiomers may be separated according to methods that are well known to those of ordinary skill in the art. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The invention disclosed herein also encompasses all non-toxic pharmaceutically acceptable salts thereof of the disclosed compounds. Examples of pharmaceutically acceptable addition salts include inorganic and organic acid addition salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts are formed by mixing a solution of the particular piperidinyl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the piperidinyl compound of the present invention with a solution of a pharmaceutically acceptable non-toxic base such as sodium hydroxide, potassium hydroxide, choline hydroxide, sodium carbonate and the like.

The present invention is also directed to a method for treating a disorder responsive to the blockade of calcium channels, and particularly the selective blockade of N-type calcium channels, in an animal suffering from said disorder, said method comprising administering to the animal an effective amount of a piperidinyl compound represented by any of defined Formulae I-X.

The present invention is also directed to a calcium mobilization assay that can be employed to identify compounds that can modulate or block calcium channels. In one aspect, the assay described herein is employed to identify compounds that block voltage-gated calcium channels, especially N-type calcium channels. In another aspect, the assay described herein is employed to predict whether a compound binds to an N-type calcium channel that is in the inactivated state.

In one aspect, it has been found that compounds identified using the assay described herein selectively block N-type calcium channels and, thus, are useful for treating disorders responsive to the selective blockade of N-type calcium channels. Therefore, the present invention provides a method of identifying compounds useful for treating, preventing or ameliorating stroke, head trauma, epilepsy, pain (e.g., acute pain, or chronic pain, which includes but is not limited to neuropathic pain and inflammatory pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In each instance, the compounds identified using the assay described herein can be administered in an effective amount to an animal in need of such treatment, prevention, or amelioration.

The invention disclosed herein also encompasses all non-toxic pharmaceutically acceptable salts thereof of the identified compounds.

The present invention is also directed to a method for treating a disorder responsive to the blockade of calcium channels, and particularly the selective blockade of N-type calcium channels, in an animal suffering from said disorder, said method comprising administering to the animal an effective amount of compound identified using the assay described herein or a pharmaceutically acceptable salt of the identified compound.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes. In each instance, the methods of the present invention require administering to an animal in need of such treatment an effective amount of a calcium channel blocker of the present invention, or a pharmaceutically acceptable salt, prodrug or solvate thereof.

Chronic somatic pain generally results from inflammatory responses to tissue injury such as nerve entrapment, surgical procedures, cancer or arthritis (Brower, *Nature Biotechnology* 2000; 18: 387-391). Although many types of inflammatory pain are currently treated with NSAIDs, there is much room for improved therapies.

The inflammatory process is a complex series of biochemical and cellular events activated in response to tissue injury or the presence of foreign substances (Levine, *Inflammatory Pain, In: Textbook of Pain*, Wall and Melzack eds., $3^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic neuropathic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

Synthesis of Compounds

The compounds of this invention may be prepared using methods known to those skilled in the art in view of this disclosure. For example, compounds of Formula I where Z is $Z^1$ can be prepared as shown in Scheme 1:

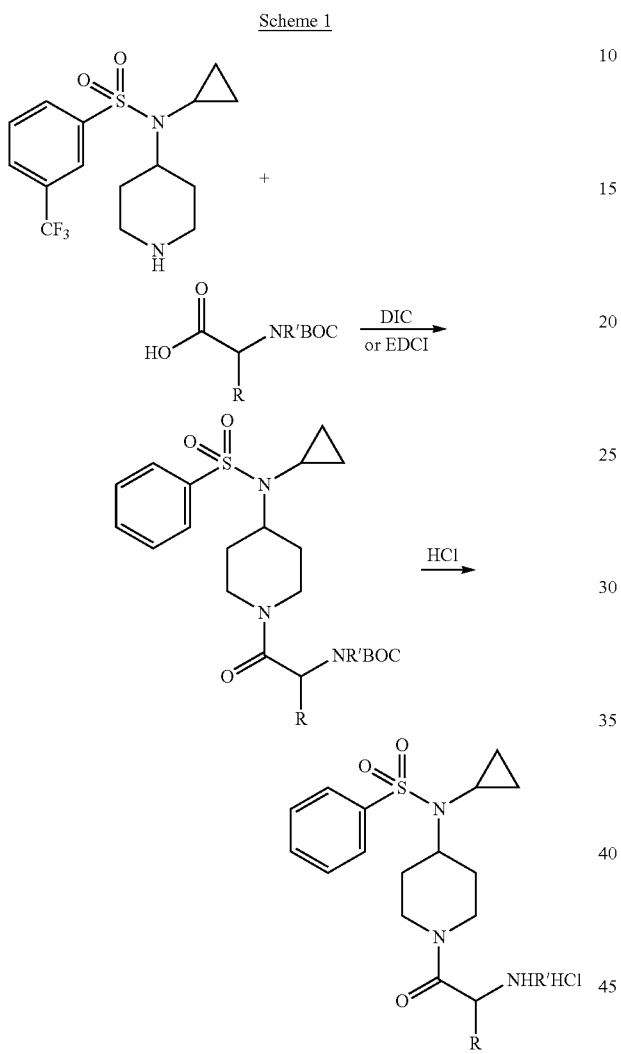

where R is hydrogen, alkyl, hydroxyalkyl, alkoxyalkyl, haloalkyl, aminoalkyl, cycloalkyl, optionally substituted phenyl, optionally substituted benzyl, or benzyloxyalkyl and R' is hydrogen, alkyl, alkenyl, hydroxyalkyl, haloalkyl, aminoalkyl or phenyl.

For example, a mixture of N-cyclopropyl-N-piperidin-4-yl-3-trifluoromethyl-benzenesulfonamide (1.0 eq.), BOC-amino acid (1.0 eq.), and 1-hydroxybenzotriazole hydrate (0.5-1.0 eq.) in a suitable solvent, such as DMF, is treated with N-ethyl-dimethylaminopropyl carbodiimide hydrochloride (EDCI) (1.0 eq) at room temperature for about 8 hours. The reaction mixture is then diluted with EtOAc, and washed with water and brine. The organic layer is concentrated, and purified by column (silica gel, EtOAc/hexane) to give the BOC-protected material, which is treated with HCl solution (4N in 1,4-dioxane) at room temperature to afford the desired product as a HCl-salt.

Compounds of Formula I where Z is $Z^1$ can also be prepared as shown in Scheme 2:

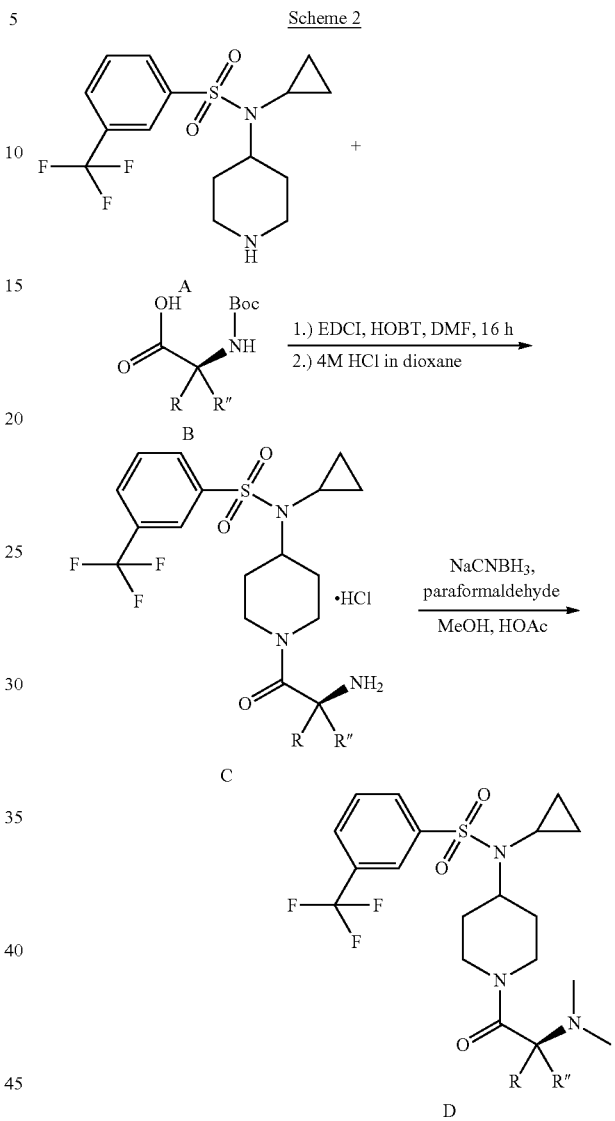

where R is hydrogen, alkyl, hydroxyalkyl, alkoxyalkyl, haloalkyl, aminoalkyl, cycloalkyl, optionally substituted phenyl, optionally substituted benzyl, or benzyloxyalkyl, and R" is hydrogen, or R and R" together with the carbon atom to which they are attached form a $C_{3-7}$ cycloalkyl group.

For example, the amine A (1 eq.) and the amino acid tail B (1 eq.) are dissolved in 4 mL of dimethyl formamide and then 1-[3-(dimethylmethylamino)propyl]-3-ethylcarbodiimide hydrochloride (1 eq.) and 1-hydroxybenzotriazole hydrate (1 eq.) are added to the mixture. The mixture is shaken overnight and then diluted with 20 mL of ethyl acetate and washed with 15 mL each of 10% aqueous HCl, saturated sodium bicarbonate, and brine. The combined aqueous layers are extracted twice with 20 mL of ethyl acetate, and the combined organic layers are dried over sodium sulfate. The solvent is removed under reduced pressure, and the material is purified, for example, by using the combiflash purification system. The pure material is deprotected by treating it with excess 4 M HCl in dioxane to give compound C. Compound C is dissolved in methanol under a nitrogen atmosphere with 4 Å molecular sieves. To this is added paraformaldehyde (1 eq.) and acetic acid (catalytic amount), and the reaction mixture is stirred for 30 minutes. Sodium cyanoborohydride (2 eq.) is then added to the mixture, and the reaction mixture is stirred overnight. If at this time no reaction is seen, additional portions of paraformaldehyde and cyanoborohydride can be added. After an additional day, the reaction mixture is diluted with 20 mL of ethyl acetate and quenched with 20 mL of 1 M sodium hydroxide. The aqueous layer is extracted three times with ethyl acetate, and the combined organic layers are dried over sodium sulfate. The material is treated with an excess of 4 M HCl in dioxane to form the HCl salt. After trituration with ether/hexanes, the material is dried to give the HCl salt of compound D.

A further method for preparing compounds of Formula I where Z is $Z^1$ is shown in Scheme 3:

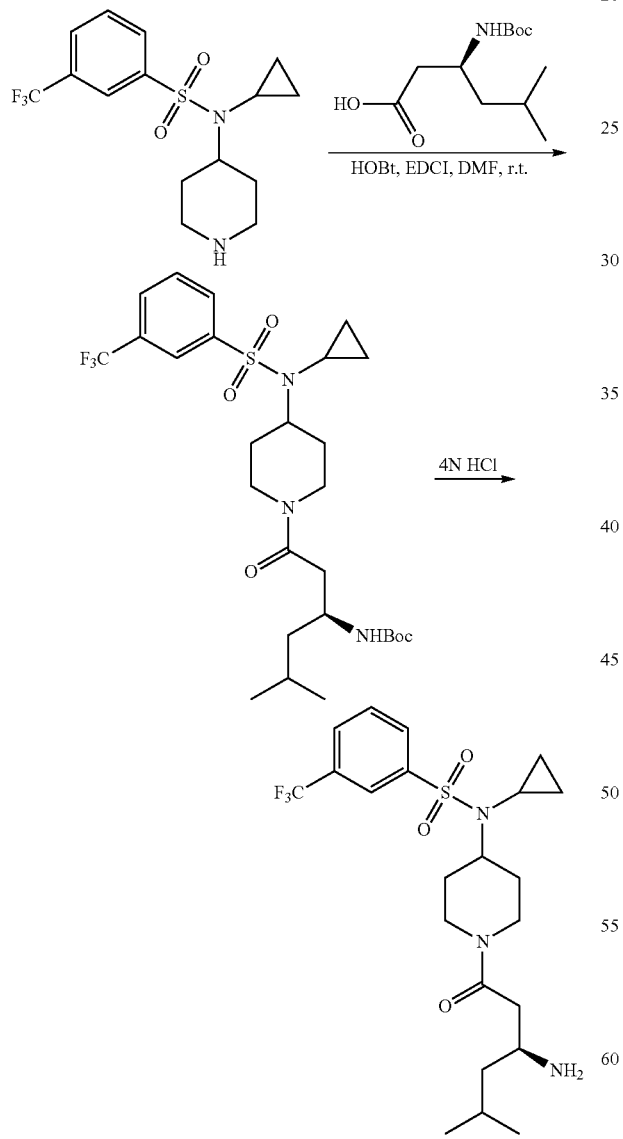

Compounds of Formula I where Z is $Z^1$ and m is 1 can be synthesized using the Michael addition reaction of amines to α,β-unsaturated amides as shown in Scheme 4:

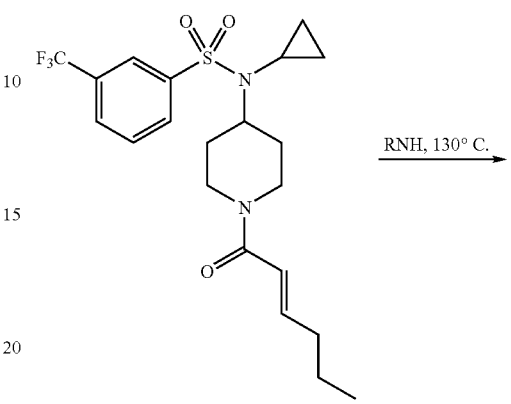

where R is hydrogen, alkyl, alkenyl, hydroxyalkyl, haloalkyl, aminoalkyl, or phenyl, or RN— is a 5- or 6-membered heterocyclic ring wherein one or more carbon atoms are optionally replaced with $NR^{16}$, O or S, wherein $R^{16}$ is hydrogen or $C_{1-3}$ alkyl.

For example, N-cyclopropyl-N-(1-hex-2-enoyl-piperidin-4-yl)-3-trifluoromethyl-benzenesulfonamide (250 mg, 0.56 mmol) and a primary or a secondary amine (2 mL) are heated together at 130° C. for 3 days in a sealed Reacti-vial. The vial is cooled in ice and then evaporated to dryness in vacuo in a Speed-Vac®. The residue can be chromatographed over flash silica to give the Michael adduct.

Compounds of Formula I where Z is $Z^2$ and $R^8$ and $R^9$ together form =O can be prepared as shown in Scheme 5:

The method of Scheme 3 is similar to that described in Scheme 1 except that the starting amino acid is a β-amino acid instead of an α-amino acid.

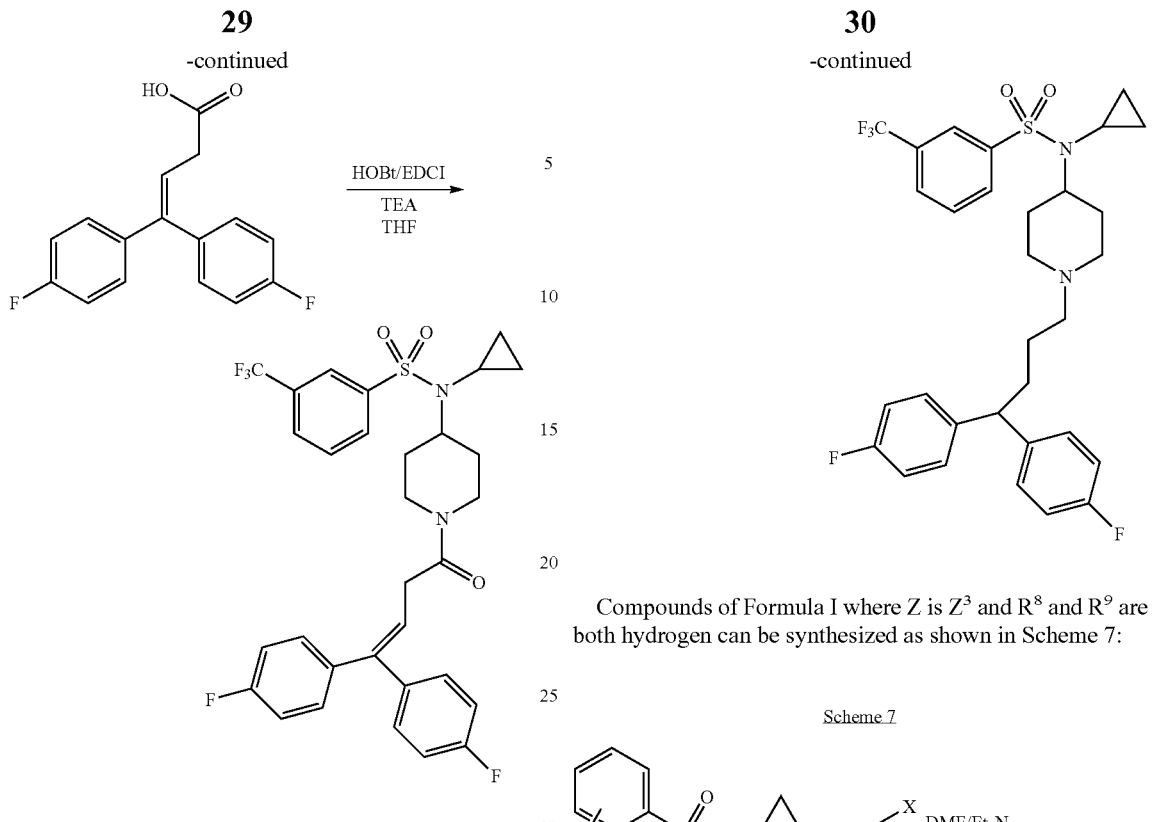

Accordingly, the amine and carboxylic acid are added in dry THF under nitrogen atmosphere. HOBT, EDCI, and triethylamine are added to the mixture, and the mixture is stirred at room temperature overnight. The resulting mixture is partitioned between ethyl acetate and 1.0 M sodium chloride. The organic layer is separated, dried and concentrated to give a crude product, which can be purified by crystallization by hexane/ether.

Compounds of Formula I where Z is $Z^2$ and $R^5$ and $R^9$ both are hydrogen can be prepared as shown in Scheme 6:

Scheme 6

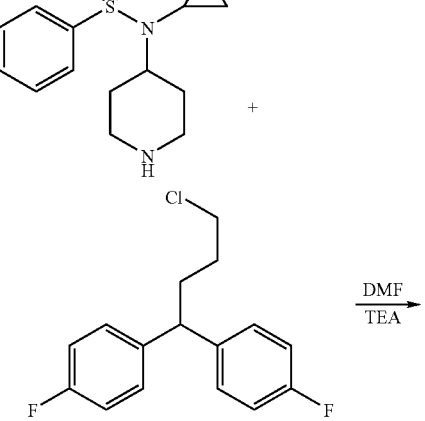

Compounds of Formula I where Z is $Z^3$ and $R^8$ and $R^9$ are both hydrogen can be synthesized as shown in Scheme 7:

Scheme 7

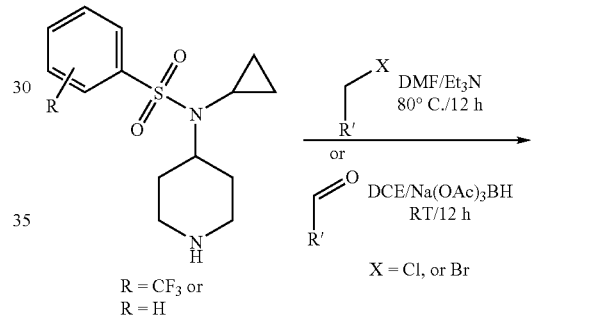

The amine, i.e., the piperidinyl compound, is dissolved in DMF and triethylamine added, followed by a halide R'CH$_2$X, wherein R' is optionally substituted phenyl. The reaction mixture is stirred for 12 hours at 80° C. and the solvent is evaporated. The residue can be purified by flash chromatography to give the desired product. When the appropriate benzyl halides are not available, corresponding aldehydes, R'C(O), can be used as follows: sodium triacetoxyborohydride (1.4 eq.) is added to a solution of an amine and an aldehyde in dichloroethane. The reaction mixture is stirred at room temperature for 12 hours. After this period, the solution is decanted and purified by flash chromatography to give the desired product.

Compounds of Formula I where Z is $Z^3$ and $R^8$ and $R^9$ together form =O can be synthesized using a method similar to that described in Scheme 5.

Compounds of Formula I where Z is $Z^4$ can be prepared as shown in Scheme 8:

Scheme 8

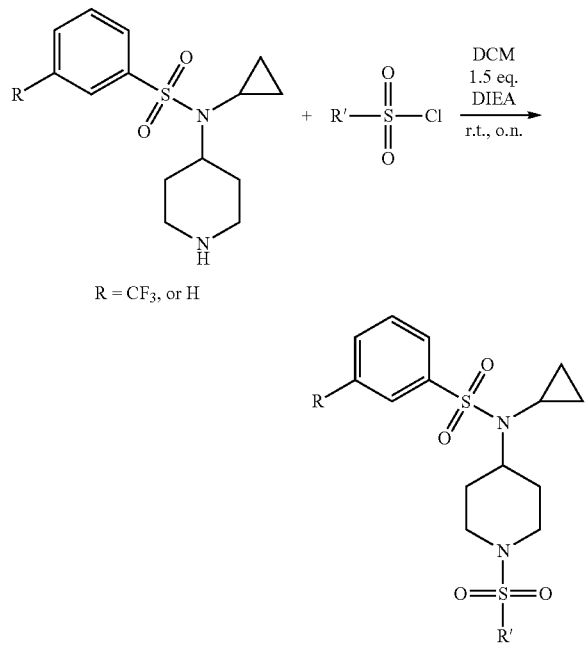

R = $CF_3$, or H

For example, 0.5 mmol of sulfonamide and approximately 0.5 mmol of the appropriate sulfonyl chloride are dissolved in 5 mL of DCM and combined with 1.5 eq. DIEA (0.134 mL) that is added by syringe. The mixture is stirred overnight at room temperature, and then concentrated under vacuum. The resulting product can be purified by using a column of silica gel with a gradient of 0% to 20% EtOAc in hexanes and the pure material is concentrated from the eluant.

The starting amine compounds used in the above reactions can be prepared, for example, as shown in Example 3, or they are commercially available from, for example, Lancaster.

Compounds of Formula X can be prepared, for example, as shown in Example 19.

Testing of Compounds

The compounds of the present invention were assessed by calcium mobilization and/or electrophysiological assays for calcium channel blocker activity. One aspect of the present invention is the discovery that the compounds herein described are selective N-type calcium channel blockers. Based upon this discovery, these compounds are considered useful in treating, preventing, or ameliorating migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also expected to be effective in treating, preventing or ameliorating pain, such as acute pain, neuropathic pain, inflammatory pain, surgical pain, or chronic pain.

More specifically, the present invention is directed to compounds of Formulae I-X that are blockers of calcium channels. According to the present invention, those compounds having preferred N-type calcium channel blocking properties exhibit an $IC_{50}$ of about 100 μM or less in the calcium mobilization and/or electrophysiological assays described herein. Preferably, the compounds of the present invention exhibit an $IC_{50}$ of 10 μM or less. Most preferably, the compounds of the present invention exhibit an $IC_{50}$ of about 1.0 μM or less. Piperidinyl compounds of the present invention can be tested for their N-type and L-type $Ca^{2+}$ channel blocking activity by the following calcium mobilization and/or electrophysiological assays.

In one embodiment, compounds useful in the present invention are those represented by any one of Formulae I-X that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an $IC_{50}$ for L-type channel blocking activity for a compound of the present invention over an $IC_{50}$ for N-type channel blocking activity for the compound is more than 1, i.e., LTCC $IC_{50}$/NTCC $IC_{50}$>1. Preferably, compounds of the present invention exhibit an LTCC $IC_{50}$/NTCC $IC_{50}$ ratio of about 2 or more. More preferably, compounds of the present invention exhibit an LTCC $IC_{50}$/NTCC $IC_{50}$ ratio of about 30 or more. Advantageously, compounds of the present invention exhibit an LTCC $IC_{50}$/NTCC $IC_{50}$ ratio of about 100 or more.

Calcium Mobilization Assay

The present invention provides a method for measuring the functional activity of N-type calcium channels in living cells by measuring N-type calcium channel activity using a calcium sensitive assay. The assay of the present invention provides for convenient optical methods for detecting calcium flux (influx or efflux). One can measure and observe the activity of the N-type calcium channel directly by detecting the flux of calcium in the cell.

Further, the invention provides an assay for identifying compounds that will modulate the activity of N-type calcium channels. In one aspect, the assay described herein provides a method for identifying compounds that will block the activity of N-type calcium channels. In another aspect, the assay described herein is employed to predict whether the compound that modulates or blocks the N-type calcium channel binds to an N-type calcium channel that is in the inactivated state.

A "channel modulator" is a compound that alters, directly or indirectly, the movement of ions through an ion channel. The compound may exert its effect by directly occluding the pore, by binding and preventing the opening of the pore, by binding and promoting opening of the pore, or by affecting the time and frequency of the opening of the ion channel.

A "channel blocker" is a compound that inhibits, directly or indirectly, the movement of ions through an ion channel. The compound may exert its effect by directly occluding the pore, by binding and preventing opening of the pore, or by affecting the time and frequency of the opening of the ion channel.

The assay of the present invention measures calcium mobilization in cells. As such, the assay of the present invention can be used to identify compounds that possess N-type calcium channel modulating or blocking activity. The effect of the N-type calcium channel modulators or blockers can be observed by measuring and observing the functional activity of the N-type calcium channel using the calcium sensitive assays described herein. Specifically, compounds can be tested for their ability to modulate or block N-type calcium channels using the assay described herein. The assay is also predictive of whether the blocker or modulator compounds bind to N-type calcium channels that are in the inactivated state.

Voltage-gated calcium channels open as a function of membrane potential such that the probability of opening increases with membrane potential. Voltage-gated calcium channels inactivate, close or desensitize as a function of membrane potential such that the probability of inactivation increases with a decrease in membrane potential or cell depolarization. A compound binding to a voltage-gated calcium channel often shows state dependence such that the binding affinity of a compound changes depending on the channel state. Control of membrane potential, which permits channels to be manipulated into different states in order to facilitate binding of a candidate blocking compound, is typically achieved by voltage-clamped electrophysiological methods. The assay of the present invention enables determination of state-dependent compound interactions with N-type calcium channel using optical methods.

Overview of the Assay

The present invention includes an assay for detecting and identifying compounds that are potential modulators or blockers of target N-type calcium channels. The assay of the present invention is also predictive of whether the compound binds to an N-type calcium channel, which is in the inactivated state.

The assay of the present invention is performed on cells that are maintained in the presence of one or more compounds that specifically block the activity of endogenously expressed calcium channels other than the N-type calcium channels, for example L-type calcium channels, P-type calcium channels, Q-type calcium channels, R-type calcium channels, and T-type calcium channels. Compounds that specifically block L-, P-, Q-, R-, or T-type calcium channels include nifedipine, nimodipine, verapamil, diltiazem, nicardipine, lercanipidine, efonidipine, lacidipine, mibefradil and nitrendipine, ω-aga-toxin-TK, $Pb^{2+}$, SNX-482, R(−)-isomer of efonidipine and others known in the art.

In the assay of the present invention, cell depolarization is used in a two-step manner. First, the membrane potential of the cells is decreased in the presence of the compound that will block the endogenously expressed calcium channels other than N-type calcium channels. Incubating the cells with this compound while the cells are in a depolarized state increases the potency with which this compound will bind to the channel, which in turn, will increase the blocking of the activity of the compound. Second, the membrane potential is decreased in the presence of a candidate compound. If a candidate compound binds to N-type calcium channels in the inactivated state, incubating the cells with a candidate compound while the cells are in a depolarized state increases the potency with which a candidate compound will bind to the N-type calcium channel, which in turn, will increase the modulator or blocker effect of a candidate compound on the activity of the N-type calcium channels. If a candidate compound does not bind to N-type calcium channels in the inactivated state, incubating the cells with a candidate compound while the cells are in a depolarized state will not increase the potency with which a candidate compound will bind to the N-type calcium channel, which in turn, will not increase the blocking effect of a candidate compound on the activity of the N-type calcium channels. Thus, the assay of the present invention is predictive of whether a candidate compound will bind to N-type calcium channels that are in the inactivated state.

The assay of the present invention provides a method for identifying a compound that modulates the activity of an N-type calcium channel. The method comprises the following steps:
- (a) incubating cells expressing an N-type calcium channel with a calcium-sensitive indicator for a time sufficient to allow incorporation of the indicator into the cells;
- (b) depolarizing the cells;
- (c) incubating the depolarized cells with a candidate modulator compound while maintaining the cells in a solution suitable to cause a flux of calcium ions through the channel;
- (d) measuring a signal from the calcium-sensitive indicator in the presence of the candidate modulator compound; and
- (e) comparing the signal from the calcium-sensitive indicator in the presence of the candidate modulator compound to a standard value.

The assay of the present invention involves incubating a test mixture, that includes cells expressing N-type channels, a detectable (signal generating) calcium-sensitive agent, potassium ions, and a compound that blocks the activity of other voltage-gated calcium channels expressed in the cell. A candidate N-type calcium channel activity modulator or blocker compound is then added. The optical signal of the calcium-sensitive agent is measured before and after the candidate compound is added. The assay is performed under conditions that are suitable for the N-type calcium channel activity to occur. A change in the optical signal of the calcium-sensitive agent is measured using a suitable apparatus. An increase or decrease in the signal indicates the movement of calcium ions through the N-type calcium channel. A change in the increase or decrease in the signal indicates a change in the magnitude of movement of calcium ions through the N-type calcium channel, thus indicating modulating activity of the candidate compound.

The assay of the present invention involves incubating a test mixture, that includes cells expressing a target N-type calcium channel, a detectable (signal generating) calcium-sensitive agent (e.g., Fluo-3, Fluo-4, Calcium green, and others), a compound that blocks the activity of endogenously expressed voltage-gated calcium channels, for example L-type calcium channels (e.g., nifedipene, nitrendipine and others), a concentration of potassium ions sufficient to depolarize the cell (10-150 mM) and a candidate N-type calcium channel activity blocker. The assay is performed under conditions that are suitable for the N-type calcium channel activity to occur and throughout the assay, the cells are maintained in the presence of the compound that blocks activity of endogenously expressed voltage-gated calcium channels other than the N-type calcium channel.

The optical signal of the calcium-sensitive agent is measured before and after the candidate calcium channel modulator or blocker is added. A change in the optical signal of the calcium-sensitive agent is measured. An increase or decrease in the signal indicates the movement of calcium ions through the N-type calcium channel. Changes in the increase or decrease in the signal indicates modulating or blocking of the movement of calcium ions through the N-type calcium channel.

One embodiment of the calcium mobilization assay of the invention is practiced using whole cells expressing an N-type calcium channel and comprises the steps of: 1) growing cells expressing N-type calcium channels under suitable conditions; 2) contacting or loading the cells with a signal generating calcium-sensitive agent e.g., Fluo-3 or Fluo-4; 3) treating the cells under suitable conditions (e.g., washing or adding extracellular quenchers) to remove the contribution of excess calcium-sensitive agent outside of the cells; 4) measuring the detectable signal for baseline measurement; 5) contacting the cells with a candidate N-type calcium channel modulator or blocker compound; and 6) detecting any signal, wherein each of the above recited steps are performed while cells are maintained in the presence of an L-type calcium channel blocker, e.g., nifedipine, nimodipine, verapamil, diltiazem, nicardipine, lercanipidine, efonidipine, lacidipine, mibefradil or nitrendipine, and others, and wherein the cells are maintained in an depolarized state while each of the L-type calcium channel blocking compound the candidate N-type calcium channel modulator or blocker compound is added.

The change in signal generated by the calcium-sensitive agent is determined by measuring the baseline signal in the test mixture before and after the addition of the candidate calcium channel blocking compound.

Typically voltage-gated channels are inactivated by either direct electrical stimulation with electrodes or by using a solution that contains an ionic composition that causes a change in membrane potential, specifically depolarization. Voltage-gated ion channels can be driven towards their inactivated state by incubation in a solution that contains a specific ionic composition that causes a change in membrane potential (such as high external potassium).

The assay of the present invention includes incubating cells in a solution that contains a specific ionic composition that causes a change in membrane potential, wherein the ionic composition is selected based on the type of ion channel used in the method. Selecting an appropriate ionic composition is within the skill of the art.

The ionic composition selected for use in the assay of the present invention can include activating reagents that serve to depolarize the membrane (e.g., ionophores, valinomycin, high extracellular potassium, etc.).

An ionic composition solution selected for depolarization of the cell membrane in the assay of the present invention includes a potassium salt at a concentration such that the final concentration of potassium ions in the cell-containing well is in the range of about 10-150 mM (e.g., 90 mM KCl).

The assay of the invention employs cells that endogenously express N-type calcium channels. The assay of the invention also employs cells that endogenously express potassium channels Exemplary cells include N18 neuroblastoma cells, AtT-20 mouse neuroendocrine cells, A7r5 rat thoracic aorta cells, SH-SY5Y neuroblastoma cells, PC12 pheochromocytoma cells, ScGT1-1 neuronal cells, HN2 neuronal cells, F11 neuroblastoma cells, L6 rat muscle cells, NG108-15 neuroblastomaxglioma hybrid cells, SCLC small cell lung carcinoma of neuroendocrine origin, NT2-N human tertocarcinoma cells, rat adrenal glomerulosa cells, rat pancreatic beta cells, INS-1 cells, SN56 neuronal cells, SKNSH neuroblastoma cells, and IMR32 human neuroblastoma cells.

The cells can be grown in solution or on a solid support. The cells can be adherent or non-adherent. Solid supports include glass or plastic culture dishes, and plates having one compartment, or multiple compartments, e.g., multi-well plates.

Although any number of cells capable of eliciting a detectable fluorescence signal in an assay can be used in a single-well or multi-well plate, the number of cells seeded into each well are chosen so that the cells are at or near confluence, but not overgrown, when the assays are conducted, so that the signal-to-background ratio of the signal is increased.

An embodiment of the invention for the calcium-sensitive agent is a fluorescent compound. Essentially any calcium-sensitive fluorescent compound that can be loaded into cells can be used. Preferably, the compound is selected to detect low concentrations of calcium ions. These fluorescent compounds can either show a decrease or an increase in fluorescence in the presence of calcium ions.

Suitable types of calcium-sensitive fluorescent agents include Fluo3, Fluo4, Fluo5, Calcium Green, Calcium Orange, Calcium Yellow, Fura-2, Fura-4, Fura-5, Fura-6, Fura-FF, Fura Red, indo-1, indo-5, BTC (Molecular Probes, Eugene, Oreg.), and FLIPR Calcium3 wash-free dye (Molecular Devices, Sunnyvale Calif.). The calcium-sensitive fluorescent agents can be hydrophilic or hydrophobic.

The calcium-sensitive fluorescent agents are loaded into the cytoplasm by contacting the cells with a solution comprising a membrane-permeable derivative of the dye. However, the loading process may be facilitated where a more hydrophobic form of the indicator is used. Thus, fluorescent indicators are known and available as hydrophobic acetoxymethyl esters, which are able to permeate cell membranes more readily than the unmodified dyes. As the acetoxymethyl ester form of the dye enters the cell, the ester group is removed by cytosolic esterases, thereby trapping the dye in the cytosol.

The fluorescence of the calcium-sensitive agent is measured by devices that detect fluorescent signals. Examples of devices that can be used include a Fluorescent Imaging Plate Reader (FLIPR) (Molecular Devices Corp., Sunnyvale, Calif.), a flow cytometer, a fluoroimeter and a fluorescent microscope.

If cells are grown on a solid support having one or multiple compartments, the fluorescence signal of the assay can be measured or detected in one or more compartments at the same time. Accordingly, a candidate modulator or blocker compound can be added to one or more compartments at a time.

A person of ordinary skill in the art will understand that control experiments for the assays described herein can be performed to facilitate analysis of the effects of the candidate N-type calcium channel modulator or blocker, or to provide a standard value to which the changes in N-type calcium channel activity can be compared. Control experiments can be performed using: (1) cells that do not express an N-type calcium channel maintained under identical conditions of the assay of the invention; (2) cells maintained under identical conditions, but without the candidate N-type calcium channel modulator or blocker compound; and/or (3) cells under identical conditions to the methods of the invention, but using known N-type calcium channel blockers.

The following is a more detailed example of the assay of the invention.

Calcium Mobilization and Electrophysiological Assay Protocols:

Cell Maintenance and Differentiation.

Unless noted otherwise, cell culture reagents were purchased from Life Technologies of Rockville, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 µg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 µM bromodeoxyuridine (Sigma). Cells were differentiated for 8 days by replacing differentiation medium every 2-3 days.

A7r5 (ATCC) cells were maintained and routinely cultured in A7r5 growth medium consisting of Dulbecco's Modified Eagles Medium containing 10% FBS, 100 U/mL penicillin, 100 μg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

FLIPR Calcium Mobilization Assay for N-Type Calcium Channel.

One day prior to performing this assay, differentiated IMR32 cells were treated with 1× CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 μM nitrendipine (Sigma), and 0.1 mL KCl dissolved in IMR32 buffer, plus Fluo-4 were added (3 μM final concentration, Molecular Probes, Eugene, Oreg.). Final test compound concentrations ranged from about 846 pM to about 17 μM, final nitrendipine concentration was 5 μM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader (FLIPR$^{96}$, Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 pM to about 17 μM, final nitrendipine concentration was 5 μM, and final KCl concentration was 90 mM. Data were collected over the entire time course and analyzed using Excel, Graph Pad Prism (version 3.02, Graph Pad, San Diego, Calif.), or Activity Base (version 5.1, IDBS, Parsippany, N.J.) software.

FLIPR Calcium Mobilization Assay for L-Type Calcium Channel.

One day prior to performing this assay, differentiated A7r5 cells were trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates were washed with A7r5 wash buffer (127 mM NaCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 μM final concentration, Molecular Probes, Eugene, Oreg.). After 1 hour, the cells were washed with 0.1 mL A7r5 wash buffer and resuspended in 0.05 mL A7r5 assay buffer that was composed of A7r5 wash buffer plus 50 μM valinomycin (Sigma). Plates were then transferred to a FLIPR$^{96}$ for assay. The FLIPR measured basal Fluo-4 fluorescence for 15 seconds, then added 0.05 mL of each compound tested diluted in A7r5 assay buffer at final concentrations ranging from about 846 pM to about 17 μM. Fluo-4 fluorescence was then measured for 5 minutes. 0.1 mL KCl agonist dissolved in A7r5 assay buffer was then added to the cells to produce a final concentration of 90 mM KCl, and fluorescence was measured for another 45 seconds. Data were collected over the entire time course and analyzed using Excel, Graph Pad Prism, or Activity Base software.

Cloning of N- and L-Type Calcium Channel Subunit Open Reading Frame cDNAs.

Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by Dubel et al. in *Proc. Natl. Acad. Sci. U.S.A* 89: 5058-5062 (1992). The beta1 subunit cDNA has been described by Pragnell et al. in *FEBS Lett.* 291: 253-258 (1991). The beta3 subunit cDNA has been described by Castellano et al. in *J. Biol. Chem.* 268: 12359-12366 (1993). The alpha2delta subunit cDNA has been described by Kim et al. in *Proc. Natl. Acad. Sci. U.S.A.* 89: 3251-3255 (1992). The alpha1c subunit cDNA has been described by Koch et al. in *J. Biol. Chem.* 265: 17786-17791 (1990).

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "6+A ASFMG ΔET" according to the nomenclature of Lin et al. (*Neuron* 18: 153-166 (1997)). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen).

The 1.8 kb cDNA encoding the β1 subunit, the 1.45 cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the α2δ cDNA amplification. PCR products were subcloned and fully sequenced on both strands. Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST.

Sequences around the recombinogenic region were sequenced to confirm accurate recombination into the expression vector.

TABLE 1

| PRIMER SEQUENCE | SEQ ID NO. |
|---|---|
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-Type Recombinant Cell Line Development.

N-type calcium channel expressing HEK-293 cells were created in two stages. Stage 1 was created as follows. The rat α1b, and β3 cDNA expression constructs (2.5 µg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 µg/mL blasticidin and 500 µg/mL geneticin, and incubated for 3 weeks at 37° C., 5% $CO_2$, 95% humidity. Plates containing ≤1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 µM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base software. The clone with the greatest signal-to-noise, best stability of response with passage number, and best adhesion to PDL precoated plates (Becton Dickinson) was expanded, characterized and used for stage 2 cell line development.

Stage 2 of N-type cell line development was carried out as follows. The rat α2δ1 cDNA expression construct (5 µg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 µg/mL blasticidin, 500 µg/mL geneticin, and 250 µg/mL zeocin and incubated for 3 weeks at 37° C., 5% $CO_2$, 95% humidity. Plates containing ≤1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

N-Type Electrophysiology.

For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (Hamill et al., *Pfluegers Arch.* 391: 85-100 (1981)) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-µs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2$GTP (0.5 mM), and adjusted to pH 7.2 with CsOH. The pipette resistance ranged from 2 to 3 MOhm and was compensated by 75-80% by the built-in electronic circuitry.

Currents were elicited by stepping from holding potential of −90 mV to 0 mV for 20 ms every 10 sec. At the −90 mV membrane voltage a proportion of channels was in the inactivated state, and thus contact with a blocker would involve interaction with both resting and inactivated channels. This protocol was used as a first tier screen. For dissection of two components of inhibition (resting block with the apparent dissociation constant $K_r$ and inactivated state block with $K_i$), steady-state inactivation curves were collected using a double-pulse protocol. Three-second long depolarizing pre-pulse incrementing in 10 mV steps was followed by a 10 ms test pulse to 0 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned ~1 mm apart from the cell.

All curve fittings were carried out using Origin software (version 5.0, Microcal). A Hill equation was used to fit the concentration-response curves and to determine $IC_{50}$ values. A Boltzman equation was used to fit inactivation curves, returning half-inactivation voltage, $V_{0.5}$, slope p and the amplitude of current at the most negative voltage where eventually all channels were in resting state. These parameters were used to calculate the apparent dissociation constants: $K_r=((Ab/Ac)/(1-(Ab/Ac))*[b])$ where [b] is the drug concentration, Ac is the maximum test current amplitude in control conditions and Ab is the maximum test current amplitude in the presence of a blocker; $K_i=[b]/((exp(-(dx/p))*(1+([b]/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (10% Tween-80) as control. Fifteen minutes after the i.p. dosing, and 30 minutes after the p.o. dosing mice are injected with formalin (20 µL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (Kim and Chung, *Pain* 50: 355-363 (1992)). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertibral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia:

Sensitivity to non-noxius mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to mammal, e.g. human, orally at a dose of from about 0.0025 to about 1500 mg per kg body weight of the mammal, or an equivalent amount of a pharmaceutically acceptable salt thereof, per day to treat the particular disorder. A useful oral dose of a compound of the present invention administered to a mammal is from about 0.0025 to about 50 mg per kg body weight of the mammal, or an equivalent amount of the pharmaceutically acceptable salt thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily as one or more tablets, each containing from about 0.01 to about 50 mg of the compound, or an equivalent amount of a pharmaceutically acceptable salt or solvate thereof.

In one embodiment, a pharmaceutical composition of the present invention can be administered orally and is formulated into tablets, dragees, capsules or an oral liquid preparation.

Alternatively, a pharmaceutical composition of the present invention can be administered rectally, and is formulated in suppositories.

Alternatively, a pharmaceutical composition of the present invention can be administered by injection.

A pharmaceutical composition of the present invention can contain from about 0.01 to 99 percent by weight, and preferably from about 0.25 to 75 percent by weight, of active compound(s).

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by parenteral, subcutaneous, intravenous, intramuscular, intraperitoneal, transdermal, or buccal route. Alternatively, or concurrently, administration can be by the oral route. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

A pharmaceutical composition of the present invention is preferably manufactured in a manner which is itself known, for example, by means of conventional mixing, granulating, dragee-making, dissolving, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

(2S) N-[1-(4-Methyl-2-methylaminopentanoyl)piperidin-4-yl]-3-trifluoromethylbenzenesulfonamide fumarate (4)

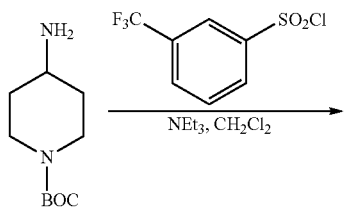

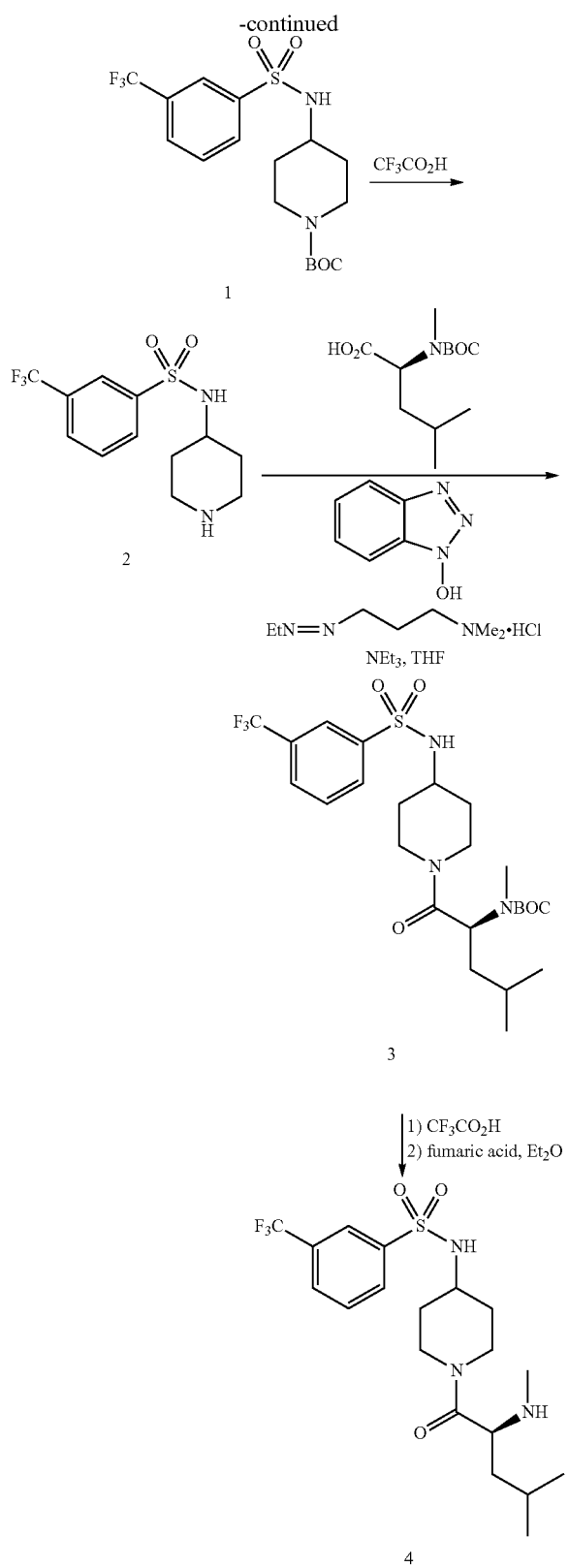

dichloromethane (50 mL). 3-Trifluoromethylbenzenesulfonyl chloride (3.64 mL, 22.72 mmol) was added and the mixture was stirred for 2 hours. The solvent was removed in vacuo, and the residue was partitioned between ice cold 1M hydrochloric acid (500 mL) and ether (500 mL), and the organic phase was separated, dried (MgSO$_4$) and the solvent evaporated to dryness in vacuo to give the title compound 1 as a white solid (9 g, 100%). LC: 100%. MS: m/z=438.1 (M+Na).

b) N-Piperidin-4-yl-3-trifluoromethylbenzenesulfonamide (2): 4-(3-Trifluoromethylbenzenesulfonylamino)piperidine-1-carboxylic acid tert-butyl ester (1) (9.0 g, 22.04 mmol) was dissolved in trifluoroacetic acid (20 mL) with stirring and the mixture was stirred at room temperature for 4 hours. The mixture was diluted with water (300 mL) and extracted with ether (300 mL) which was discarded. The aqueous phase was carefully basified to pH 10 using potassium carbonate, and extracted with ethyl acetate (2×300 mL), dried (MgSO$_4$), and the solvent was evaporated to dryness in vacuo to give the title compound 2 as a white solid (6.3 g, 93%). LC: 87%. MS; m/z=309.2 (M+H).

c) (2S) Methyl-{3-methyl-1-[4-(3-trifluoromethylbenzene-sulfonylamino)piperidine-1-carbonyl]-butyl}carbamic acid tert-butyl ester (3): N-Piperidin-4-yl-3-trifluoromethylbenzenesulfonamide (2) (6.3 g, 20.4 mmol), 1-hydroxybenzotriazole (3.32 g, 24.52 mmol), N-ethyl-dimethylaminopropyl carbodiimide hydrochloride (EDCI) (4.7 g, 24.52 mmol), and N—BOC—N-methylleucine (5.5 g, 22.44 mmol) were suspended in dry tetrahydrofuran (100 mL). Triethylamine (TEA) (8.5 ml, 61.2 mmol) was added to the suspension and the mixture stirred overnight. The mixture was poured into 1M sodium hydroxide solution (300 mL) and extracted with ethyl acetate (2×300 mL), dried (MgSO$_4$), and the solvent was evaporated to dryness in vacuo to leave an off-white solid. The solid was triturated with ether (100 mL) to give the title compound 3 (yield 10.35 g, 95%) as a white solid. $^1$H NMR (400 MHz, CDCl$_3$): δ (2:1 mixture of rotamers) 8.15 (1H, s), 8.07 (1H, d, J=12 Hz), 7.85 (1H, d, J=12 Hz), 7.66 (1H, m), 5.05-3.8 (4H, m), 3.55 (1H, m), 3.20-2.90 (1H, m), 2.65 (2s, 3H), 2.90-2.57 (1H, m), 1.74 (2H, m), 1.70-1.10 (15H, m), 0.90 (6H, d, J=15 Hz). LC: 100%. MS: m/z=558.3 (M+Na).

d) (2S) N-[1-(4-Methyl-2-methylaminopentanoyl)piperidin-4-yl]-3-trifluoromethylbenzenesulfonamide fumarate (4): Methyl-{3-methyl-1-[4-(3-trifluoromethylbenzene-sulfonylamino)piperidine-1-carbonyl]-butyl}-carbamic acid tert-butyl ester (3) (1.0 g, 1.87 mmol) was dissolved in trifluoroacetic acid (5 mL) and the mixture was stirred at room temperature for 3 hours. The mixture was diluted with water (100 mL) and extracted with ether (2×100 mL) which was discarded. The aqueous phase was basified with potassium carbonate to pH 10 and extracted with dichloromethane (2×100 ml), dried (MgSO$_4$), and the solvent evaporated to dryness in vacuo to leave a colourless foam (679 mg, 1.56 mmol). This foam was dissolved in ether (25 ml) and fumaric acid (181 mg, 1.56 mmol) in methanol (2 mL) was added to the mixture. The mixture was filtered and the product dried in vacuo to give the title compound as a white solid (680 mg, 66%). LC: 98.1%. $^1$H NMR (400 MHz, CDCl$_3$): δ 8.18 (1H, s), 8.10 (1H, d, J=6.8 Hz), 7.86 (1H, t, J=6.8 Hz), 7.70 (1H, m), 6.75 (2H, s), 4.40-4.20 (1H, m), 4.17-4.03 (1H, m), 3.43-

2.75 (4H, m), 2.55 and 2.45 (2s, 3H), 1.95-1.37 (7H, m), 0.96 (6H, m). MS (e/z): 513 (M+H⁺).

Example 2

Alkylation Conditions of the Sulfonamide (3) of Example 1

Method A

Scheme 9

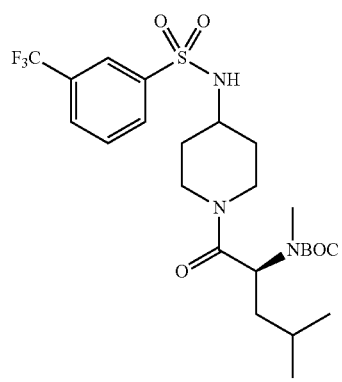

1) ROH, PPh₃,
   ⁱPrO₂CN=NCO₂ⁱPr
   THF
2) CF₃CO₂H
3) Fumaric acid, Et₂O
→ METHOD A

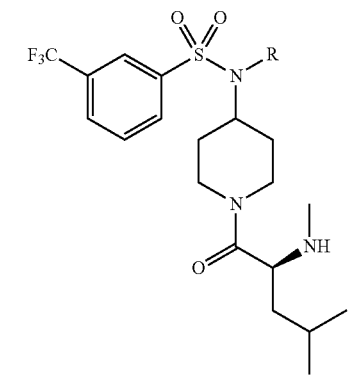

Methyl-{3-methyl-1-[4-(3-trifluoromethylbenzenesulfonylamino)-piperidine-1-carbonyl]butyl}carbamic acid tert-butyl ester (3) (1.0 g, 1.87 mmol), and triphenylphosphine (0.59 g, 2.24 mmol) were dissolved in dry tetrahydrofuran (10 mL). The alcohol ROH (2.24 mmol) was added to the mixture followed by diisopropyl azodicarboxylate (0.44 mL, 2.24 mmol) and the mixture was stirred for 24 hours at 50° C. The solvent was removed in vacuo and the residue was chromatographed over flash silica eluting with hexanes:ethyl acetate (3:1) to give the BOC protected product as a colourless gum. This material was dissolved in trifluoroacetic acid (6 mL) and gently heated to about 50° C. for 5 minutes. The mixture was partitioned between water (50 mL) and ether (50 mL) and the aqueous phase was separated. The aqueous phase was basified with potassium carbonate to pH 10, extracted with ethyl acetate (2×50 ml), dried (MgSO₄), and the solvent was evaporated to dryness in vacuo to give a gum. This gum was chromatographed over flash silica eluting with ethyl acetate:methanol:ammonia (200:40:4) to give the free base as a colourless gum. This was dissolved in ethyl acetate (5 ml) and fumaric acid (1 mol eq.) in methanol (1 mL) was added to the mixture. The solvent was evaporated to dryness in vacuo and the residue was triturated with ether to give the fumarate salt as a white solid.

Method B

Scheme 10

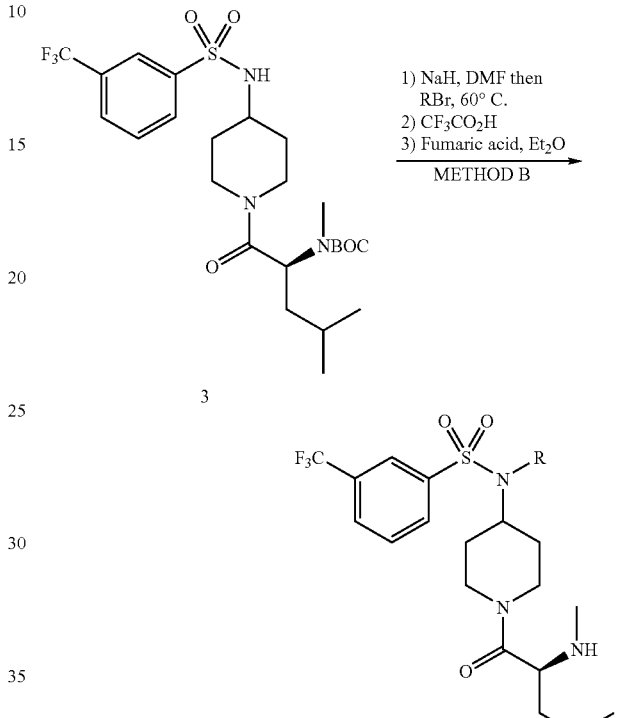

1) NaH, DMF then RBr, 60° C.
2) CF₃CO₂H
3) Fumaric acid, Et₂O
→ METHOD B

To a suspension of sodium hydride 95% dispersion in mineral oil in dry DMF (5 mL) under argon was added methyl-{3-methyl-1-[4-(3-trifluoromethylbenzenesulfonylamino)piperidine-1-carbonyl]butyl}carbamic acid tert-butyl ester (3) (0.93 mmol) all at once, and the mixture was stirred for 2 hours at 70° C. The alkyl bromide RBr (1.12 mmol) was added to the mixture and the reaction mixture was heated to 100° C. for 48 hours. The reaction mixture was quenched with methanol (5 mL) and the solvent was evaporated to dryness in vacuo. The residue was treated with trifluoroacetic acid (4 mL) with stirring for 4 hours. The mixture was partitioned between ether (50 mL) and 1M hydrochloric acid (50 mL) and the aqueous phase was separated. The aqueous phase was basified to pH 10 using potassium carbonate, extracted with ethyl acetate (2×50 mL), dried (MgSO₄) and the solvent was evaporated to dryness in vacuo. The residue was chromatographed over flash silica eluting with ethyl acetate:methanol:ammonia (250:40:4) to give the free base. This base was dissolved in dichloromethane (5 mL) and hydrogen chloride in dioxane 4M (1 mL) was added to the mixture. The mixture was evaporated to dryness in vacuo and the residue was triturated with ether (20 mL) to give the hydrochloride salt as a white solid.

Alternatively the fumarate salt was prepared as follows. The free base was dissolved in ether (20 mL) and fumaric acid (1 mol equivalent) in methanol (1-2 mL) was added. The solvent was evaporated to dryness in vacuo and the residue was triturated with ether (5-10 mL) to give the fumarate salt as a white solid. The following compounds were prepared by the above methods:

a) (2S) N-Methyl-N-[1-(4-methyl-2-methylaminopentanoyl)-piperidin-4-yl]-3-trifluoromethylbenzenesulfonamide fumarate (5): Methyl-{3-methyl-1-[4-(3-trifluoromethylbenzenesulfonylamino)piperidine-1-carbonyl]butyl}carbamic acid tert-butyl ester (3) (0.5 g, 0.93 mmol) was alkylated with iodomethane using method B. The free base (300 mg) was converted to the fumarate salt using method B to give the title compound (5) (305 mg, 59%) as a white solid. LC: 100%. MS: m/z=450.2, 451.2 (M+H). $^1$H NMR (400 MHz, CDCl$_3$): 6 (1:1 mixture of rotamers) 8.09 (1H, s), 8.02 (1H, m), 7.86 (1H, d, J=7.5 Hz), 7.72 (1H, t, J=7.5 Hz), 7.6-6.9 (2H, bs, CO$_2$H), 6.77 (2H, s), 4.75 (1H, d, J=13 Hz), 4.06 (1H, m), 4.96 (1H, d, J=13 Hz), 3.62-3.75 (1H, m), 3.10 (1H, m), 2.78 (3H, s), 2.55 (1H, m), 2.40, 2.32 (3H, 2s), 1.85-1.30 (7H, m), 0.92 (6H, m).

b) (2S) N-Isopropyl-N-[1-(4-methyl-2-methylaminopentanoyl)-piperidin-4-yl]-3-trifluoromethylbenzenesulfonamide fumarate (6): Methyl-{3-methyl-1-[4-(3-trifluoromethylbenzenesulfonylamino)piperidine-1-carbonyl]butyl}-carbamic acid tert-butyl ester (3) (1.0 g, 1.87 mmol) was alkylated with isopropanol using Mitsunobu conditions, method A. The product was chromatographed (hexane:ethyl acetate 4:1), TLC (SiO$_2$, ethyl acetate:hexane 1:4, Rf=0.14). The purified product was treated with trifluoroacetic acid (6 ml) for 5 minutes at 50° C. The mixture was worked up using conditions A and purified by flash chromatography ethyl acetate:methanol:ammonia (250:40:4) to give the free base (123 mg) as a foam. This was converted to the fumarate salt (conditions A) to give the title compound (6) (120 mg, 10%) as a white solid. LC: 100%. MS (m/z): 478.2, 479.2 (M+H). $^1$H NMR (400 MHz, DMSO-d$_6$): δ 8.18 (1H, d, J=7.5 Hz), 8.06 (2H, m), 7.87 (1H, t, J=7.5 Hz), 6.52 (2H, s), 4.48 (1H, m), 3.96 (1H, d, J=13 Hz), 3.92-3.60 (4H, m), 3.15 (1H, m), 2.65 (1H, m), 2.28 and 2.20 (3H, 2s), 2.05-1.85 (2H, m), 1.80-1.55 (3H, m), 1.35 (2H, m), 1.12 (6H, m), 0.86 (6H, m). TLC (SiO$_2$, ethyl acetate: methanol; ammonia 250:40:4) Rf=0.12 detection U.V.

Similarly, (2S) N-1-butyl-N-[1-(4-methyl-2-methylaminopentanoyl)-piperidin-4-yl]-3-trifluoromethylbenzenesulfonamide was prepared. LC: 80.9%. MS (m/z): 492.3, 493.4 (M+H$^+$), 494.2 (M+2H$^+$). $^1$H NMR (400 MHz, CD$_3$OD): δ 8.16 (1H, m), 8.13 (1H, m), 8.00 (1H, d, J=7.2 Hz), 7.84 (1H, m), 4.42 (1H, m), 3.92 (2H, m), 3.22 (1H, m), 3.06 (2H, m), 2.67 (4H, m), 2.00 (1H, m), 1.69 (8H, m), 0.99 (12H, m).

c) (2S) N-Cyclopropylmethyl-N-[1-(4-methyl-2-methylamino-pentanoyl)piperidin-4-yl]-3-trifluoromethylbenzenesulfonamide fumarate (7): Methyl-{3-methyl-1-[4-(3-trifluoromethylbenzenesulfonylamino)piperidine-1-carbonyl]butyl}carbamic acid tert-butyl ester (3) (0.5 g, 0.93 mmol) was alkylated with cyclopropylmethyl bromide using method B. The product was treated with trifluoroacetic acid and worked up according to method B. Flash chromatography (SiO$_2$, ethyl acetate:methanol:ammonia 250:20:2) gave the free base as a colourless gum (88 mg). This gum was converted to the fumarate salt to give the title compound (7) (80 mg, 14%) as a white solid. TLC (SiO$_2$, ethyl acetate: methanol: ammonia, 250:40:4): Rf=0.31 (detection UV and potassium iodoplatinate). LC: 100%. MS (m/z): 490.2, 491.2 (M+H). $^1$H NMR (400 MHz, DMSO-d$_6$): δ 8.20 (1H, d, J=7 Hz), 8.12 (1H, s), 8.07 (1H, d, J=7 Hz), 7.85 (1H, t, J=7 Hz), 6.56 (1H, s), 4.45 (1H, m), 4.00-3.05 (5H, m), 2.65 (2H, m), 2.30 and 2.22 (3H, 2s), 1.73-1.48 (5H, m), 1.35 (2H, m), 0.95 (1H, m), 0.85 (6H, m), 0.45 (2H, m), 0.25 (2H, m).

d) (2S) N-Cyclopentyl-N-[1-(4-methyl-2-methylaminopentanoyl)piperidin-4-yl]-3-trifluoromethylbenzenesulfonamide fumarate (8): Methyl-{3-methyl-1-[4-(3-trifluoromethylbenzenesulfonylamino)piperidine-1-carbonyl]butyl}-carbamic acid tert-butyl ester (3) (1.0 g, 1.87 mmol) was alkylated with cyclopentanol using Mitsunobu conditions, method A. The product was chromatographed using hexane:ethyl acetate (3:1) to give BOC-protected material (150 mg). This material was treated with trifluoroacetic acid (4 mL) at 40° C. for 20 minutes. The reaction mixture was worked up using method A conditions, then chromatographed using ethyl acetate:methanol:ammonia (200:40:4) to give the free base (106 mg). This base was converted to the fumarate salt to give the title compound (8) (100 mg, 18%) as a white solid. LC: 100%. MS (m/z): 504.3, 505.4 (M+H). $^1$H NMR (400 MHz, DMSO-d$_6$): δ 8.16 (1H, d, J=7.5 Hz), 8.07 (2H, m), 7.86 (1H, t, J=7.5 Hz), 6.57 (2H, s), 4.45 (1H, m), 4.08-3.86 (4H, m), 3.57 (1H, m), 3.15 (1H, m), 2.67 (1H, m), 2.36 and 2.30 (3H, 2s), 1.95 (2H, m), 1.75-1.35 (14H, m), 0.90 (6H, m).

e) (2S) N-[1-(4-Methyl-2-methylaminopentanoyl)piperidin-4-yl]-N-(tetrahydrofuran-3-yl)-3-trifluoromethylbenzenesulfonamide fumarate (9): Methyl-{3-methyl-1-[4-(3-trifluoromethylbenzenesulfonylamino)piperidine 1-carbonyl]butyl}-carbamic acid tert-butyl ester (3) (1.0 g, 1.87 mmol) was alkylated with 3-hydroxy-tetrahydrofuran using Mitsunobu conditions, method A. The reaction mixture was chromatographed twice using hexane:ethyl:acetate (2:1) to give the BOC protected material (75 mg), TLC SiO$_2$ (hexane:ethyl acetate 2:1, Rf=0.31), detection UV. This material was stirred with trifluoroacetic acid (4 mL) at 40° C. for 20 minutes. The mixture was worked up and chromatographed (method A) to give the free base (46 mg). This base was converted to the fumarate salt to give the title compound (9) (48 mg, 8%) as a white solid. LC: 100%. MS: 506.2, 507.3 (M+H). $^1$H NMR (400 MHz, DMSO-d$_6$): δ 8.17 (1H, d, J=7.5 Hz), 8.08 (2H, m), 7.87 (1H, t, J=7.5 Hz), 6.53 (2H, s), 4.45 (2H, m), 3.93 (2H, m), 3.78-3.50 (6H, m), 2.38 and 2.30 (3H, 2s), 2.13-1.83 (4H, m), 1.80-1.57 (3H, m), 1.33 (2H, m), 1.88 (6H, m).

f) (2S) 2-[[1-(4-Methyl-2-methylaminopentanoyl)piperidin-4-yl]-(3-trifluoromethylbenzenesulfonyl)amino]acetamide hydrochloride (10): Methyl-{3-methyl-1-[4-(3-trifluoromethylbenzenesulfonylamino)piperidine-1-carbonyl]butyl}carbamic acid tert-butyl ester (3) (1.0 g, 1.87 mmol) was alkylated with 2-bromoacetamide using the conditions of method B. The BOC protecting group was removed using trifluoroacetic acid, the product chromatographed over flash silica eluting with ethyl acetate; methanol: ammonia (250:40: 4) to give the free base. This base was converted to the hydrochloride salt to give the title compound (10) (170 mg, 30%) as a white solid. TLC (SiO$_2$, ethyl acetate: methanol: ammonia, 250:40:4): Rf=0.22; detection UV, Dragendorff's reagent. LC: 100%. MS (m/z): 493.2, 494.2 (M+H). $^1$H NMR (400 MHz, CDCl$_3$): (mixture of rotamers) δ 9.6-8.9 (2H, bs), 8.32 (1H, s), 8.22 (1H, d, J=8.8 Hz), 7.85 (1H, d, J=8.8 Hz), 7.70 (1H, t, J=8.8 Hz), 7.30 (1H, bs), 6.90 (1H, bs), 4.60 (1H, bd, J=13 Hz), 4.25 (3H, m), 4.05-3.8 (2H, m), 3.06 (1H, t, J=13 Hz), 2.75 (3H, s), 2.53 (1H, t, J=13 Hz), 2.20 (1H, m), 1.95-1.65 (6H, m), 0.93 (6H, m).

g) (2S) N-(2-Hydroxyethyl)-N-[1-(4-methyl-2-methylamino-pentanoyl)piperidin-4-yl]-3-trifluoromethylbenzenesulfonamide hydrochloride (11): Methyl-{3-methyl-1-[4-(3-trifluoromethylbenzenesulfonylamino)-piperidine-1-carbonyl]butyl}carbamic acid tert-butyl ester (3) (1.0 g, 1.87 mmol) was alkylated with 2-bromoethanol using the conditions of method B. The BOC protecting group was removed using trifluoroacetic acid, the product chromatographed over flash silica eluting with ethyl acetate; methanol:ammonia (250:40:4) to give the free base. This base was converted to the hydrochloride salt to give the title compound (11) (65 mg, 11%) as a white solid. TLC (SiO$_2$, ethyl acetate: methanol: ammonia, 250:40:4): Rf=0.26; detection UV; Dragendorff's reagent. LC: 100%. MS (m/z): 480.2 (M+H), 502.2 (M+Na). $^1$H NMR (400 MHz, CDCl$_3$): (mixture of rotamers) δ 9.90 (1H, bs), 9.35 (1H, bs), 8.13 (1H, s), 8.06 (1H, d, J=9.0 Hz), 7.84 (1H, d, J=9.0 Hz), 7.70 (1H, t, J=9.0 Hz), 4.61 (1H, m), 4.10-3.70 (6H, m), 3.45 (2H, m), 3.30-3.05 (2H, m), 2.75-2.40 (7H, m), 1.95-1.45 (6H, m), 0.97 (6H, m).

h) (2S) N-(2-Methanesulfonylaminoethyl)-N-[1-(4-methyl-2-methylaminopentanoyl)piperidin-4-yl]-3-trifluoromethylbenzenesulfonamide fumarate (12): Methyl-{3-methyl-1-[4-(3-trifluoromethyl-benzenesulfonylamino)piperidine-1-carbonyl]butyl}carbamic acid tert-butyl ester (3) (1.0 g, 1.87 mmol) was alkylated with N-(2-bromoethyl)-methanesulfonamide using the conditions of method B. The BOC protecting group was removed using trifluoroacetic acid, the product was chromatographed over flash silica eluting with ethyl acetate:methanol:ammonia (250:40:4) to give the free base. This base was converted to the fumarate salt to give the title compound (12) (190 mg, 30%) as a white solid. TLC (SiO$_2$, ethyl acetate: methanol: ammonia, 250:40:4): Rf=031; detection UV; Dragendorff's reagent. LC: 100%. MS (m/z): 557.3, 558.3 (M+H), 579.2 (M+Na). $^1$H NMR (400 MHz, DMSO-d$_6$): (mixture of rotamers) δ 8.22 (1H, d, J=10 Hz), 8.15 (1H, s), 8.10 (1H, d, J=10 Hz), 7.89 (1H, t, J=10 Hz), 7.24 (1H, m), 6.55 (2H, s), 4.44 (1H, d, J=12 Hz), 4.02-3.75 (6H, m), 2.91 (3H, s), 2.70-2.55 (2H, m), 2.25 (3H, 2s), 1.75-1.28 (7H, m), 0.86 (6H, m).

Example 3

N-Cyclopropyl-N-piperidin-4-yl-3-trifluoromethyl-benzenesulfonamide (14)

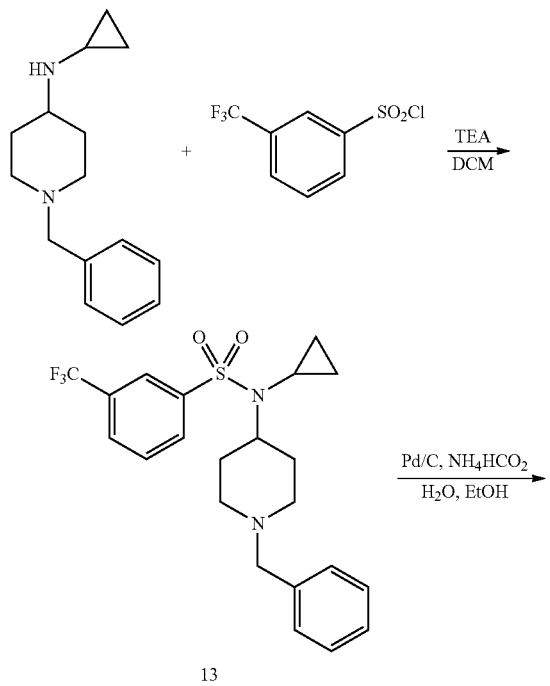

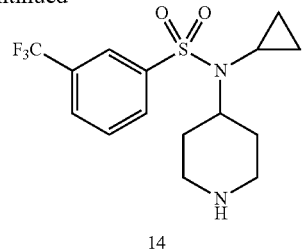

14 a) N-(1-Benzylpiperidin-4-yl)-N-cyclopropyl-3-trifluoromethyl-benzenesulfonamide (13): N-Benzyl-4-cyclopropylaminopiperidine (5.0 g, 21.71 mmol) and triethylamine (3.6 mL, 26.05 mmol) were dissolved in dichloromethane (DCM, 100 mL). 3-Trifluoromethylbenzenesulfonyl chloride (3.47 mL, 21.71 mmol) was added and the resulting reaction mixture was stirred overnight. The mixture then was poured into potassium carbonate solution (200 mL), extracted with ether (2×200 mL), dried (MgSO$_4$), and concentrated in vacuum to give a crude product as a yellow gum, which was purified by column chromatography on silica gel (hexane/EtOAc, 2:1). The title compound 13 was obtained (9 g, 95% yield) as a pale yellow gum. Rf=0.42 (UV detection).

b) N-Cyclopropyl-N-piperidin-4-yl-3-trifluoromethyl-benzenesulfonamide (14): N-(1-benzylpiperidin-4-yl)-N-cyclopropyl-3-trifluoromethylbenzenesulfonamide (13) (9.0 g, 20.52 mmol) was dissolved in ethanol (100 mL). Water (10 mL) was added to the mixture, followed by ammonium formate (12.94 g, 205.20 mmol) and 10% palladium on charcoal (1.0 g). The mixture was heated under reflux for 2 hours. The mixture was cooled and filtered through celite. The filtrate was concentrated in vacuum to give a colorless residue, which was partitioned between ethyl acetate (250 mL) and potassium carbonate solution (250 mL). The organic phase was separated, dried (MgSO4), and concentrated to give a white solid, which was triturated with hexane (100 mL) to give the desired product 14 as a white solid (6.0 g, 84% yield). LC: 100%. $^1$H NMR (CDCl$_3$): δ 8.15 (1H, s), 8.07 (1H, d, J=7.9, Hz), 7.85 (1H, d, J=7.9 Hz), 7.69 (1H, t, J=7.9 Hz), 3.95 (1H, tt, J=8.0, 3.8 Hz), 3.10 (2H, dd, J=12.2, 3.8 Hz), 2.62 (2H, dt, J=10.0, 2.2 Hz), 1.98 (1H, m), 1.83 (2H, dq, J=12.2, 4.1 Hz), 1.62-1.50 (4H, m), 1.00 (2H, m), 0.78 (2H, m). MS: m/z=349.2, 350.2 (M+H). TLC (SiO$_2$, ethyl acetate: methanol: ammonia, 250:10:1): Rf=0.30.

Example 4

N-Cyclopropyl-N-[1-(naphth-2-ylmethyl)piperidin-4-yl]-benzenesulfonamide (15)

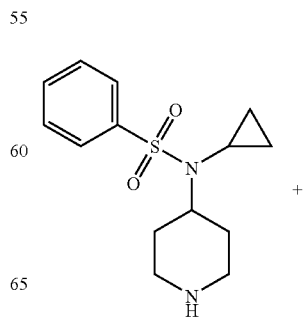

+

-continued

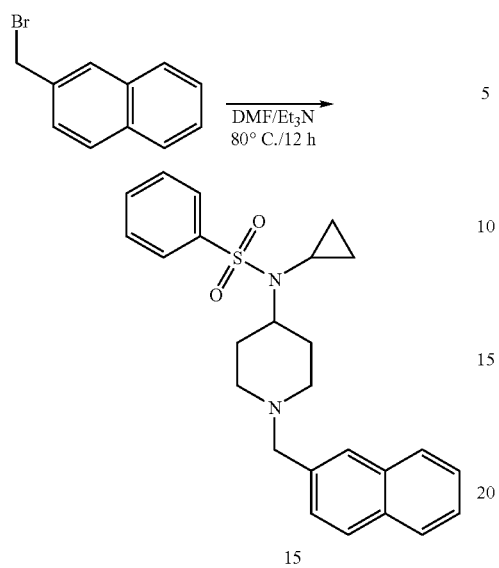

15

N-Cyclopropyl-N-piperidin-4-yl-benzenesulfonamide (56 mg, 0.2 mmol) was dissolved in DMF (2.5 ml) and triethylamine (75 µL, 54 mg, 0.54 mmol) added, followed by 2-bromomethyl-naphthalene (88 mg, 0.4 mmol). The reaction mixture was stirred for 12 hours at 80° C. and then the solvent was evaporated. The residue was purified by flash chromatography to give 12.8 mg of the desired product N-cyclopropyl-N-[1-(naphth-2-ylmethyl)-piperidin-4-yl]benzenesulfonamide (15). $^1$H NMR (CDCl$_3$): δ 8.06-7.71 (m, 7H), 7.61-7.44 (m, 5H), 3.94-3.84 (m, 1H), 3.68 (S, 2H), 3.01-2.94 (m, 2H), 2.18-1.94 (m, 5H), 1.58-1.49 (m, 2H), 1.02-0.96 (m, 2H), 0.81-0.74 (m, 2H). MS (EI): m/z 421 (M+H$^+$).

Example 5

N-Cyclopropyl-N-[1-(4-phenylbenzyl)piperidin-4-yl]-benzenesulfonamide (16)

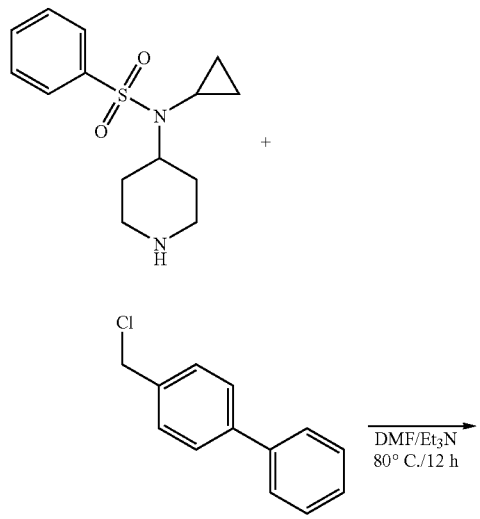

-continued

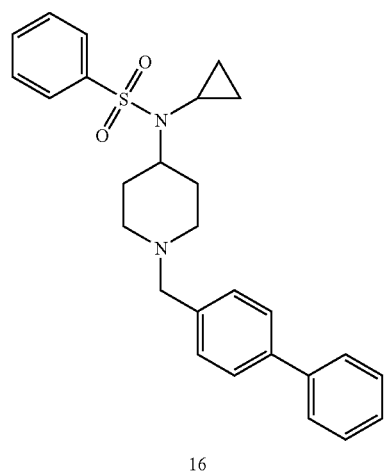

16

N-Cyclopropyl-N-piperidin-4-yl-benzenesulfonamide (56 mg, 0.2 mmol) was dissolved in DMF (2.5 ml) and triethylamine (75 µL, 54 mg, 0.54 mmol) added, followed by 4-chloromethyl-biphenyl (81 mg, 0.4 mmol). The reaction mixture was stirred for 12 hours at 80° C. and the solvent was evaporated. The residue was purified by flash chromatography to give 16.4 mg of the desired product N-cyclopropyl-N-[1-(4-phenylbenzyl)piperidin-4-yl]benzenesulfonamide (16). $^1$H NMR (CDCl$_3$): δ 7.92-7.85 (m, 1H), 7.63-7.31 (m, 9H), 7.30-7.25 (m, 4H), 3.93-3.83 (m, 1H), 3.54 (s, 2H), 3.00-2.89 (m, 2H), 2.14-1.89 (m, 5H), 1.66-1.49 (m, 2H+H$_2$O), 1.04-0.97 (m, 2H), 0.81-0.72 (m, 2H). LC: 98%. MS (EI): m/z 447 (M+H$^+$).

Example 6

N-Cyclopropyl-N-[1-(4-isopropylbenzyl)piperidin-4-yl]-benzenesulfonamide (17)

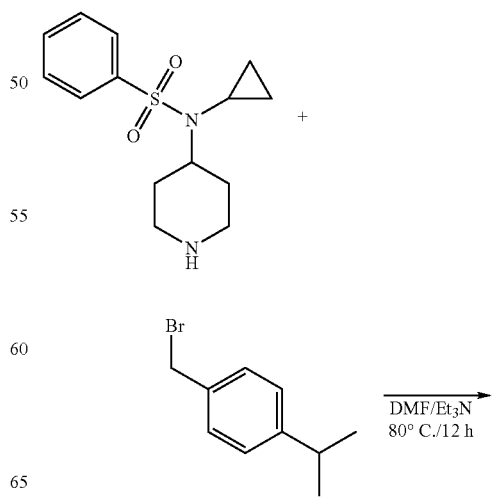

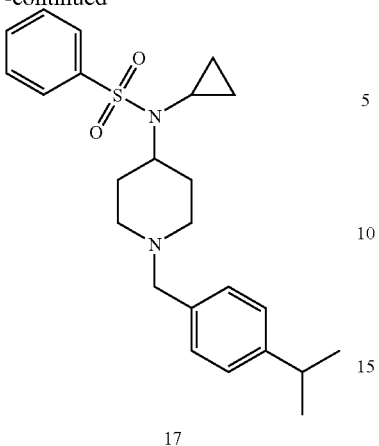

17

N-Cyclopropyl-N-piperidin-4-yl-benzenesulfonamide (100 mg, 0.36 mmol) was dissolved in DMF (2.5 mL) and triethylamine (75 μL, 54 mg, 0.54 mmol) added, followed by 1-bromomethyl-4-isopropylbenzene (83.5 mg, 0.39 mmol). The reaction mixture was stirred for 12 hours at 80° C. and then the solvent was evaporated. The residue was purified by flash chromatography to give 29 mg of the title compound 17 as a yellow oil. $^1$H NMR (CDCl$_3$): δ 7.88-7.83 (m, 2H), 7.59-7.47 (m, 3H), 7.21-7.14 (m, 4H), 3.89-3.78 (m, 1H), 3.45 (s, 2H), 2.95-2.88 (m, 3H), 2.03-1.84 (m, 5H), 1.51-1.44 (m, m, 2H), 1.23 (d, 6H, J=7.01 Hz), 1.01-0.93 (m, 2H), 0.79-0.69 (m, 2H). LC: 100%. MS (EI): m/z 413 (M+H$^+$).

Similarly, N-cyclopropyl-N-[1-(4-dimethylaminobenzyl)piperidin-4-yl]-3-trifluoromethylbenzenesulfonamide was prepared from N-cyclopropyl-N-piperidin-4-yl-3-trifluoromethylbenzenesulfonamide and 1-bromomethyl-4-dimethylaminobenzene.

Also, N-cyclopropyl-N-[1-(4-tert-butylbenzyl)piperidin-4-yl]-benzenesulfonamide was prepared from N-cyclopropyl-N-piperidin-4-yl-benzenesulfonamide and 1-bromomethyl-4-tert-butylbenzene. LC: 100%, MS: m/z=427.2, 428.3 (M+H$^+$). $^1$H NMR (400 MHz, CDCl$_3$): δ 7.85 (2H, m), 7.56 (1H, m), 7.50 (2H, m), 7.32 (2H, d, J=8.4 Hz), 7.19 (2H, d, J=8.4 Hz), 3.85 (1H, m), 3.44 (2H, s), 2.89 (1H, s), 2.87 (1H, s), 1.97 (5H, m), 1.59 (4H, s), 1.49 (1H, s), 1.47 (1H, s), 1.32 (9H, s), 0.97 (2H, m), 0.75 (2H, m).

Example 7

N-Cyclopropyl-N-[1-(3-trifluoromethyl-4-methoxybenzyl)piperidin-4-yl]-3-trifluoromethylbenzenesulfonamide (18)

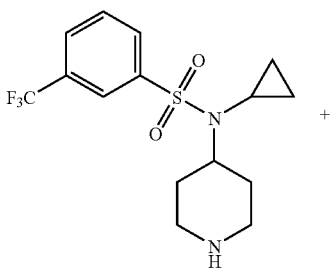

14

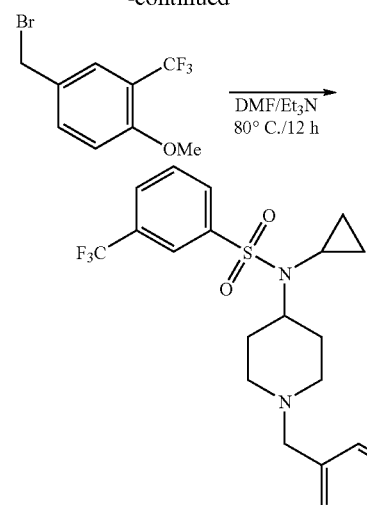

18

N-Cyclopropyl-N-piperidin-4-yl-3-trifluoromethylbenzenesulfonamide (200 mg, 0.57 mmol) was dissolved in DMF (4 mL) and triethylamine (200 μL, 1.43 mmol) added, followed by 4-bromomethyl-1-methoxy-2-trifluoromethyl-benzene (154 mg, 0.57 mmol). The reaction mixture was stirred for 12 hours at 80° C. and then the solvent was evaporated. The residue was purified by flash chromatography to give 244 mg of the title compound 18 as a yellow solid. $^1$H NMR (CDCl$_3$): δ 8.14-8.11 (m, 1H), 8.07-8.03 (m, 1H), 7.86-7.80 (m, 1H), 7.70-7.64 (m, 1H), 7.50-7.47 (m, 1H), 7.42-7.37 (m, 1H), 6.96-6.91 (m, 1H), 3.93-3.79 (m, 4H), 3.42 (s, 2H), 2.91-2.80 (m, 2H), 2.03-1.85 (m, m, 5H), 1.53-1.44 (m, 2H), 1.02-0.96 (m, 2H), 0.83-0.76 (m, 2H). LC: 100%. MS (EI): m/z 537 (M+H$^+$).

Similarly, N-cyclopropyl-N-[1-(3-trifluoromethyl-4-methoxybenzyl)-piperidin-4-yl]benzenesulfonamide was prepared from N-cyclopropyl-N-piperidin-4-yl-benzenesulfonamide. LC: 98%. MS: m/z=469.2, 470.1 (M+H$^+$). $^1$H NMR (400 MHz, CDCl$_3$): δ 7.86 (2H, m), 7.57 (1H, m), 7.49 (3H, m), 7.39 (1H, d, J=8.4 Hz), 6.93 (1H, d, J=8.4 Hz), 3.89 (3H, s), 3.84 (1H, m), 3.42 (2H, s), 2.84 (1H, s), 2.82 (1H, s), 1.95 (5H, m), 1.59 (2H, s), 1.51 (1H, s), 1.48 (1H, s), 0.97 (2H, m), 0.75 (2H, m).

N-Cyclopropyl-N-[1-(3-methyl-4-methoxybenzyl)piperidin-4-yl]-3-trifluoromethylbenzenesulfonamide was prepared from 4-bromomethyl-1-methoxy-2-methylbenzene according to the above procedure. LC: 99.6%. MS: m/z=483.1, 484.2 (M+H$^+$), 485.1 (M+2H$^+$). $^1$H NMR (400 MHz, CDCl$_3$): δ 8.12 (1H, s), 8.04 1H, d, J=7.6 Hz), 7.82 (1H, d, J=6.8 Hz), 7.66 (1H, m), 7.05 (2H, m), 6.75 (1H, m), 3.83 (1H, m), 3.81 3H, m), 3.39 (2H, s), 2.88 (2H, m), 2.20 (3H, s), 1.96 (5H, m), 1.57 (2H, s), 1.49 (2H, m), 0.98 (2H, m), 0.78 (2H, m).

N-Cyclopropyl-N-[1-(3-methyl-4-methoxybenzyl)piperidin-4-yl]benzenesulfonamide was prepared from 4-bromomethyl-1-methoxy-2-methylbenzene and N-cyclopropyl-N-piperidin-4-yl-benzenesulfonamide according to the above procedure. LC: 100%. MS: m/z=415.2, 416.2 (M+H$^+$). $^1$H NMR (400 MHz, CDCl$_3$): δ 7.82 (2H, d, J=8.0 Hz), 7.60 (1H, m), 7.52 (2H, m), 7.29 (1H, m), 7.21 (1H, s), 6.85 (1H, d, J=8.8 Hz), 4.13 (2H, s), 4.05 (1H, s), 3.85 (3H, s), 3.54 (2H, m), 2.63 (4H, m), 2.22 (3H, s), 1.75 (3H, m), 0.93 (2H, m), 0.86 (2H, m).

Example 8

N-Cyclopropyl-N-[1-(3-pyridylmethyl)piperidin-4-yl]-3-trifluoromethylbenzenesulfonamide (19)

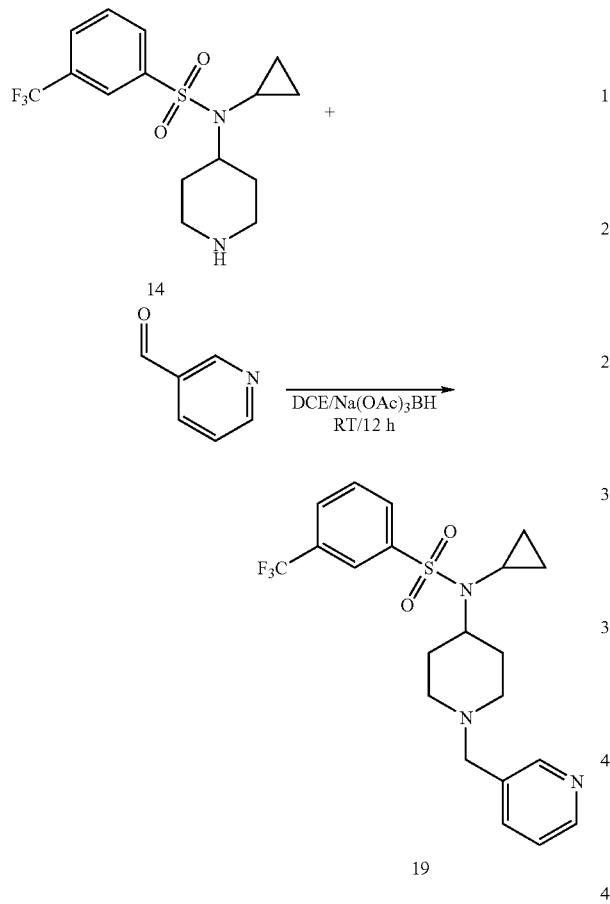

To a solution of N-cyclopropyl-N-piperidin-4-yl-3-trifluoromethyl-benzenesulfonamide (150 mg, 0.43 mmol) and pyridine-3-carboxaldehyde (46 mg, 0.43 mmol) in dichloroethane was added sodium triacetoxyborohydride (128 mg, 0.60 mmol, 1.4 eq.). The reaction mixture was stirred at room temperature for 12 hours. After this period, the solution was decanted and purified by flash chromatography to give the title compound 19 as a yellow oil. $^1$H NMR (CDCl$_3$): δ 8.55-8.48 (m, 2H), 8.15-8.11 (m, 1H), 8.08-8.02 (m, 1H), 7.87-7.81 (m, 1H), 7.71-7.59 (m, 1H), 7.25-7.20 (m, 1H), 3.92-3.81 (m, 1H), 3.48 (s, 2H), 2.91-2.81 (m, 2H), 2.10-1.87 (m, 5H), 1.56-1.45 (m, 2H), 1.01-0.94 (m, m, 2H), 0.82-0.74 (m, 2H). LC: 100%. MS (EI): m/z 440 (M+H$^+$).

Similarly, N-cyclopropyl-N-[1-(4-quinolinylmethyl)piperidin-4-yl]-3-trifluoromethylbenzenesulfonamide was prepared from quinoline-4-carboxaldehyde. LC: 100%. MS: m/z=490.2, 491.1 (M+H$^+$), 492.1 M+2H$^+$). $^1$H NMR (400 MHz, CDCl$_3$): δ 8.85 (1H, d, J=4 Hz), 8.13 (3H, m), 8.06 (1H, d, J=7.6 Hz), 7.83 (1H, d, J=7.2 Hz), 7.70 (2H, m), 7.56 (1H, m), 7.41 (1H, d, J=4 Hz), 3.90 (3H, m), 2.97 (1H, s), 2.94 (1H, s), 2.17 (2H, t, J=11 Hz), 1.98 (3H, m), 1.56 (4H, m), 0.98 (2H, m), 0.80 (2H, m).

Example 9

N-Cyclopropyl-N-[1-(4-methoxybenzyl)piperidin-4-yl]-3-trifluoromethylbenzenesulfonamide (20)

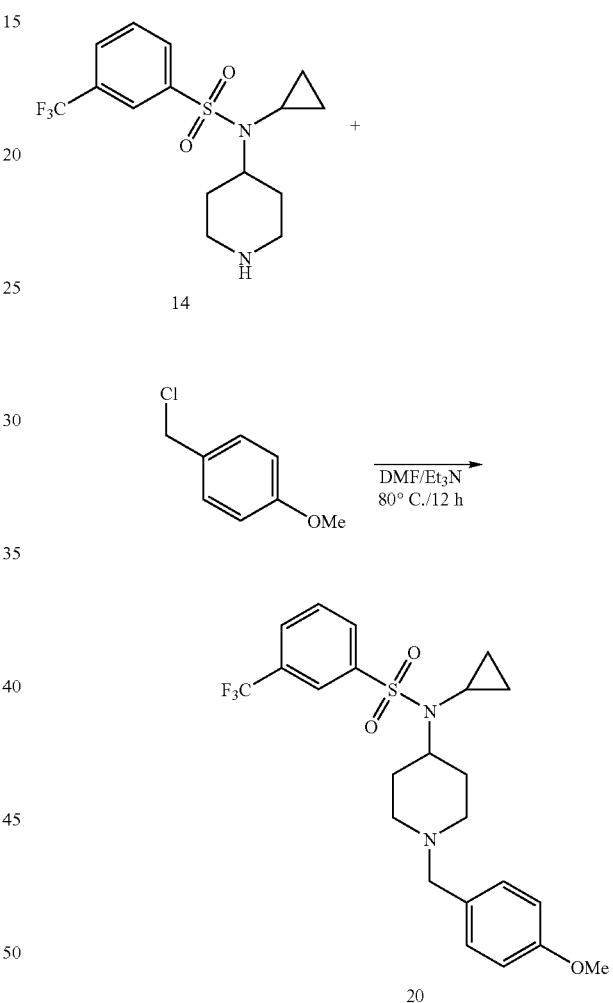

N-Cyclopropyl-N-piperidin-4-yl-3-trifluoromethyl-benzenesulfonamide (150 mg, 0.43 mmol) was dissolved in DMF (3 mL) and triethylamine (150 μL, 1.07 mmol, 2.5 eq.) added, followed by 1-chloromethyl-4-methoxybenzene (58 mg, 0.43 mmol). The reaction mixture was stirred for 12 hours at 80° C. and then the solvent was evaporated. The residue was purified by flash chromatography to give 244 mg of the title compound 20 as a yellow oil: $^1$H NMR (CDCl$_3$): δ 8.15-8.10 (m, 1H), 8.07-8.01 (m, 1H), 7.85-7.80 (m, 1H), 7.67-7.62 (m, 1H), 7.23-7.15 (m, 2H), 6.87-6.82 (m, 2H), 3.91-3.76 (m, 4H), 3.42 (s, 2H), 2.93-2.88 (m, 2H), 2.03-1.87

(m, 5H), 1.52-1.43 (m, 2H), 1.01-0.94 (m, 2H), 0.81-0.73 (m, 2H). LC: 100%. MS (EI): m/z 469 (M+H⁺).

Example 10

(2S) N-cyclopropyl-N-[1-(4-methyl-2-methylamino-pentanoyl)piperidin-4-yl]-3-trifluoromethylbenzene-sulfonamide (21)

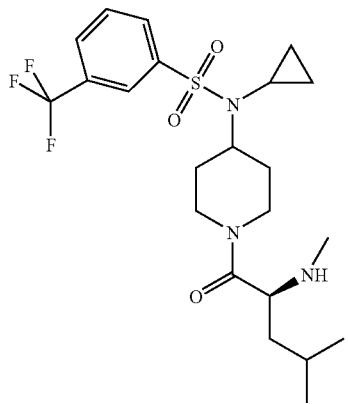 [SMILES: CN[C@@H](CC(C)C)C(=O)N1CCC(N(C2CC2)S(=O)(=O)c2cccc(C(F)(F)F)c2)CC1]

To a mixture of N-cyclopropyl-N-piperidin-4-yl-3-trifluoromethyl-benzenesulfonamide (1.0 g, 2.9 mmol), BOC-L-Meleu-OH (0.72 g, 2.9 mmol), 1-hydroxybenzotriazole hydrate (HOBt, 50 mg, 0.37 mmol), 4-dimethylaminopyridine (DMAP, 20 mg, 0.16 mmol) in dichloromethane (20 mL) was added 1,3-diisopropylcarbodiimide (DIC, 0.44 mL, 2.9 mmol) at room temperature under argon over 15 minutes. The reaction mixture was shaken at room temperature for 8 hours. The reaction mixture was cooled to 0° C., and the solid was removed by filtration. The organic layer was washed with NaOH aqueous solution (2N, 15 mL). The solvent was removed under vacuum and the residue was purified by column (silica gel, EtOAc/hexanes 3/7) to give the intermediate (1-{4-[cyclopropyl-(3-trifluoromethyl-benzenesulfonyl)amino]piperidine-1-carbonyl}-3-methylbutyl)methyl-carbamic acid tert-butyl ester as sticky colorless oil (1.3 g, 78%). This sticky oil in dichloromethane (10 mL) was treated with trifluoroacetic acid (1.5 mL) at 0° C. for 2.5 hours, and then the solvent was removed under vacuum. The residue was dissolved in dichloromethane (20 mL), neutralized with 2N NaOH solution, washed with water (5 mL) and brine (5 mL), and concentrated under vacuum to afford the desired product as free base (2S) N-cyclopropyl-N-[1-(4-methyl-2-methylaminopentanoyl)piperidin-4-yl]-3-trifluoromethyl-benzenesulfonamide (21) (colorless oil, 0.9 g, 90%).

The free base was dissolved in 1,4-dioxane and then treated with HCl (4N in 1,4-dioxane, 1.5 mL) The resulting mixture was triturated with ethyl ether (20 mL) and the precipitated material was collected by filtration, washed with ethyl ether (2×5 mL), and dried under vacuum for 12 hours to afford the desired product 21 as HCl-salt (white solid, 0.9 g, 93%). ¹H NMR (HCl-salt, CD₃OD): δ 8.21 (d, 1H, J=8.1 Hz), 8.19 (s, 1H), 8.04 (d, 1H, J=8.3 Hz), 7.87 (dd, 1H, J=7.9 & 8.0 Hz), 4.61-4.64 (m, 1H), 4.44-4.49 (m, 1H), 4.16-4.24 (m, 1H), 3.92-3.98 (m, 1H), 3.22-3.28 (m, 1H), 2.72-2.8 (m, 1H), 2.68 (s, 1.7H, NHCH₃), 2.72 (s, 1.3H, NHCH₃), 1.64-2.12 (m, 8H), 1.02-1.08 (m, 6H), 0.92-0.94 (m, 2H), 0.78-0.82 (m, 2H). MS (e/z): 476 (m+1).

Similarly, (2R) N-cyclopropyl-N-[1-(4-methyl-2-methylamino-pentanoyl)piperidin-4-yl]-3-trifluoromethylbenzenesulfonamide was prepared using BOC-D-Meleu-OH as a starting material. LC: 100%. MS: m/z=476 (M+H⁺). ¹H NMR (CDCl₃): δ 8.14 (bs, 1H), 8.06 (bd, 1H, J=8.11 Hz), 7.85 (bt, 1H, J=8.33 Hz), 7.71 (bt, 1H, J=7.67 Hz), 4.82-4.72 (m, 1H), 4.17-3.94 (m, 2H), 3.34-3.37 (m, 1H), 3.14-2.98 (m, 1H), 2.62-2.47 (m, 1H), 2.28 (d, 3H, J=10.08 Hz), 2.01-1.94 (m, 1H), 1.90-1.71 (m, 4H), 1.48-1.19 (m, 2H), 1.01-0.70 (m, 10H).

(2S) N-Cyclopropyl-N-[1-(4-methyl-2-methylaminopentanoyl)-piperidin-4-yl]-3-difluoromethoxybenzene-sulfonamide was prepared following the above procedure using N-cyclopropyl-N-piperidin-4-yl-3-difluoromethoxy-benzenesulfonamide as a starting material which can be prepared according to the method described in Example 3. LC: 100%. MS: m/z=474 (M+H⁺). ¹H NMR (CDCl₃): δ 7.76-7.71 (m, 1H), 7.67-7.64 (m, 1H), 7.59-7.54 (m, 1H), 7.40-7.35 (m, 1H), 6.61 (t, 1H, J=7.8 Hz), 4.79-4.71 (m, 1H), 4.15-3.92 (m, 2), 3.46-3.37 (m, 1H), 3.15-2.96 (m, 1H), 2.63-2.47 (m, 1H), 2.29 (d, 3H, J=10.74 Hz), 2.03-1.94 (m, 2H), 1.88-1.69 (m, 4H), 1.67-1.56 (m, 1H), 1.48-1.19 (m, 2H), 1.04-0.84 (m, 8H+H₂O), 0.82-0.70 (m, m, 2H).

The following compounds were prepared following the above procedure:

(2S) N-Cyclopropyl-N-[1-(4-methyl-2-methylaminopentanoyl)-piperidin-4-yl]-2-fluoro-5-trifluoromethylbenzenesulfonamide: LC: 100%. MS: m/z=494 (M+H⁺). ¹H NMR (CDCl₃): δ 8.29-8.22 (m, 1H), 7.92-7.83 (m, 1H), 7.39-7.33 (m, 1H), 4.87-4.75 (m, 1H), 4.33-4.21 (m, 1H), 4.10-3.95 (m, 1H), 3.61-3.44 (m, 1H), 3.22-3.03 (m, 1H), 2.71-2.55 (m, 1H), 2.51-2.24 (m, 6H), 2.23-2.11 (m, 1H), 2.07-1.69 (m, 5H), 1.54-1.22 (m, 2H), 1.01-0.64 (m, 10H+H₂O);

(2S) N-[1-(2-Aminopentanoyl)piperidin-4-yl]-N-cyclopropyl-3-trifluoromethylbenzenesulfonamide: LC: 100%. MS: m/z=448 (M+H⁺). ¹H NMR (CD₃OD): δ 8.24-8.16 (m, 2H), 8.06-8.00 (m, 1H), 7.90-7.84 (m, 1H), 4.66-4.54 (m, 1H), 4.46-4.36 (m, 1H), 4.25-4.09 (m, 1H), 3.99-3.88 (m, 1H), 3.28-3.16 (m, 1H), 2.80-2.68 (m, 1H), 2.14-2.02 (m, 1H), 2.02-1.59 (m, 6H), 1.55-1.35 (m, 2H), 1.06-0.97 (m, 3H), 0.96-0.87 (m, 2H), 0.84-0.74 (m, 2H);

(2S) N-Cyclopropyl-N-[1-(2-methylaminopentanoyl)piperidin-4-yl]-3-trifluoromethylbenzenesulfonamide: LC: 100%. MS: m/z=462 (M+H⁺). ¹H NMR (CD₃OD): δ 8.24-8.16 (m, 2H), 8.07-8.01 (m, 1H), 7.91-7.84 (m, 1H), 4.68-4.58 (m, 1H), 4.49-4.38 (m, 1H), 4.24-4.12 (m, 1H), 4.00-3.90 (m, 1H), 3.30-3.18 (m, 1H), 2.87-2.70 (m, 1H), 2.66 (d, 3H, J=11.4 Hz), 2.14-2.04 (m, 1H), 2.02-1.60 (m, 6H), 1.56-1.28 (m, 2H), 1.07-0.96 (m, 3H), 0.96-0.89 (m, 2H), 0.84-0.76 (m, 2H);

(2S) N-[1-(2-Amino-3-dimethylbutanoyl)piperidin-4-yl]-N-cyclopropyl-3-trifluoromethylbenzenesulfonamide: LC: 100%. MS: m/z=462 (M+H⁺). ¹H NMR (CD₃OD): δ 8.23-8.14 (m, 2H), 8.05-7.99 (m, 1H), 7.90-7.83 (m, 1H), 4.71-4.61 (m, 1H), 4.33-4.24 (m 1H), 4.22-4.09 (m, 1H), 3.27-3.11 (m, 2H), 2.81-2.64 (m, 1H), 2.11-2.02 (m, 1H), 2.01-1.78 (m, 2H), 1.77-1.61 (m, 2H), 1.16-1.04 (m, 9H), 0.99-0.86 (m, 2H), 0.84-0.77 (m, 2H);

(2S) N-[1-(2-Amino-2-cyclohexylethanoyl)piperidin-4-yl]-N-cyclopropyl-3-trifluoromethylbenzenesulfonamide: LC: 100%. MS: m/z=488.2 (M+H⁺). ¹H NMR (400 MHz, MeOD): δ 8.40 (2H, m), 8.19 (1H, m), 7.87 (1H, t, J=7.5 Hz), 4.61 (1H, d, J=11.5 Hz), 4.23 (1H, m), 4.17 (1H, m), 3.22 (1H, m), 2.75 (1H, q, J=11.5 Hz), 2.11 (1H, m), 1.61-1.98 (10H, m), 1.03-1.39 (5H, m), 0.92 (2H, m), 0.79 (2H, m);

(2R) N-[1-(2-Amino-2-cyclohexylethanoyl)piperidin-4-yl]-N-cyclopropyl-3-trifluoromethylbenzenesulfonamide: LC: 100%. MS: m/z=488.1, 489.1 (M+H⁺). ¹H NMR (400 MHz, MeOD): δ 8.20 (2H, m), 7.99 (1H, d, J=12 Hz), 7.87 (1H, t, J=7.5 Hz), 4.62 (1H, d, J=7.5 Hz), 4.28 (1H, m), 4.18 (1H, m), 3.98 (1H, m), 3.19 (1H, m), 2.76 (1H, m), 2.06 (1H, m), 1.75 (10H, m), 1.21 (5H, m), 0.92 (2H, m), 0.80 (2H, m); and (2S) N-Cyclopropyl-N-[1-(2-methylamino-2-phenylethanoyl)-piperidin-4-yl]-3-trifluoromethylbenzenesulfonamide: LC: 100%. MS: m/z=496.2, 497.2 (M+H⁺). ¹H NMR (400 MHz, MeOD): δ 8.07 (3H, m), 7.82 (1H, m), 7.53 (5H, m), 5.44 (1H, m), 4.63 (1H, d, J=7.5 Hz), 4.02 (1H, m), 3.82 (1H, m), 3.12 (1H, m), 2.67 (4H, m), 1.73 (4H, m), 0.58 (5H, m).

Example 11

(2S) N-Cyclopropyl-N-[1-(3-methyl-2-methylaminopentanoyl)-piperidin-4-yl]-3-trifluoromethylbenzenesulfonamide (22)

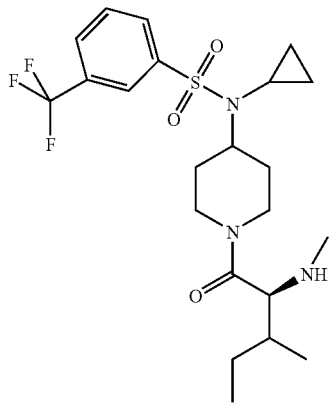 [SMILES: CCC(C)[C@H](NC)C(=O)N1CCC(N(C2CC2)S(=O)(=O)c2cccc(C(F)(F)F)c2)CC1]

A mixture of N-cyclopropyl-N-piperidin-4-yl-3-trifluoromethyl-benzenesulfonamide (100 mg, 0.29 mmol), BOC-L-MeIle-OH (70 g, 0.29 mmol), 1-hydroxybenzotriazole hydrate (HOBt, 39 mg, 0.29 mmol), 1-(3-dimethylaminopropyl)-3-ethylcarbodiimide hydrochloride (EDCI, 55 mg, 0.29 mmol), and DMF (5 mL) was shaken at room temperature for 2 hours. The reaction mixture was poured into 20 mL of ethyl acetate, washed with 5 mL of 2N HCl solution, saturated NaHCO₃ (20 mL), water (10 mL), and brine (10 mL). The organic layer was concentrated under vacuum, and purified by column (silica gel, EtOAc/hexane 1/1) to afford the intermediate (1-{4-[cyclopropyl-(3-trifluoromethylbenzenesulfonyl)amino]-piperidine-1-carbonyl}-2-methylbutyl)methylcarbamic acid tert-butyl ester as colorless oil.

The intermediate was dissolved in 1,4-dioxane (3 mL), and then treated with HCl solution (4N in 1,4-dioxane, 2 mL) at room temperature for 4 hours. The reaction mixture was triturated with ethyl ether (20 mL), and the precipitated material was collected by filtration, washed with ethyl ether (2×5 mL), and dried under vacuum for 12 hours to afford the desired material (2S) N-cyclopropyl-N-[1-(3-methyl-2-methylaminopentanoyl)piperidin-4-yl]-3-trifluoromethylbenzenesulfonamide (22) as HCl-salt (white solid, 80 mg, yield 54%). ¹H NMR (HCl-salt, CD₃OD): δ 8.22 (d, 1H, J=7.7 Hz), 8.17 (s, 1H), 8.04 (d, 1H, J=8.1 Hz), 7.87 (dd, 1H, J=7.7 & 8.3 Hz), 4.62-4.68 (m, 1H), 4.3-4.38 (m, 1H), 4.14-4.22 (m, 1H), 3.94-4.02 (m, 1H), 3.22-3.29 (m, 1H), 2.74-2.82 (m, 1H), 2.65 (s, 1.7H, NHCH₃), 2.62 (s, 1.3H, NHCH₃), 1.6-2.1 (m, 7H), 0.98-1.2 (m, 7H), 0.88-0.94 (m, 2H), 0.78-0.82 (m, 2H). LC: 100%. MS (e/z): 476 (m+1).

Example 12

N-[1-(2-Amino-3-m-tolylpropionyl)piperidin-4-yl]-N-cyclopropyl-3-trifluoromethylbenzenesulfonamide (23)

A mixture of N-cyclopropyl-N-piperidin-4-yl-3-trifluoromethyl-benzenesulfonamide (400 mg, 1.15 mmol), 2-tert-butoxycarbonylamino-3-m-tolyl-propionic acid (334 mg, 1.2 mmol), 1-hydroxybenzotriazole hydrate (HOBt, 50 mg, 0.37 mmol), 1-(3-dimethylaminopropyl)-3-ethylcarbodiimide hydrochloride (EDCI, 218 mg, 1.15 mmol), and DMF (5 mL) was shaken at room temperature for 8 hours. The reaction mixture was poured into 20 mL of ethyl acetate, washed with 5 mL of 2N HCl solution, saturated NaHCO₃ (20 mL), water (10 mL), and brine (10 mL). The organic layer was concentrated under vacuum and purified by column (silica gel, EtOAc/hexane 1/1) to afford the intermediate [2-{4-[cyclopropyl-(3-trifluoromethylbenzenesulfonyl)-amino]piperidin-1-yl}-1-(3-methylbenzyl)-2-oxo-ethyl]carbamic acid tert-butyl ester as colorless oil (600 mg, yield 85%).

The intermediate was dissolved in 1,4-dioxane (5 mL), and then treated with HCl solution (4N in 1,4-dioxane, 2 mL) at room temperature for 4 hours. The reaction mixture was triturated with ethyl ether (20 mL), and the precipitated material was collected by filtration, washed with ethyl ether (2×5 mL), and dried under vacuum for 12 hours to afford the title compound 23 as a HCl-salt (white solid, 400 mg, yield 70%). LC: 98%. ¹H NMR (DMSO-d₆): δ 8.31 (bs, 3H), 8.12 (m, 2H), 8.06 (s, 1H), 7.89 (m, 1H), 7.11 (cm, 4H), 4.58 (m, 1H), 4.40 (m, 1H), 3.91 (m, 1H), 3.07 (m, 1H), 2.88 (m, 1.5H), 2.36 (m, 0.5H), 2.26 (d, 3H), 1.79-1.99 (m, 1H), 1.43-1.71 (m, 2.5H), 1.28 (m, 1H), 0.92 (d, 0.5H), 0.74 (d, 4H), 0.15 (q, 0.5H). MS (e/z): 510 (m+1).

The following compounds were prepared similarly:

N-{1-[2-Amino-3-(4-fluorophenyl)propionyl]piperidin-4-yl}-N-cyclopropyl-3-trifluoromethylbenzenesulfonamide: LC: 100%. MS: m/z 514.2, 515.2 (M+H⁺). ¹H NMR (400 MHz, DMSO-d₆): δ 8.17 (6H, m), 7.91 (1H, t, J=7.5 Hz), 7.23 (4H, m), 4.64 (1H, m), 4.38 (1H, m), 4.02 (1H, m), 3.73 (1H, m), 2.95 (3H, m), 1.19-1.98 (4.5H, m), 0.77 (4.5H, m);

N-[1-(2-Amino-3-o-tolylpropionyl)piperidin-4-yl]-N-cyclopropyl-3-trifluoromethylbenzenesulfonamide: LC: 100%. MS: m/z=589.2, 590.2 (M+H⁺). ¹H NMR (400 MHz, DMSO-d₆): δ 8.15 (6H, m), 7.91 (1H, t, J=7.5 Hz), 7.15 (4H, m), 4.62 (1H, m), 4.38 (1H, m), 4.00 (1H, m), 3.69 (1H, m), 2.95 (3H, m), 2.19 (3H, m), 1.10-2.01 (4.5H, m), 0.76 (4H, m), 0.56 (0.5H, m); and N-{1-[2-Amino-3-(4-tert-butylphenyl)propionyl]piperidin-4-yl}-N-cyclopropyl-3-trifluoromethylbenzenesulfonamide: LC: 100%. MS: m/z=552.3, 553.3 (M+H⁺). ¹H NMR (400 MHz, DMSO-d₆): δ 8.13 (6H, m), 7.90 (1H, m), 7.32 (2H, m), 7.19 (1H, d, J=7.5 Hz), 7.10 (1H, d, J=7.5 Hz), 4.61 (1H, m), 4.43 (1H, m), 3.89-4.01 (1H, m), 3.62 (1H, m), 2.92 (3H, m), 1.54-2.02 (3H, m), 1.15 (1H, m), 0.75 (4H, m).

Example 13

N-{1-[2-Amino-3-(4-cyanophenyl)propionyl]piperidin-4-yl}-N-cyclopropyl-3-trifluoromethylbenzenesulfonamide (24)

A mixture of N-cyclopropyl-N-piperidin-4-yl-3-trifluoromethyl-benzenesulfonamide (400 mg, 1.15 mmol), 2-tert-butoxycarbonylamino-3-(4-cyanophenyl)propionic acid (320 mg, 1.2 mmol), 1-hydroxybenzotriazole hydrate (HOBt, 50 mg, 0.37 mmol), 1-(3-dimethylaminopropyl)-3-ethylcarbodiimide hydrochloride (EDCI, 218 mg, 1.15 mmol), and DMF (5 mL) was shaken at room temperature for 8 hours. The reaction mixture was then poured into 20 mL of ethyl acetate, washed with 5 mL of 2N HCl solution, saturated NaHCO$_3$ (20 mL), water (10 mL), and brine (10 mL). The organic layer was concentrated under vacuum and purified by column (silica gel, EtOAc/hexane 1/1) to afford the intermediate (1-(4-cyanobenzyl)-2-{4-[cyclopropyl-(3-trifluoromethylbenzenesulfonyl)amino]piperidin-1-yl}-2-oxo-ethyl)carbamic acid tert-butyl ester as colorless oil.

The intermediate was dissolved in 1,4-dioxane (5 mL), and then treated with HCl solution (4N in 1,4-dioxane, 2 mL) at room temperature for 4 hours. The reaction mixture was triturated with ethyl ether (20 mL), and the precipitated material was collected by filtration, washed with ethyl ether (2×5 mL), and dried under vacuum for 12 hours to afford the title compound 24 as a HCl-salt (white solid, 400 mg, yield 67%). $^1$H NMR (HCl-salt, DMSO-d$_6$): δ 8.28-8.36 (br, 3H, NH$_2$.HCl), 8.18 (dd, J=8.1 & 8.7 Hz), 8.13 (d, 1H, J=8.3 Hz), 8.11 (s, 1H), 7.92 (dd, 1H, J=7.8 & 7.9 Hz), 7.83 (d, 1H, J=8.3 Hz), 7.81 (d, 1H, J=8.3 Hz), 7.46 (d, 1H, J=8.1 Hz), 7.41 (d, 1H, J=8.3 Hz), 4.68-4.76 (m, 1H), 4.34-4.39 (m, 1H), 4.02-4.08 (m, 1H), 3.74-3.78 (m, 1H), 2.98-3.18 (m, 2.5H), 2.56-2.66 (m, 2H), 1.96-1.99 (m, 0.5H), 1.25-1.86 (m, 4H), 0.73-0.83 (m, 4H). LC: 100%. MS (e/z): 521 (m+1).

Example 14

(2S) N-Cyclopropyl-N-[1-(2-dimethylamino-4-methylpentanoyl)piperidin-4-yl]-3-trifluoromethylbenzenesulfonamide (25)

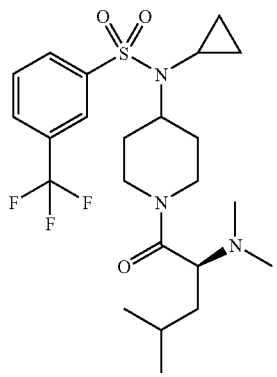 [SMILES: CC(C)C[C@@H](C(=O)N1CCC(N(C2CC2)S(=O)(=O)c2cccc(C(F)(F)F)c2)CC1)N(C)C]

A mixture of (2S) N-cyclopropyl-N-[1-(4-methyl-2-methylamino-pentanoyl)piperidin-4-yl]-3-trifluoromethylbenzenesulfonamide (see Example 10, 323 mg, 0.7 mmol), methanol (4 mL), paraformaldehyde (50 mg, 1.0 mmol), NaBH$_3$(CN) (132 mg, 2 mmol), and acetic acid (0.01 mL) was shaken at room temperature for 20 hours. The solvents were removed under vacuum. The residue was dissolved in dichloromethane (15 mL), and treated with aqueous saturated K$_2$CO$_3$ (5 mL). The organic layer was separated, washed with brine, concentrated under vacuum, and purified by column (silica gel, EtOAc/hexane 3/7) to give the title compound (2S) N-cyclopropyl-N-[1-(2-dimethylamino-4-methylpentanoyl)piperidin-4-yl]-3-trifluoromethyl-benzenesulfonamide as white solid (30 mg, yield 10%). $^1$H NMR (CDCl$_3$): δ 8.14 (s, 1H), 8.08 (d, 1H, J=7.9 Hz), 7.87 (d, 1H, J=7.7 Hz), 7.7 (dd, 1H, J=7.7 & 8.1 Hz), 4.7-4.76 (m, 1H), 4.18-4.24 (m, 1H), 4.06-4.12 (m, 1H), 3.34-3.4 (m, 1H), 2.94-3.06 (m, 1H), 2.44-2.54 (m, 1H), 2.26 (br, 6H), 1.35-1.98 (m, 8H), 0.94-1.02 (m, 2H), 0.86-0.95 (m, 6H), 0.74-0.78 (m, 2H). LC: 100%. MS (e/z), 490 (m+1).

Similarly, (2R) N-cyclopropyl-N-[1-(2-dimethylamino-4-methylpentanoyl)piperidin-4-yl]-3-trifluoromethylbenzenesulfonamide was prepared from (2R) N-cyclopropyl-N-[1-(4-methyl-2-methylamino-pentanoyl)piperidin-4-yl]-3-trifluoromethylbenzenesulfonamide (see Example 10). LC: 100%. MS: m/z=490.2, 491.2 (M+H$^+$). $^1$H NMR (400 MHz, CDCl$_3$): δ 8.13 (1H, s), 8.06 (1H, d, J=7.7 Hz), 7.86 (1H, d, J=7.9 Hz), 7.69 (1H, t, J=7.9 Hz), 4.77-4.68 (1H, m), 4.23 (1H, m), 4.09 (1H, m), 3.36 (1H, m), 3.08-2.92 (1H, m), 2.57-2.43 (1H, m), 2.25 (6H, s), 1.95 (2H, m), 1.77 (3H, m), 1.60 (1H, m), 1.45 (1H, m), 1.39-1.23 (1H, m), 1.01-0.81 (8H, m), 0.74 (2H, m).

Example 15

(2S) N-{1-[3-(4-Cyanophenyl)-2-methylaminopropionyl]piperidin-4-yl}-N-cyclopropyl-3-trifluoromethylbenzenesulfonamide (26)

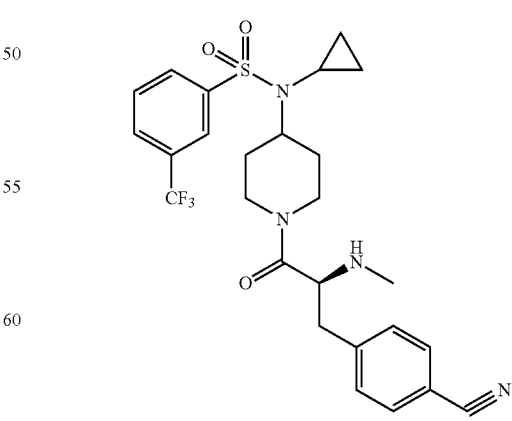

A mixture of N-{1-[2-amino-3-(4-cyanophenyl)propionyl]piperidin-4-yl}-N-cyclopropyl-3-trifluoromethylbenzenesulfonamide (see Example 13, 300 mg, 0.58 mmol), MeI (830 mg, 5.9 mmol), and DMF (5 mL) was treated with NaH (67 mg, 60% mineral oil, 1.8 mmol) at room temperature for 20 hours. The reaction mixture was diluted with ethyl acetate (20 mL), and washed with water (5 mL) and brine (5 mL). The organic layer was evaporated and the residue was purified by column (silica gel, EtOAc/hexane 1/1) to give the title compound N-{1-[3-(4-cyanophenyl)-2-methylamino-propionyl]piperidin-4-yl}-N-cyclopropyl-3-trifluoromethyl-benzenesulfonamide (26) as free base, which was dissolved in 1,4-dioxane (4 mL), and treated with HCl solution (4N in 1,4-dioxane, 1 mL). The resulting mixture was triturated with ethyl ether (10 mL), and the precipitated material was collected by filtration, washed with ethyl ether (2×5 mL), and dried under vacuum for 12 hours to afford the title compound 26 as a HCl-salt (white solid, 0.2 g, yield 65%). $^1$H NMR (HCl-salt, CD$_3$OD): δ 8.12-8.19 (m, 2H), 8.03 (d, 1H, J=9.2 Hz), 7.86 (dd, 1H, J=7.7 & 7.8 Hz), 7.77 (dd, 2H, J=4.3 & 8.1 Hz), 7.49 (dd, 2H, J=1.9 & 8.3 Hz), 4.76-4.79 (m, 1H), 4.52-4.59 (m, 1H), 3.96-4.06 (m, 1H), 3.6-3.7 (m, 1H), 3.34-3.38 (m, 1H), 3.06-3.14 (m, 2H), 2.68-2.72 (m, 3H, NCH$_3$), 2.34-2.65 (m, 2H), 1.52-2.02 (m, 4H), 0.62-0.92 (m, 4H). LC: 100%. MS (e/z): 535 (m+1).

The following compounds were prepared similarly:

N-Cyclopropyl-N-[1-(2-methylamino-3-o-tolylpropionyl)piperidin-4-yl]-3-trifluoromethylbenzenesulfonamide: LC: 100%. MS: m/z=524.3, 525.3 (M+H$^+$). $^1$H NMR (400 MHz, MeOD): δ 8.11 (2H, m), 8.00 (1H, m), 7.83 (1H, m), 7.28-7.11 (2H, m), 7.09-6.96 (2H, m), 4.68 (1H, m), 4.59-4.49 (1H, m), 3.93 (1H, m), 3.68-3.49 (1H, m), 3.21 (1H, m), 2.94 (1H, m), 2.72-2.58 (4H, m), 2.51-2.07 (4H, m), 2.03-1.73 (2H, m), 1.65-1.39 (2H, m), 1.27-0.40 (5H, m);

N-Cyclopropyl-N-[1-(2-methylamino-3-m-tolylpropionyl)piperidin-4-yl]-3-trifluoromethylbenzenesulfonamide: LC: 100%. MS: m/z=524.3, 525.3 (M+H$^+$). $^1$H NMR (400 MHz, MeOD): δ 8.07 (2H, m), 7.97 (1H, m), 7.81 (1H, m), 7.26-7.05 (4H, m), 4.66-4.49 (2H, m), 3.91-3.76 (1H, m), 3.40-3.20 (2H, m), 3.12-2.88 (2H, m), 2.73 (3H, d), 2.64-2.54 (1H, t), 2.34-2.28 (3H, s), 2.00-1.91 (1H, m), 1.82-1.64 (2H, m), 1.61-1.31 (2H, m), 1.10-1.01 (1H, m), 0.87-0.65 (4H, m);

N-Cyclopropyl-N-{1-[3-(4-fluorophenyl)-2-methylaminopropionyl]-piperidin-4-yl}-3-trifluoromethylbenzenesulfonamide: LC: 100%. MS: m/z 528.2, 529.2 (M+H$^+$). $^1$H NMR (400 MHz, MeOD): δ 8.09 (2H, m), 7.98 (1H, d, J=7.5 Hz), 7.81 (1H, t, J=7.9 Hz), 7.28 (1H, m), 7.20 (1H, m), 7.80 (2H, m), 4.69-4.63 (1H, m), 4.53 (1H, d), 4.02-3.88 (1H, m), 3.67-3.52 (1H, m), 3.28-2.93 (3H, m), 2.71-2.57 (4H, m), 2.55-2.23 (1H, m), 2.03-1.73 (2H, m), 1.65-1.41 (2H, m), 1.33-0.51 (5H, m);

N-Cyclopropyl-N-{1-[3-(4-tert-butylphenyl)-2-methylamino-propionyl]piperidin-4-yl}-3-trifluoromethylbenzenesulfonamide: LC: 100%. MS: m/z=566.2, 567.3 (M+H$^+$). $^1$H NMR (400 MHz, MeOD): δ 8.10 (2H, m), 8.00 (1H, d), 7.82 (1H, t), 7.40 (2H, m), 7.23 (1H, d), 7.13 (1H, d), 4.60-4.40 (2H, m), 3.97-3.72 (1H, m), 3.46 (1H, t), 3.09 (1H, m), 3.01-2.31 (6H, m), 2.01-1.87 (1H, m), 1.78-1.57 (2H, m), 1.57-0.57 (16H, m); and (2S) N-Cyclopropyl-N-[1-(2-methylamino-3-phenylpropionyl)-piperidin-4-yl]-3-trifluoromethylbenzenesulfonamide: LC: 100%. MS: m/z=510 (M+H$^+$). $^1$H NMR (CDCl$_3$): δ 8.12 (1H, s), 8.09 (1H, d), 7.98 (1H, d), 7.82 (1H, m), 7.36 (2H, m), 7.21 (2H, m), 7.15 (1H, t), 4.69 (1H, t), 4.53 (1H, d), 3.92 (1H, m), 3.60 (2H, d), 3.33 (1H, d), 2.99 (1H, m), 2.68 (3H, d), 2.30 (1H, m), 2.02 (1H, m), 1.86 (1H, m), 1.64 (2H, m), 1.21 (1H, m), 0.78 (4H, m), 0.60 (1H, m).

Example 16

N-[1-(4-Butoxyphenylsulfonyl)piperidin-4-yl]-N-cyclopropylbenzenesulfonamide (27)

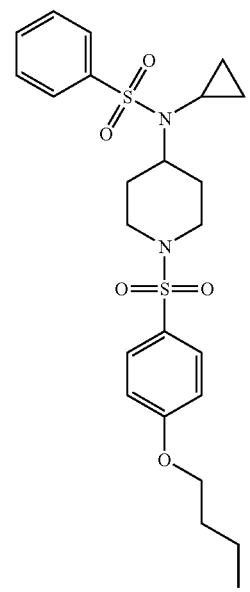 [SMILES: CCCCOc1ccc(S(=O)(=O)N2CCC(N(C3CC3)S(=O)(=O)c3ccccc3)CC2)cc1]

143 mg (0.513 mmol) of N-cyclopropyl-N-piperidin-4-yl-benzenesulfonamide (available from Lancaster) and 128 mg (0.513 mmol) of 4-butoxyphenylsulfonyl chloride (available from Matrix Scientific) were each dissolved in 5 mL dichloromethane (DCM) and then combined. 1.5 eq. of diisoprolyl-ethylamine (DIEA) (0.134 mL) was added to the mixture by syringe. The mixture was stirred overnight at room temperature and then concentrated under vacuum. The resultant product 27 was purified through a column of silica gel with a gradient of 0% to 20% EtOAc in hexanes and the pure material was concentrated (yield 24%, white solid). $^1$H NMR (CDCl$_3$): δ 7.813-7.783 (m, 2H), 7.673-7.636 (m, 2H), 7.597-7.553 (m, 1H), 7.520-7.475 (m, 2H), 7.011-6.974 (m, 2H), 4.053-4.020 (t, 2H), 3.821-3.721 (m, 3H), 2.266-2.200 (t, 2H), 2.033-1.902 (m, 3H), 1.843-1.779 (m, 2H), 1.601-1.470

(m, 4H), 1.015-0.978 (t, 3H), 0.935-0.896 (m, 2H), 0.761-0.712 (m, 2H). LC: 100%. MS (e/z): 494 (M+H⁺).

Example 17

N-Cyclopropyl-N-[1-(4-propylphenylsulfonyl)piperidin-4-yl]-3-trifluoromethylbenzenesulfonamide (28)

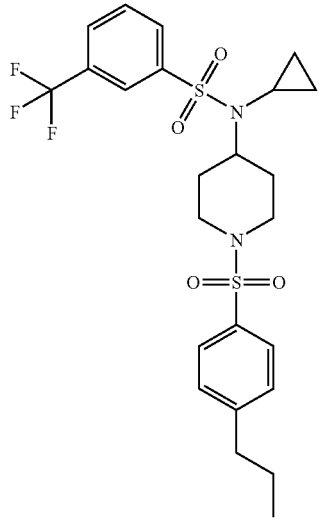 [SMILES: CCCc1ccc(S(=O)(=O)N2CCC(N(C3CC3)S(=O)(=O)c3cccc(C(F)(F)F)c3)CC2)cc1]

150 mg (0.434 mmol) of N-cyclopropyl-N-piperidin-4-yl-3-trifluoromethylbenzenesulfonamide (available from Lancaster) and 95 mg (0.434 mmol) of 4-propylphenylsulfonyl chloride (available from Matrix Scientific) were each dissolved in 10 mL of DCM and then combined. 1.5 eq. of DIEA (0.113 mL) was added to the mixture by syringe. The mixture was stirred overnight at room temperature and then concentrated under vacuum. The resultant product 28 was purified through a column of silica gel with a gradient of 0% to 20% EtOAc in hexanes and the pure material was concentrated (yield 11%, white solid). ¹H NMR (CDCl₃): δ 8.053 (s, 1H), 8.003-7.982 (d, 1H), 7.852-7.832 (d, 1H), 7.686-7.630 (m, 3H), 7.366-7.340 (d, 2H), 3.868-3.764 (m, 3H), 2.699-2.660 (t, 2H), 2.313-2.246 (t, 2H), 2.071-1.900 (m, 3H), 1.738-1.587 (m, 4H), 0.991-0.954 (t, 3H), 0.936-0.896 (m, 2H), 0.789-0.739 (m, 2H). LC: 100%. MS (e/z): 532 (M+H⁺).

Similarly, N-cyclopropyl-N-[1-(4-propylphenylsulfonyl)piperidin-4-yl]benzenesulfonamide can be prepared starting from N-cyclopropyl-N-piperidin-4-yl-benzenesulfonamide. Also, N-cyclopropyl-N-[1-(5-dimethylaminonaphthylsulfonyl)piperidin-4-yl]benzenesulfonamide can be prepared according to the above described procedure starting from N-cyclopropyl-N-piperidin-4-yl-benzenesulfonamide and 5-dimethylaminonaphthylsulfonyl chloride.

Example 18

N-[1-(4-butoxyphenylsulfonyl)piperidin-4-yl]-N-cyclopropyl-3-trifluoromethylbenzenesulfonamide (29)

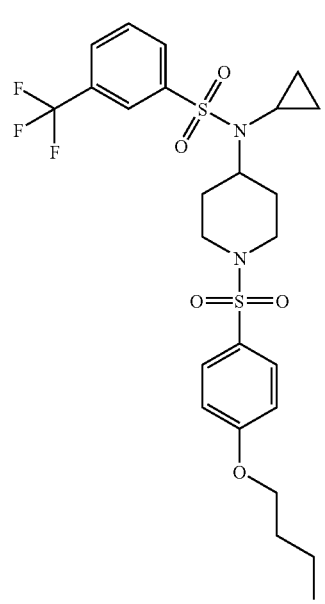 [SMILES: CCCCOc1ccc(S(=O)(=O)N2CCC(N(C3CC3)S(=O)(=O)c3cccc(C(F)(F)F)c3)CC2)cc1]

150 mg (0.434 mmol) of N-cyclopropyl-N-piperidin-4-yl-3-trifluoromethylbenzenesulfonamide (available from Lancaster) and 108 mg (0.434 mmol) of 4-butoxyphenylsulfonyl chloride (available from Matrix Scientific) were each dissolved in 10 mL of DCM and then combined. 1.5 eq. of DIEA (0.113 mL) was added to the mixture by syringe. The mixture was stirred overnight at room temperature and then concentrated under vacuum. The resultant product 29 was purified through a column of silica gel with a gradient of 0% to 20% EtOAc in hexanes and the pure material was concentrated (yield 25%, white solid). ¹H NMR (CDCl₃): δ 8.058 (s, 1H), 8.003-7.983 (d, 1H), 7.851-7.831 (d, 1H), 7.688-7.641 (m, 3H), 7.017-6.980 (m, 2H), 4.055-4.022 (t, 2H), 3.843-3.746 (m, 3H), 2.286-2.226 (t, 2H), 2.068-1.901 (m, 3H), 1.843-1.773 (m, 2H), 1.6151-1.470 (m, 4H), 1.014-0.976 (t, 3H), 0.944-0.903 (m, 2H), 0.793-0.744 (m, 2H). LC: 100%. MS (e/z): 562 (M+H⁺).

Example 19

N-Cyclopropyl-N-{1-[3-(4-methylpiperazinyl)hex-anoyl]piperidin-4-yl}-3-trifluoromethylbenzene-sulfonamide (31)

N-Cyclopropyl-N-{1-[3-(piperidin-1-yl)hexanoyl]piperidin-4-yl}-3-trifluoromethylbenzene-sulfonamide (32)

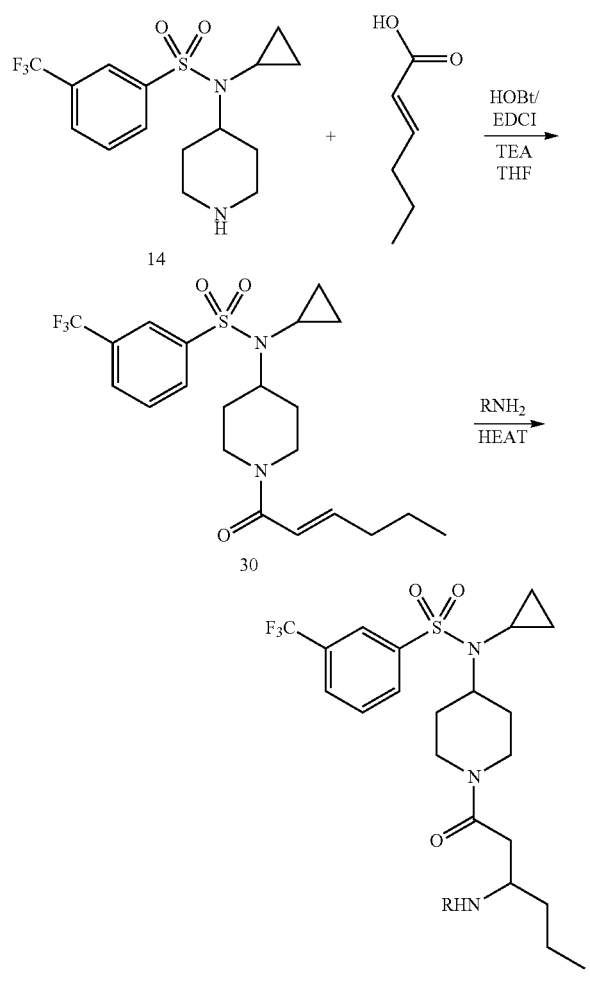

a) N-Cyclopropyl-N-(1-hex-2-enoyl-piperidin-4-yl)-3-trifluoromethylbenzenesulfonamide (30): N-cyclopropyl-N-(piperidin-4-yl)-3-trifluoromethylbenzenesulfonamide (6.0 g, 17.22 mmol) and 2-hexenoic acid (1.79 g, 17.22 mmol) were added in dry THF (100 mL) under nitrogen atmosphere. HOBT (2.79 g, 20.66 mmol) and EDCI (3.69 g, 20.66 mmol), and triethylamine (7.2 mL, 51.66 mmol) were added to the mixture. The mixture was stirred at room temperature overnight. The resulting mixture was partitioned between EtOAc and 1.0 M sodium chloride (250 mL). The organic layer was separated, dried (MgSO4), and concentrated to give a crude product as a gum, which was crystallized by hexane/ether (2:1) to give the desired compound 30 (7.58 g, 100% yield) as a white solid. LC: 100%. MS: m/z=445.2 (M+H), 467.3 (M+Na). $^1$H NMR (400 MHz, CDCl$_3$): (1:1 mixture of rotamers) δ 8.14 (1H, s), 8.07 (1H, d, J=7.5 Hz), 7.88 (1H, d, J=7.5 Hz), 7.70 (1H, t, J=7.5 Hz), 6.86 (1H, dt, J=15.0, 6.0 Hz), 6.32 (1H, d, J=15.0 Hz), 4.75 (1H, bd, J=10.7 Hz), 4.10 (2H, m), 3.06 (1H, bt, J=13.0 Hz), 2.56 (1H, bt, J=13.0 Hz), 2.20 (2H, q, J=8.9 Hz), 1.95 (1H, m), 1.90-1.45 (7H, m), 1.05-0.85 (5H, m), 0.75 (2H, m).

b) N-Cyclopropyl-N-{1-[3-(4-methylpiperazinyl)hexanoyl]-piperidin-4-yl}-3-trifluoromethylbenzene-sulfonamide (31): N-cyclopropyl-N-(1-hex-2-enoyl-piperidin-4-yl)-3-trifluoromethylbenzenesulfonamide (30) (250 mg, 0.56 mmol) and N-methylpiperazine (1.80 g, 18 mmol) were mixed together in a screw-capped vial and heated to 130° C. on a metal block for 3 days. The mixture was cooled and evaporated in vacuum, and the residue was purified by column chromatography on silica gel (EtOAc/MeOH/NH$_2$OH, 100:10:1) to give the title compound 31 (120 mg, 39% yield) as a white solid. $^1$H NMR (CDCl$_3$): δ 8.14 (S, 1H), 8.06 (d, 1H), 7.87 (d, 1H), 7.71 (t, 1H), 4.71 (d, 1H), 4.09 (t, 1H), 3.95 (d, 1H), 3.07 (m, 2H), 2.51 (m, 9H), 2.25 (m, 3H), 2.16 (m, 1H), 1.95 (m, 1H), 1.73 (m, 4H), 1.35 (m, 5H), 0.99 (m, 1H), 0.80 (m, 6H). LC: 100%. MS (M+H$^+$): 545.

By following the procedure described above, N-cyclopropyl-N-(1-hex-2-enoyl-piperidin-4-yl)-3-trifluoromethylbenzenesulfonamide (30) was reacted with piperidine and N-cyclopropyl-N-{1-[3-(piperidin-1-yl)hexanoyl]piperidin-4-yl}-3-trifluoromethylbenzenesulfonamide (32) was obtained as a white solid. $^1$H NMR (CDCl$_3$): δ 8.15 (S, 1H), 8.06 (d, 1H), 7.87 (d, 1H), 7.71 (t, 1H), 4.71 (d, 1H), 4.09 (m, 1H), 3.95 (d, 1H), 3.02 (m, 2H), 2.39 (m, 6H), 2.15 (m, 1H), 1.96 (m, 1H), 1.80 (m, 3H), 1.40 (m, 11H), 0.96 (m, 1H), 0.80 (m, 6H). LC: 100%. MS (M+H$^+$): 530.

Example 20

N-Cyclopropyl-N-{1-[4,4-bis(4-fluorophenyl)-but-3-enoyl]piperidin-4-yl}-3-trifluoromethylbenzene-sulfonamide (33)

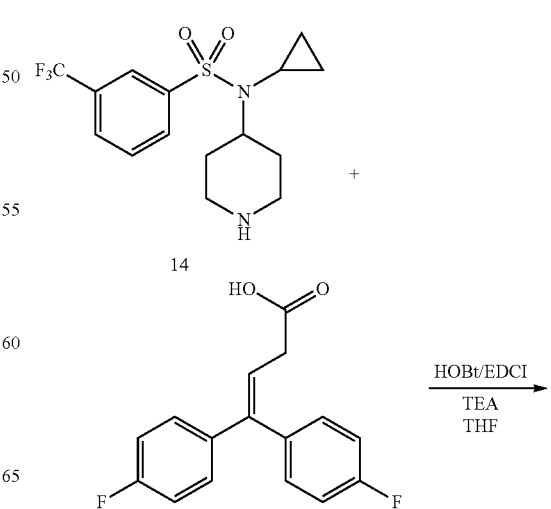

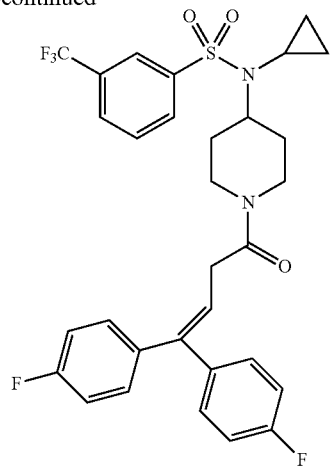

33

N-Cyclopropyl-N-{1-[4,4-bis(4-fluorophenyl)-but-3-enoyl]piperidin-4-yl}-3-trifluoromethylbenzenesulfonamide (33) was prepared by reacting N-cyclopropyl-N-piperidin-4-yl-3-trifluoromethylbenzenesulfonamide with 4,4-bis(4-fluorophenyl)-but-3-enoic acid following the procedure described for the synthesis of N-cyclopropyl-N-(2-hexenoyl)piperin-4-yl-3-trifluoromethyl-benzenesulfonamide (30) in Example 19, step a. $^1$H NMR (CDCl$_3$): δ 8.12 (s, 1H), 8.03 (d, 1H), 7.86 (d, 1H), 7.71 (t, 1H), 7.15 (m, 6H), 6.96 (m, 2H), 6.21 (t, 1H), 4.68 (m, 1H), 4.02 (m, 1H), 3.61 (m, 1H), 3.15 (d, 2H), 2.93 (m, 1H), 2.51 (m, 1H), 1.93 (m, 1H), 1.69 (m, 2H), 1.25 (m, 1H), 0.90 (m, 5H). LC: 100%. MS (M+H$^+$): 605.

Similarly, the following compounds were prepared:

N-Cyclopropyl-N-{1-[4-(4-fluorophenyl)-4-oxobutanoyl]-piperidin-4-yl}-3-trifluoromethylbenzenesulfonamide was prepared from N-cyclopropyl-N-(piperidin-4-yl)-3-trifluoromethylbenzenesulfonamide and 4-(4-fluorophenyl)-4-oxo-butanoic acid. LC: 100%. MS: m/z=527 (M+H$^+$). $^1$H NMR (CDCl$_3$): δ 8.14 (1H, s), 8.04 (3H, m), 7.87 (1H, d), 7.70 (1H, t), 7.12 (2H, t), 4.68 (1H, d), 4.09 (2H, m), 3.30 (2H, m), 3.09 (1H, t), 2.77 (2H, m), 2.53 (1H, t), 1.85 (5H, m), 0.92 (2H, m), 0.75 (2H, m);

N-Cyclopropyl-N-[1-(3,3-diphenylpropanoyl)piperidin-4-yl]-3-trifluoromethylbenzenesulfonamide was prepared from N-cyclopropyl-N-(piperidin-4-yl)-3-trifluoromethyl-benzenesulfonamide and 3,3-diphenylpropanoic acid. LC: 100%. MS: m/z=557 (M+H$^+$). $^1$H NMR (CDCl$_3$): δ 8.11 (1H, s), 8.02 (1H, d), 7.84 (1H, d), 7.70 (1H, t), 7.23 (10H, m), 4.64 (2H, m), 3.98 (1H, m), 3.85 (1H, d), 3.00 (2H, m), 2.82 (1H, t), 2.37 (1H, t), 1.86 (1H, m), 1.60 (4H, m), 0.91 (1H, m), 0.72 (3H, m);

N-Cyclopropyl-N-{1-[4,4-bis(4-fluorophenyl)butanoyl]piperidin-4-yl}-3-trifluoromethylbenzenesulfonamide was prepared from N-cyclopropyl-N-(piperidin-4-yl)-3-trifluoromethylbenzenesulfonamide and 4,4-bis(4-fluorophenyl)butanoic acid. LC: 100%. MS: m/z=607 (M+H$^+$). $^1$H NMR (CDCl$_3$): δ 8.12 (1H, s), 8.04 (1H, d), 7.86 (1H, d), 7.69 (1H, t), 7.16 (4H, dd), 6.98 (4H, dd), 4.71 (1H, d), 3.98 (1H, d), 3.80 (1H, t), 3.68 (1H, d), 2.91 (1H, t), 2.50 (1H, t), 2.33 (2H, m), 2.21 (2H, m), 1.93 (1H, m), 1.75 (4H, m), 0.91 (4H, m);

N-Cyclopropyl-N-{1-[4,4-bis(4-fluorophenyl)butanoyl]piperidin-4-yl}-2-trifluoromethylbenzenesulfonamide was prepared from N-cyclopropyl-N-(piperidin-4-yl)-2-trifluoromethylbenzenesulfonamide and 4,4-bis(4-fluorophenyl)butanoic acid which can be prepared according to Sindelar et al. (*Collection of Czechoslovak Chemical Communications* 38(12): 3879-3901 (1973)). LC: 100%. MS: m/z=607 (M+H$^+$). $^1$H NMR (CDCl$_3$): δ 8.29 (1H, d), 7.88 (1H, d), 7.72 (2H, m), 7.18 (4H, dd), 6.98 (4H, dd), 4.76 (1H, d), 4.25 (1H, m), 3.95 (1H, m), 3.72 (1H, d), 3.00 (1H, t), 2.55 (1H, t), 2.30 (5H, m), 1.84 (4H, m), 0.61 (2H, m), 0.49 (1H, m), 0.36 (1H, m); and N-Cyclopropyl-N-{1-[(3-trifluoromethyl-4-methoxy)benzoyl]piperidin-4-yl}-3-trifluoromethylbenzenesulfonamide was prepared from N-cyclopropyl-N-(piperidin-4-yl)-3-trifluoromethyl-benzenesulfonamide and 3-trifluoromethyl-4-methoxyphenone. LC: 100%. MS: m/z=551 (M+H$^+$). $^1$H NMR (CDCl$_3$): δ 8.15 (1H, s), 8.07 (1H, d), 7.86 (1H, d), 7.69 (2H, m), 7.58 (1H, d), 7.02 (1H, d), 4.13 (1H, m), 4.08 (3H, s), 2.98 (2H, m), 1.98 (4H, m), 1.65 (3H, m), 0.94 (2H, t), 0.80 (2H, t).

Example 21

N-Cyclopropyl-N-{1-[4,4-bis(4-fluorophenyl)butyl]piperidin-4-yl}-3-trifluoromethylbenzenesulfonamide (34)

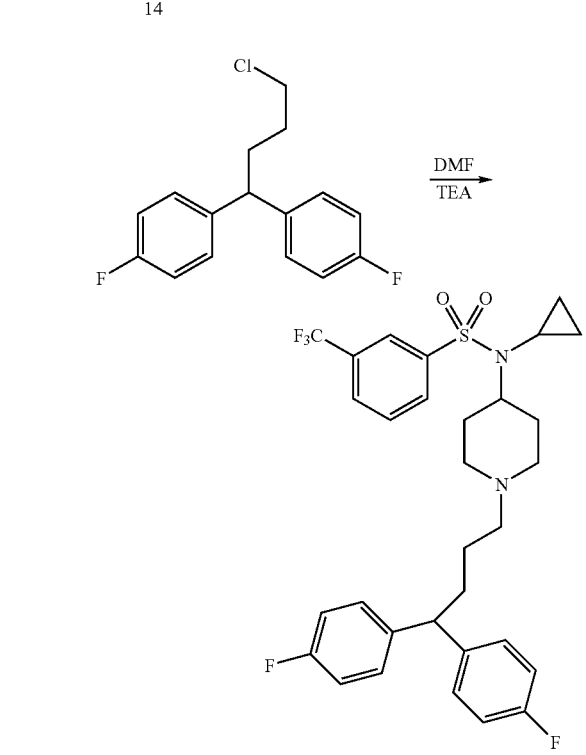

N-Cyclopropyl-N-{1-[4,4-bis(4-fluorophenyl)butyl]piperidin-4-yl}-3-trifluoromethylbenzenesulfonamide (34) was prepared by dissolving N-cyclopropyl-N-piperidin-4-yl-3-trifluoromethylbenzenesulfonamide (110.6 mg, 0.318 mmol) in 10 mL of DMF and followed by the addition of triethylamine (48.3 mg, 0.477 mmol) and bis(4-fluorophenyl)butyl chloride (98.2 mg, 0.350 mmol). The reaction mixture was stirred overnight at 85° C. The crude compound was purified by column chromatography on silica gel (hexane/EtOAc, 7:3) to give the title compound 34 as a yellow sticky solid. $^1$H NMR (CDCl$_3$): δ 8.12 (s, 1H), 8.04 (d, 1H), 7.84 (d, 1H), 7.61 (t, 1H), 7.13 (dd, 4H), 6.94 t, 4H), 3.84 t, 2H), 2.85 (d, 2H), 2.30 (t, 2H), 1.92 (m, 7H), 1.48 (m, 2H), 1.37 (m, 2H), 0.96 (m, 2H), 0.75 (m, 2H). LC: 100%. MS (M+H$^+$): 593.

Similarly, N-cyclopropyl-N-{1-[4,4-bis(4-fluorophenyl)butyl]-piperidin-4-yl}benzenesulfonamide was prepared. LC: 100%. MS: m/z=525.3, 526.2 (M+H$^+$). $^1$H NMR (400 MHz, CDCl$_3$): δ 11.1 (1H, br), 7.81-7.84 (2H, m), 7.59-7.63 (1H, m), 7.5-7.54 (2H, m), 7.12-7.16 (4H, m), 6.95-6.99 (4H, m), 4.08-4.14 (1H, m), 3.86-3.89 (1H, m), 3.48-3.52 (2H, m), 2.92-2.96 (2H, m), 2.57-2.74 (4H, m), 1.95-2.05 (3H, m), 1.7-1.8 (4H, m), 0.9-0.95 (4H, m).

Example 22

N-Cyclopropyl-N-{1-[2-bis(4-fluorophenyl)methoxyethyl]piperidin-4-yl}benzenesulfonamide (37)

N-Cyclopropyl-N-{1-[2-bis(4-fluorophenyl)methoxyethyl]piperidin-4-yl}-3-trifluoromethylbenzenesulfonamide (38)

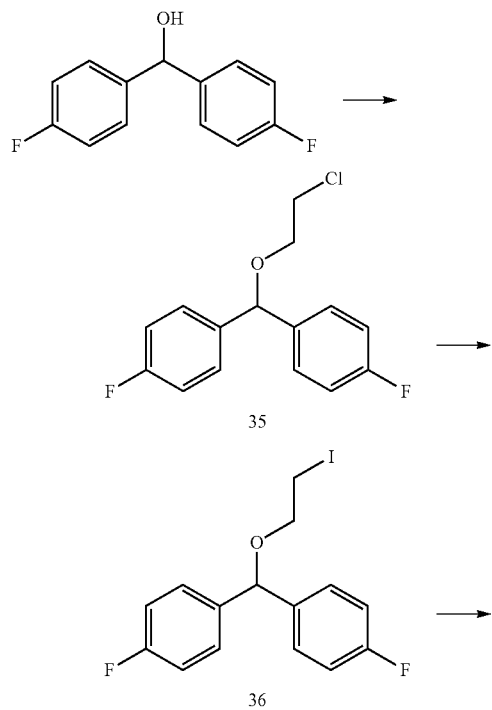

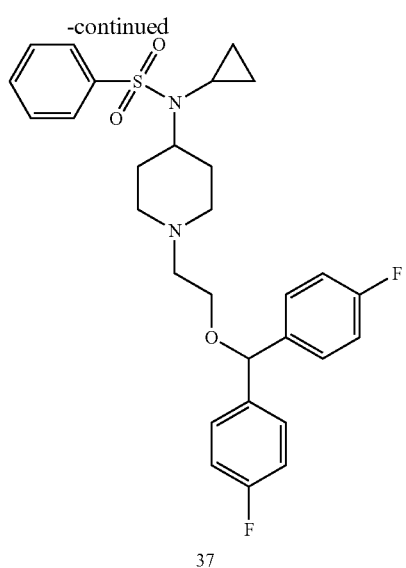

37

36 →

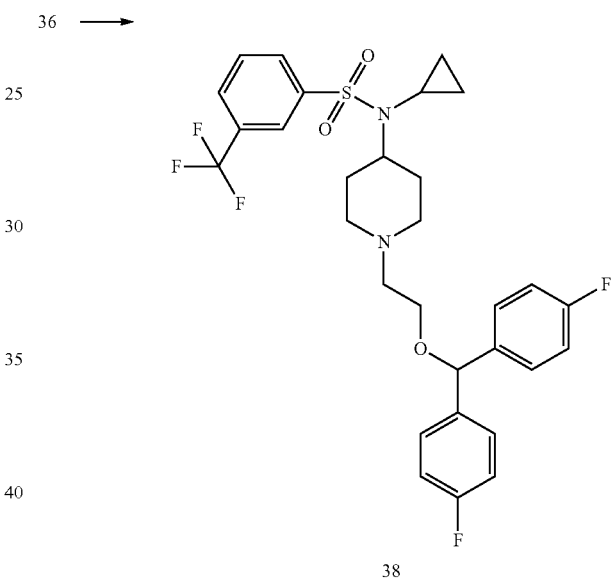

38 a) 1-[Bis(4-fluorophenyl)methoxy]-2-chloroethane (35): A mixture of 2-chloroethanol (2.7 g, 34 mmol), sulfuric acid (0.8 g, 8 mmol) and 5 mL toluene was gently heated to 40° C., and treated with a solution of 4,4'-difluorobenzhydrol (5 g, 23 mmol) in toluene. The resulting solution was heated to 85° C. The reaction mixture was cooled down after 3 hours, diluted with toluene, washed several times with saturated NaHCO$_3$ and water, dried over Na$_2$SO4, and evaporated. The crude 35 was used in the next step without further purification.

b) 1-[Bis(4-fluorophenyl)methoxy]-2-iodoethane (36): 1-[Bis(4-fluorophenyl)methoxy]-2-chloroethane (35) (888 mg, 3 mmol) was dissolved in 5 mL of methyl ethyl ketone, and sodium iodide (1.3 g, 8.4 mmol) was added. The mixture was heated at 80° C. overnight. LC/MS showed a 80% conversion. The solid was filtered off and the filtrate was concentrated. The crude compound 36 was used in next step without further purification.

c) N-Cyclopropyl-N-{1-[2-bis(4-fluorophenyl)methoxyethyl]-piperidin-4-yl}benzenesulfonamide (37): 1-[Bis(4-fluorophenyl)methoxy]-2-iodoethane (36) (393 mg, 1.05 mmol) was dissolved in 3 mL methyl ethyl ketone and this mixture was added to N-cyclopropyl-N-(4-piperidinyl)benzenesulfonamide (200 mg, 0.71 mmol) and K$_2$CO$_3$ (294 mg, 2.2 mmol). The mixture was then heated at 80° C. overnight. Water was added, and EtOAc was used to extract the product. The organic layer was dried over Na$_2$SO$_4$ and evaporated. The crude product was purified by silica gel column eluting with CH$_2$Cl$_2$ and CH$_2$Cl$_2$/EtOAc (4:1) to afford the title compound 37 as a tan oil: $^1$H NMR (CDCl$_3$): δ 7.878-7.849 (d, 2H), 7.600-7.557 (m, 1H), 7.535-7.490 (m, 2H), 7.282-7.231 (m, 4H), 7.029-6.970 (m, 4H), 5.300 (s, 1H), 3.870-3.790 (m, 1H), 3.536-3.506 (t, 2H), 2.928-2.899 (d, 2H), 2.642-2.612 (t, 2H), 2.109-2.053 (t, 2H), 2.000-1.868 (m, 3H), 1.523-1.492 (d, 2H), 0.980-0.940 (m, 2H), 0.760-0.712 (m, 2H). LC: 98%. MS (e/z): 527 (M+H$^+$).

N-Cyclopropyl-N-{1-[2-bis(4-fluorophenyl)methoxyethyl]piperidin-4-yl}-3-trifluoromethylbenzenesulfonamide (38): 1-[Bis(4-fluorophenyl)-methoxy]-2-iodoethane (36) (294 mg, 0.79 mmol) was dissolved in 5 mL of methyl ethyl ketone and the mixture was added to N-cyclopropyl-N-(4-piperidinyl)-3-(trifluoromethyl)benzenesulfonamide (200 mg, 0.57 mmol) and K$_2$CO$_3$ (157 mg, 1.1 mmol). The mixture was then heated at 80° C. overnight. Water was added to the mixture, and EtOAc was used to extract the product. The organic layer was dried over Na$_2$SO$_4$ and evaporated. The crude product was purified by silica gel column eluting with CH$_2$Cl$_2$ and CH$_2$Cl$_2$/EtOAc (4:1) to afford the title compound 38 as a yellow oil. $^1$H NMR (CDCl$_3$): δ 8.127 (s, 1H), 8.061-8.042 (d, 1H), 7.856-7.833 (d, 1H), 7.694-7.655 (t, 1H), 7.282-7.233 (m, 4H), 7.035-6.972 (m, 4H), 5.302 (s, 1H), 3.882-3.806 (t, 1H), 3.551-3.491 (t, 2H), 2.965-2.887 (d, 2H), 2.670-2.605 (t, 2H), 2.127-2.064 (t, 2H), 1.986-1.939 (m, 3H), 1.531-1.493 (d, 2H), 0.992-0.952 (m, 2H), 0.794-0.760 (m, 2H). LC: 100%. MS (e/z): 596 (M+H$^+$).

Example 23

N-Cyclopropyl-N-{1-[2-bis(4-fluorophenyl)methoxyethyl]piperidin-4-yl}-3-trifluoromethylbenzenesulfonamide (38)

a) 1-[Bis(4-fluorophenyl)methoxy]-2-chloroethane (35): A mixture of 2-chloroethanol (2.3 mL, 34 mmol), toluene (5 mL), and sulfuric acid (0.44 mL, 8.2 mmol) was gently heated to 40° C. and treated with a solution of 4,4'-difluorobenzhydrol (5.0 g, 22.7 mmol) in toluene (5 mL). The resulting solution was heated to 85° C. and stirred for 3 hours. After allowing the reaction to return to ambient temperature, it was diluted with toluene and washed with saturated aqueous NaHCO$_3$ solution, washed with water, and dried over sodium sulfate. The solvent was evaporated to yield 6.07 g (95% yield) of the product as a yellow oil.

N-Cyclopropyl-N-{1-[2-bis(4-fluorophenyl)methoxyethyl]-piperidin-4-yl}-3-trifluoromethylbenzenesulfonamide (38): A mixture of 1-[bis(4-fluorophenyl)methoxy]-2-chloroethane (3.0 g, 10.7 mmol), sodium iodide (4.3 g, 28.9 mmol), and MEK (20 mL) was heated at 80° C. for 24 hours. After allowing the reaction to return to ambient temperature it was filtered. To an aliquat of the filtrate (0.78 mmol) was added potassium carbonate (294 mg, 2.13 mmol) and N-cyclopropyl-N-(piperidin-4-yl)-3-trifluoromethylbenzenesulfonamide (0.71 mmol). The mixture was heated at 80° C. for 16 hours. After TLC indicated the reaction to be complete, water and EtOAc were added to the reaction mixture. The phases were separated, and the aqueous phase was extracted twice with EtOAc. The combined organic extracts were washed with water, washed with brine, dried with sodium sulfate, and concentrated. Purification was then carried out using silica gel chromatography as described in Example 22.

Example 24

N-Cyclopropyl-N-{1-[4-(4-fluorophenyl)-4-oxobutyl]piperidin-4-yl}benzenesulfonamide (39)

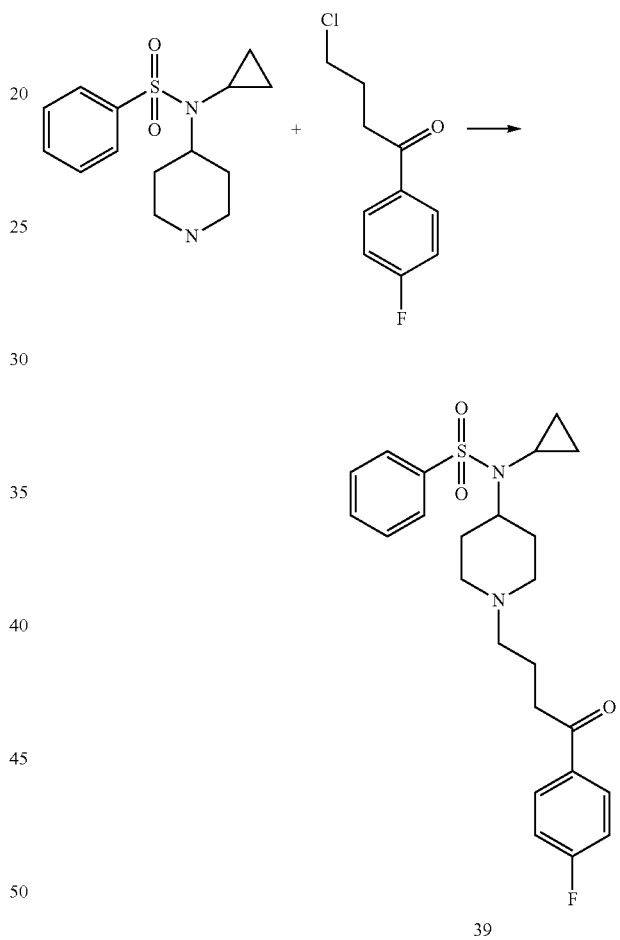

N-Cyclopropyl-N-{1-[4-(4-fluorophenyl)-4-oxobutyl]piperidin-4-yl}benzenesulfonamide (39) was prepared as follows. A mixture of N-cyclopropyl-N-(4-piperidinyl)benzenesulfonamide (100 mg, 0.36 mmol), 4-chloro-4'-fluorobutyrophenone (79 mg, 0.39 mmol) and TEA (54 mg, 0.54 mmol) in DMF was heated at 70° C. for 36 hours. The solvent was removed and the crude product was purified on a silica gel column, eluting first with CH$_2$Cl$_2$, then with EtOAc and 10% MeOH/EtOAc, to afford the title compound 39 as an orange oil. $^1$H NMR (CDCl$_3$): δ 8.006-7.956 (m, 2H), 7.868-7.844 (d, 2H), 7.599-7.556 (m, 1H), 7.535-7.490 (m, 2H), 7.147-7.089 (t, 2H), 3.855-3.773 (m, 1H), 2.950-2.871 (m, 4H), 2.421-2.330 (t, 2H), 2.020-1.772 (m, 7H), 1.518-1.454 (d, 2H), 0.950-0.910 (m, 2H), 0.730-0.682 (m, 2H). LC: 98%. MS (e/z): 446 (M+H⁺).

Example 25

N-Cyclopropyl-N-{1-[3-(2-hydroxyethylamino)hexanoyl]piperidin-4-yl}-3-trifluoromethylbenzenesulfonamide (40)

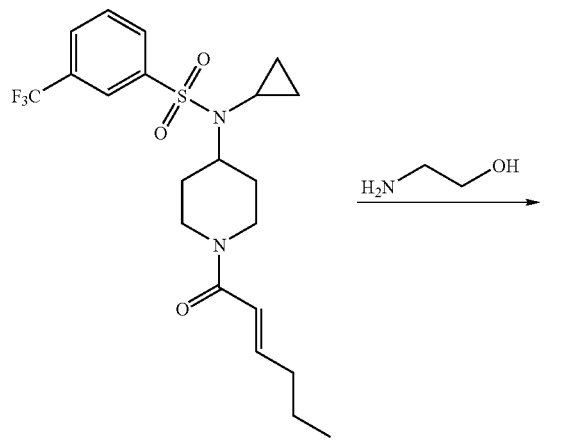

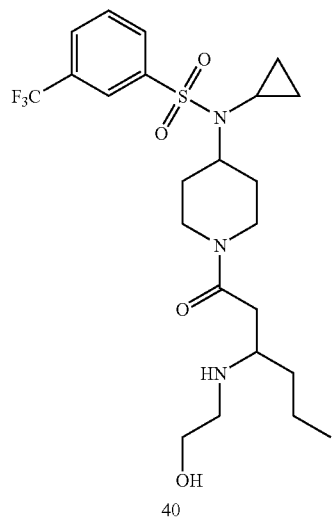

N-Cyclopropyl-N-(1-hex-2-enoyl-piperin-4-yl)-3-trifluoromethyl-benzenesulfonamide (250 mg, 0.56 mmol) and 2-aminoethanol (2 mL) were mixed together in a screw-capped vial and heated to 130° C. on a metal block for 3 days. The cooled mixture was evaporated in vacuum and the residue was purified by column chromatography on silica gel (EtOAc/MeOH/NH₂OH, 100:10:1) to afford the title compound 40 (95 mg). ¹H NMR (CDCl₃): δ 8.21 (d, J=7.9 Hz, 1H), 8.12 (d, J=8.5 Hz, 1H), 8.10 (br s, 1H), 7.91 (dd, J=7.76, 7.78 Hz, 1H), 4.43 (d, J=13.0 Hz, 1H), 4.10 (m, 1H), 3.90 (d, J=12.1 Hz, 1H), 3.55 (m, 2H), 3.25 (m, 1H), 3.05 (m, 1H), 2.86 (m, 2H), 2.60 (m, 3H), 2.00 (m, 1H), 1.82-1.21 (m, 8H), 0.85 (m, 5H), 0.75 (m, 2H). LC: 100%. MS: 506.2 (M+1).

Example 26

N-Cyclopropyl-N-[1-(3-thiomorpholin-4-yl-hexanoyl)piperidin-4-yl]-3-trifluoromethylbenzenesulfonamide (41)

N-Cyclopropyl-N-[1-(3-thiomorpholin-4-yl-hexanoyl)piperidin-4-yl]-3-trifluoromethylbenzenesulfonamide (41) was prepared as follows. N-cyclopropyl-N-(1-hex-2-enoyl-piperidin-4-yl)-3-trifluoromethyl-benzenesulfonamide (30) (250 mg, 0.56 mmol) and thiomorpholine (2 mL) were heated together at 130° C. for 3 days in a sealed Reacti-vial. The vial was cooled in ice and then the cooled mixture was evaporated to dryness in vacuo in a Speed-Vac®. The residue was chromatographed over flash silica eluting with ethyl acetate:hexane (1:1) to give the title compound 41 (110 mg, 36%) as a white solid. LC: 100%. MS: m/z=548.3, 549.3 (M+H). ¹H NMR (400 MHz, CDCl₃): (1:1 mixture of rotamers) δ 8.15 (1H, s), 8.06 (1H, d, J=7.5 Hz), 7.88 (1H, d, J=7.5 Hz), 7.70 (1H, t, J=7.5 Hz), 4.73 (1H, d, J=17.7 Hz), 4.10 (1H, m), 3.95 (1H, d, J=17.7 Hz), 3.05 (2H, m), 2.84 (2H, m), 2.74 (2H, m), 2.67-2.43 (6H, m), 2.15 (1H, m), 1.96 (1H, m), 1.75 (3H, m), 1.52-1.22 (4H, m), 0.98 (1H, m), 0.93-0.70 (6H, m).

Example 27

N-Cyclopropyl-N-[1-(3-morpholin-4-yl-hexanoyl)piperidin-4-yl]-3-trifluoromethylbenzenesulfonamide (42)

N-Cyclopropyl-N-[1-(3-morpholin-4-yl-hexanoyl)piperidin-4-yl]-3-trifluoromethylbenzenesulfonamide (42) was prepared by reacting N-cyclopropyl-N-(1-hex-2-enoyl-piperidin-4-yl)-3-trifluoromethylbenzene-sulfonamide (30) (250 mg, 0.56 mmol) and morpholine (2 mL) as described in Example 26 above. The residue was chromatographed over flash silica eluting with ethyl acetate:methanol:ammonia (100:10:1) to give the title compound 42 (120 mg, 40%) as a white solid. LC: 100%. MS: m/z=532.3, 533.3 (M+H). ¹H NMR (400 MHz, CDCl₃): (1:1 mixture of rotamers) δ 8.15 (1H, s), 8.07 (1H, d, J=7.5 Hz), 7.88 (1H, d, J=7.5 Hz), 7.70 (1H, t, J=7.5 Hz), 4.75 (1H, d, J=15 Hz), 4.10 (1H, m), 3.96 (1H, d, J=15 Hz), 3.70 (4H, m), 3.09 (2H, m), 2.64-2.44 (6H, m), 2.20 (1H, dd, J=8.8 Hz), 1.99 (1H, m), 1.50-1.25 (4H, m), 1.02-0.70 (7H, m).

Example 28

N-Cyclopropyl-N-[1-(3-pyrrolidin-1-ylhexanoyl)piperidin-4-yl]-3-trifluoromethylbenzenesulfonamide (43)

N-Cyclopropyl-N-[1-(3-pyrrolidin-1-ylhexanoyl)piperidin-4-yl]-3-trifluoromethylbenzenesulfonamide (43) was prepared by reacting N-cyclopropyl-N-(1-hex-2-enoyl-piperidin-4-yl)-3-trifluoromethyl-benzenesulfonamide (30) (250 mg, 0.56 mmol) and pyrrolidine (2 mL) as described in Example 26 above. The residue was chromatographed over flash silica eluting with ethyl acetate:methanol:ammonia (100:10:1) to give the title compound 43 as a white solid (140 mg, 48%). LC: 98.9%. m/z=516.3, 517.3 (M+H). ¹H NMR (400 MHz, CDCl₃): (1:1 mixture of rotamers) δ 8.14 (1H, s), 8.05 (1H, d, J=7.5 Hz), 7.86 (1H, d, J=7.5 Hz), 7.70 (1H, t, J=7.5 Hz), 4.75 (1H, d, J=15 Hz), 4.10 (1H, m), 3.97 (1H, d, J=15 Hz), 3.05 (2H, m), 2.65-2.45 (6H, m), 2.35 (1H, m), 1.96 (1H, m), 1.85-1.30 (16H, m), 0.98 (1H, m), 0.92-0.70 (6H, m).

Example 29

N-Cyclopropyl-N-[1-(3-dimethylaminohexanoyl)piperidin-4-yl]-3-trifluoromethylbenzenesulfonamide (44)

N-cyclopropyl-N-(1-hex-2-enoyl-piperidin-4-yl)-3-trifluoromethyl-benzenesulfonamide (30) (250 mg, 0.56 mmol) and dimethylamine in methanol (2M, 3 mL) were heated in a sealed React-vial at 120° C. for 24 hours. The cooled solution was evaporated to dryness in vacuo and the residue chromatographed over flash silica eluting with ethyl acetate (3× column lengths) followed by ethyl acetate:methanol:ammonia (100:10:1) to give the title compound 44 (150 mg, 34%) as a white solid. TLC (SiO$_2$, ethyl acetate: methanol: ammonia, 100:10:1) Rf=0.15 (UV detection, Dragendorff's reagent). LC: 100%. MS: m/z=490.3, 491.2 (M+H). $^1$H NMR (400 MHz, CDCl$_3$): (1:1 mixture of rotamers) δ 8.14 (1H, s), 8.07 (1H, d, J=8 Hz), 7.88 (1H, d, J=8 Hz), 7.70 (1H, t, J=8 Hz), 4.74 (1H, d, J=12 Hz), 4.07 (1H, m), 3.95 (1H, d, J=12 Hz), 3.05 (2H, m), 2.50 (2H, m), 2.24 (6H, s), 2.15 (1H, 2d), 1.96 (1H, m), 1.86-1.69 (3H, m), 1.58-1.24 (6H, m), 0.98 (1H, m), 0.90 (3H, t, J=8 Hz), 0.87-0.75 (3H, m).

Example 30

(3S) N-[1-(3-Amino-5-methylhexanoyl)piperidin-4-yl]-N-cyclopropyl-3-trifluoromethylbenzenesulfonamide (46)

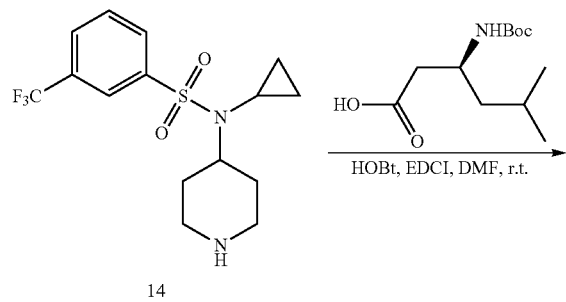

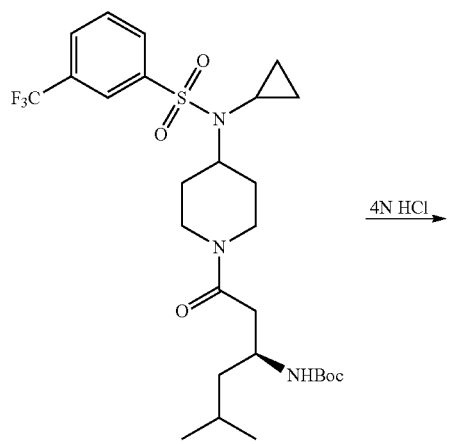

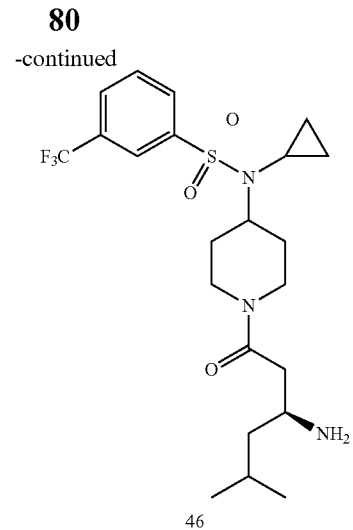

a) (3S) 1-{4-[Cyclopropyl-(3-trifluoromethylbenzenesulfonyl)-amino]piperidine-1-ethanoyl}-3-methylbutyl carbamic acid tert-butyl ester (45): To a solution of N-cyclopropyl-N-(piperidin-4-yl)-3-trifluoromethylbenzenesulfonamide (0.287 mmol, 100 mg) in DMF (5 mL) was added HOBt (0.287 mmol, 39 mg), EDCI (0.287 mmol, 55 mg) and BOC-L-b-homoleucine (0.287 mmol, 70 mg) at room temperature. The resulting mixture was kept shaken at room temperature overnight. EtOAc (20 mL) was then added to the mixture and the mixture was washed with 10% HCl (20 mL), saturated NaHCO$_3$ (20 mL) and water (10 mL). The organic layer was dried over Na$_2$SO$_4$ and concentrated to dryness. The crude product was purified through a column of silica gel with a gradient of 25% to 100% EtOAc in hexanes to afford (3S) 1-{4-[cyclopropyl-(3-trifluoromethylbenzenesulfonyl)amino]piperidine-1-ethanoyl}-3-methylbutyl carbamic acid tert-butyl ester (45).

b) (3S) N-[1-(3-Amino-5-methylhexanoyl)-piperidin-4-yl]-N-cyclopropyl-3-trifluoromethylbenzenesulfonamide (46): The above compound 45 was dissolved in 4 N HCl for 3 hours at the room temperature. The mixture was then evaporated to dryness to give the crude product, which was purified through a column of silica gel with a gradient of 30% EtOAc in hexanes to afford the title compound 46 (45 mg). $^1$H NMR (CDCl$_3$): δ 8.21 (d, J=8.1 Hz, 1H), 8.18 (br s, 1H), 8.04 (d, J=8.1 Hz, 1H), 7.87 (dd, J=7.84, 7.86 Hz, 1H), 4.63 (m, 1H), 4.15 (m, 1H), 3.95 (d, J=12.8 Hz, 1H), 3.59 (m, 1H), 3.23 (m, 1H), 2.86 (dt, J=3.4, 17.4 Hz, 1H), 2.60 (m, 2H), 2.07-1.51 (m, 8H), 1.00 (m, 6H), 0.93 (m, 2H), 0.80 (m, 2H). LC: 100%. MS: 476.2 (M+1).

The following compound was prepared similarly:

(3S) N-[1-(3-Amino-4-methylpentanoyl)piperidin-4-yl]-N-cyclopropyl-3-trifluoromethylbenzenesulfonamide: LC: 100%. MS: m/z=462.3, 463.3 (M+H$^+$). $^1$H NMR (400 MHz, MeOH-d$_4$): δ 8.21 (1H, d, J=8.1 Hz), 8.17 (1H, s), 8.03 (1H, d, J=7.9 Hz), 7.87 (1H, dd, J=7.7, 7.9 Hz), 4.63-4.66 (1H, m), 4.11-4.18 (1H, m), 3.96-4.03 (1H, m), 3.38-3.45 (1H, m), 3.11-3.17 (1H, m), 2.82-2.9 (1H, m), 2.54-2.68 (m, 2H), 1.65-2.05 (6H, m), 1.03-1.07 (6H, m), 0.91-0.94 (2H, m), 0.79-0.81 (2H, m).

Example 31

(3S) N-Cyclopropyl-N-[1-(5-methyl-3-methylamino-hexanoyl)piperidin-4-yl]-3-trifluoromethylbenzene-sulfonamide (47)

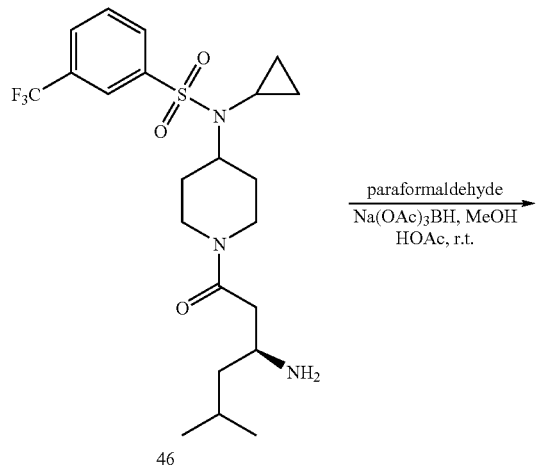

To a solution of a compound 46 prepared in Example 30 (0.325 mmol, 150 mg) in methanol (5 mL) was added paraformaldehyde (0.813 mmol, 25 mg), Na(OAc)$_3$BH and a catalytic amount of HOAc at room temperature. The resulting mixture was kept stirred at room temperature overnight. Then EtOAc (20 mL) was added to the mixture and the mixture was washed with saturated NaHCO$_3$ and water. The organic layer was dried over Na$_2$SO$_4$ and concentrated to dryness. The crude product was purified through a column of silica gel with a gradient of 0% to 50% MeOH in DCM to afford the title compound 47. $^1$H NMR (CDCl$_3$): δ 8.21 (d, J=8.1 Hz, 1H), 8.18 (br s, 1H), 8.04 (d, J=8.1 Hz, 1H), 7.87 (dd, J=7.84, 7.86 Hz, 1H), 4.63 (m, 1H), 4.15 (m, 1H), 3.95 (m, 1H), 3.52 (m, 1H), 3.23 (m, 1H), 2.90-2.55 (m, 3H), 2.70 (d, J=5.4 Hz, 3H), 2.07-1.54 (m, 8H), 1.00 (m, 6H), 0.92 (m, 2H), 0.80 (m, 2H). LC: 100%. MS: 490.2 (M+1).

The following compound was prepared similarly:

(3S) N-Cyclopropyl-N-[1-(4-methyl-3-methylaminopen-tanoyl)-piperidin-4-yl]-3-trifluoromethylbenzene-sulfonamide: LC: 100%. MS: m/z=476.2, 477.2 (M+H$^+$). $^1$H NMR (400 MHz, MeOH-d$_4$): δ 8.21 (1H, d, J=7.7 Hz), 8.17 (1H, s), 8.03 (1H, d, J=7.9 Hz), 7.87 (1H, dd, J=7.8, 7.9 Hz), 4.61-4.65 (1H, m), 4.11-4.18 (1H, m), 3.99-4.04 (1H, m), 3.36-3.43 (1H, m), 3.12-3.19 (1H, m), 2.82-2.9 (1H, m), 2.75 (1.5H, s), 2.73 (1.5H, s), 2.64-2.69 (m, 2H), 2.16-2.21 (1H, m), 2.06-2.09 (1H, m), 1.61-1.95 (4H, m), 1.02-1.09 (6H, m), 0.92-0.94 (2H, m), 0.79-0.83 (2H, m).

Example 32

N-Cyclopropyl-N-{1-[3-(4-methylpiperazin-1-yl) hexanoyl]piperidin-4-yl}-3-trifluoromethylbenzene-sulfonamide (31)

N-Cyclopropyl-N-{1-[3-(4-methylpiperazin-1-yl)hex-anoyl]piperidin-4-yl}-3-trifluoromethylbenzene-sulfonamide (31) was prepared by reacting N-cyclopropyl-N-(1-hex-2-enoyl-piperidin-4-yl)-3-trifluoromethyl-benzenesulfonamide (30) (250 mg, 0.56 mmol) and N-methyl-piperazine (2 mL) as described in Example 26 above. The residue was chromatographed over flash silica eluting with ethyl acetate:methanol:ammonia (100:10:1) to give the title compound 31 (120 mg, 40%) as a white solid. LC: 100%. MS: m/z=545.3, 546.3 (M+H). $^1$H NMR (400 MHz, CDCl$_3$): (1:1 mixture of rotamers) δ 8.14 (1H, s), 8.07 (1H, d, J=7.5 Hz), 7.88 (1H, d, J=7.5 Hz), 7.70 (1H, t, J=7.5 Hz), 4.74 (1H, d, J=13 Hz), 4.09 (1H, t, J=13 Hz), 3.95 (1H, d, J=13 Hz), 3.08 (2H, m), 2.67-2.33 (9H, m), 2.26 (3H, s), 2.15 (1H, dd, J=8.8 Hz), 1.96 (1H, m), 1.85-1.65 (3H, m), 1.52-1.22 (4H, m), 0.98 (1H, m), 0.98-0.70 (6H, m).

Example 33

N-Cyclopropyl-N-{1-[3-(2-hydroxyethylamino)hex-anoyl]piperidin-4-yl}-3-trifluoromethylbenzene-sulfonamide (40)

N-Cyclopropyl-N-{1-[3-(2-hydroxyethylamino)hex-anoyl]piperidin-4-yl}-3-trifluoromethylbenzene-sulfonamide (40) was prepared by reacting N-cyclopropyl-N-(1-hex-2-enoyl-piperidin-4-yl)-3-trifluoromethyl-benzenesulfonamide (250 mg, 0.56 mmol) and ethanolamine (2 mL) as described in Example 26 above. The reaction mixture was cooled and partitioned between ether (100 mL) and 1M sodium hydroxide solution (100 mL). The organic phase was separated, dried (MgSO$_4$) and the solvent evaporated to dryness in vacuo to leave a colourless gum. The residue was chromatographed over flash silica eluting with ethyl acetate: methanol:ammonia (100:10:1) to give the free base 40 (100 mg). This was converted to the fumarate salt (95 mg, 27%) which was a white solid. LC: 100%. MS: m/z=506.2, 507.3, 508.2 (M+H). $^1$H NMR (400 MHz, DMSO-d$_6$): (1:1 mixture of rotamers) δ 8.22 (1H, d, J=7.5 Hz), 8.13 (2H, m), 7.92 (1H, t, J=7.5 Hz), 6.47 (1H, s), 4.43 (1H, d, J=13.3 Hz), 4.10 (1H, t, J=13.3 Hz), 3.88 (1H, d, J=13.3 Hz), 3.55 (2H, m), 3.25 (1H, m), 3.05 (1H, t, J=13.3 Hz), 2.85 (2H, m), 2.70-2.50 (3H, m), 1.96 (1H, m), 1.80-1.20 (8H, m), 0.88-0.65 (7H, m).

Example 34

N-Cyclopropyl-N-{1-[3-(piperidin-1-yl)hexanoyl] piperidin-4-yl}-3-trifluoromethylbenzene-sulfonamide (32)

N-Cyclopropyl-N-{1-[3-(piperidin-1-yl)hexanoyl]piperi-din-4-yl}-3-trifluoromethylbenzenesulfonamide (32) was prepared by reacting N-cyclopropyl-N-(1-hex-2-enoyl-piperidin-4-yl)-3-trifluoromethyl-benzenesulfonamide (30) (250 mg, 0.56 mmol) and piperidine (2 mL) as described in Example 26 above. The residue was chromatographed over flash silica eluting with ethyl acetate:methanol:ammonia (100:10:1) to give the title compound 32 (100 mg, 34%) as a white solid. LC: 100%. MS: m/z=530.3, 531.3, 532.3 (M+H). $^1$H NMR (400 MHz, CDCl$_3$): (1:1 mixture of rotamers) δ 8.13 (1H, s), 8.06 (1H, d, J=7.5 Hz), 7.86 (1H, d, J=7.5 Hz), 7.70 (1H, t, J=7.5 Hz), 4.75 (1H, d, J=15 Hz), 4.09 (1H, m), 3.97 (1H, d, J=15 Hz), 3.10-2.92 (2H, m), 2.65-2.35 (6H, m), 2.15 (1H, m), 1.95 (1H, m), 1.90-1.70 (3H, m), 1.65-1.20 (11H, m), 0.95 (1H, m), 0.92-0.70 (6H, m).

Example 35

N-[1-(1-Aminocyclopentan-1-carbonyl)piperidin-4-yl]-N-cyclopropyl-3-trifluoromethylbenzenesulfonamide (48)

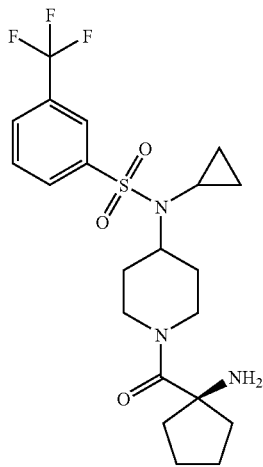

N-Cyclopropyl-N-piperidin-4-yl-3-trifluoromethyl-benzenesulfonamide (14) (0.400 g, 1.15 mmol) was taken up in 10 mL of dry DMF. To this mixture, HOBt (0.154 g, 1.15 mmol), EDCI (0.218 g, 1.15 mmol), and 1-tert-butoxycarbonylaminocyclopentane-1-carboxylic acid (0.263 g, 1.15 mmol) were added. The mixture was allowed to stir at room temperature for 16 hours. The reaction mixture was concentrated to dryness under reduced pressure and the crude material was chromatographed on silica eluting with 25% ethyl acetate/hexane. The combined product fractions were concentrated to dryness and the pure BOC-protected material was deprotected in 40 mL of ethyl acetate/concentrated HCl (19:1). The solvent was removed leaving a white solid material. This material was triturated with diethyl ether and vacuum filtered affording the desired sulfonamide (48) as the HCl-salt. LC: 97%. MS (e/z): 460 (M+H$^+$). $^1$H NMR of salt (CD$_3$OD): δ 8.02 (m, 2H), 7.83 (d, 1H, J=7.86 Hz), 7.66 (t, 1H, J=7.86 Hz), 4.01 (m, 2.5H), 2.80 (bs, 1.5H), 2.11 (m, 2H), 1.7-2.0 (m, 10H), 1.51 (m, 2H), 0.60 (m, 2H), 0.50 (m, 2H).

Similarly, N-cyclopropyl-N-[1-(1-phenylaminocyclohexan-1-oyl)piperidin-4-yl]-3-trifluoromethylbenzenesulfonamide was prepared: LC: 100%. MS: m/z=550.2, 551.2 (M+H$^+$). $^1$H NMR (400 MHz, CDCl$_3$): δ 8.07 (1H, s), 7.98 (1H, d, J=7.5 Hz), 7.84 (1H, d, J=7.7 Hz), 7.66 (1H, dd, J=7.8 & 7.9 Hz), 7.08-7.12 (2H, m), 6.64-6.68 (1H, m), 6.52-6.55 (2H, m), 5.04-5.14 (1H, m), 4.84-4.92 (1H, m), 3.92-3.98 (2H, m), 2.82-2.9 (1H, m), 2.42-2.48 (1H, m), 1.82-2.14 (4H, m), 1.62-1.68 (2H, m), 1.26-1.44 (6H, m), 0.48-0.78 (4H, m).

Example 36

N-Cyclopropyl-N-[1-(N-methylpyrrolidin-2-carbonyl)piperidin-4-yl]-3-trifluoromethylbenzenesulfonamide (49)

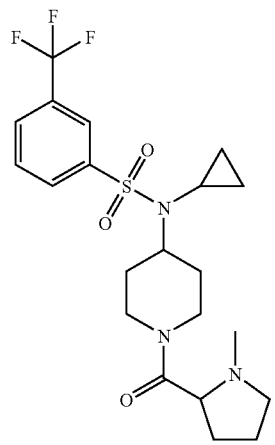 [SMILES: CN1CCCC1C(=O)N1CCC(N(C2CC2)S(=O)(=O)c2cccc(C(F)(F)F)c2)CC1]

N-Cyclopropyl-N-piperidin-4-yl-3-trifluoromethyl-benzenesulfonamide (14) (0.400 g, 1.15 mmol) was taken up in 10 mL of dry DMF. To this mixture, HOBt (0.154 g, 1.15 mmol), EDCI (0.218 g, 1.15 mmol), and N-methylproline (0.148 g, 1.15 mmol) were added. The mixture was allowed to stir at room temperature for 16 hours. The reaction mixture was concentrated to dryness under reduced pressure and the crude material was chromatographed on silica eluting with 25% ethyl acetate/hexane. The combined product fractions were concentrated to dryness and taken up in 20 mL of MeOH. To this mixture, 1.1 eq of fumaric acid was added. The solvent was removed and the remaining material was triturated with diethyl ether. After vacuum filtration, the desired product (49) was obtained as the fumaric acid salt. LC: 98%. MS (e/z): 460 (M+H$^+$). $^1$H NMR of salt (DMSO-d$_6$): δ 8.20 (m, 1H), 8.12 (m, 2H), 7.90 (t, 1H, J=7.82 Hz), 4.40 (m, 1H), 4.10 (m, 2H), 3.07 (m, 2H), 2.65 (m, 1.5H), 2.40 (s, 1.5H), 2.31 (d, 3H), 2.05 (m, 1H), 1.99 (m, 1H), 1.66 (m, 5H), 1.50 (m, 2H), 0.75 (m, 4H).

Similarly, the following compounds were prepared:

N-Cyclopropyl-N-[1-(1,2,3,4-tetrahydroisoquinolin-3-carbonyl)piperidin-4-yl]-3-trifluoromethylbenzenesulfonamide: LC: 100%. MS: m/z=508.3, 509.3 (M+H$^+$). $^1$H NMR (400 MHz, DMSO-d$_6$): δ 10.7 (1H, br), 9.4 (1H, br), 8.22-8.25 (1H, m), 8.12-8.16 (2H, m), 7.9-7.94 (1H, m), 7.22-7.28 (4H, m), 4.72-4.82 (1H, m), 4.42-4.44 (1H, m), 4.16-4.32 (3H, m), 3.9-3.94 (1H, m), 3.15-3.22 (2H, m), 2.86-2.96 (1H, m), 2.74-2.8 (1H, m), 1.98-2.04 (1H, m), 1.48-1.82 (4H, m), 0.74-0.86 (4H, m).

N-Cyclopropyl-N-[1-(piperidin-2-oyl)piperidin-4-yl]-3-trifluoromethylbenzenesulfonamide: LC: 100%. MS: m/z=460.2, 461.2 (M+H$^+$). $^1$H NMR (400 MHz, MeOD): δ 8.164 (2H, t), 7.998 (1H, d, J=6.8 Hz), 7.837 (1H, t), 4.536 (1H, d), 4.327-4.218 (1H, m), 4.181-4.087 (1H, m), 3.861 (1H, d), 3.452 (1H, d), 3.178 (1H, t), 3.016 (1H, t), 2.691 (1H, t), 2.125-1.995 (2H, m), 1.995-1.760 (4H, m), 1.756-1.493 (6H, m), 0.891 (2H, s), 0.770 (2H, s).

Example 37

Compounds of the invention described exhibit an IC$_{50}$ value of from about 0.09 μM to about 10 μM when tested in the calcium mobilization and/or electrophysiological assays for N-type calcium channel blocking activity, which is described in detail in paragraph 0200 supra under the heading "FLIPR Calcium Mobilization Assay for N-type Calcium Channel". Some compounds described have been tested in the calcium mobilization and/or electrophysiological assays for L-type calcium channel blocking activity, which is described in detail in paragraph 0201 supra under the heading "FLIPR Calcium Mobilization Assay for L-type Calcium Channel". and they exhibit an IC$_{50}$ value of from about 0.45 μM to about >20 μM. Representative values are presented in TABLE 2.

TABLE 2

Evaluation of the tested compounds as N-type calcium channel (NTCC) blockers and L-type calcium channel (LTCC) blockers after a calcium mobilization and/or electrophysiological in vitro assay

| COMPOUND | NTCC IC$_{50}$ (μM) | LTCC IC$_{50}$ (μM) |
|---|---|---|
| N-cyclopropyl-N-{1-[4,4-bis(4-fluorophenyl)butyl]-piperidin-4-yl}-3-trifluoromethylbenzenesulfonamide | 0.11 | 3.78 |
| N-{1-[2-amino-3-(4-fluorophenyl)propionyl]-piperidin-4-yl}-N-cyclopropyl-3-trifluoromethyl-benzenesulfonamide | 0.18 | 8.60 |
| N-cyclopropyl-N-[1-(3-thiomorpholin-4-ylhexanoyl)piperidin-4-yl]-3-trifluoromethyl-benzenesulfonamide | 0.28 | 10-20 |
| N-cyclopropyl-N-{1-[(3-trifluoromethyl-4-methoxy)benzoyl]piperidin-4-yl}-3-trifluoromethylbenzenesulfonamide | 0.30 | 4.57 |
| (2S) N-cyclopropyl-N-[1-(4-methyl-2-methylaminopentanoyl)piperidin-4-yl]-3-trifluoromethylbenzenesulfonamide | 0.36 | 10.02 |
| N-cyclopropyl-N-[1-(4-propylphenylsulfonyl)-piperidin-4-yl]-3-trifluoromethyl-benzenesulfonamide | 0.44 | 0.94 |
| N-cyclopropyl-N-(1-hex-2-enoylpiperidin-4-yl)-3-trifluoromethylbenzenesulfonamide | 1.21 | |
| N-cyclopropyl-N-{1-[4,4-bis(4-fluorophenyl)but-3-enoyl]piperidin-4-yl}benzenesulfonamide | 1.24 | 2.59 |
| N-cyclopropyl-N-{1-[4,4-bis(4-fluorophenyl)butanoyl]piperidin-4-yl}benzenesulfonamide | 1.09 | 3.24 |
| (2S) N-[1-(2-amino-4-methylpentanoyl)piperidin-4-yl]-N-cyclopropyl-benzenesulfonamide | 4.28 | 10-20 |
| N-cyclopropyl-N-{1-[4-(4-fluorophenyl)-4-oxobutanoyl]piperidin-4-yl}benzenesulfonamide | 6.21 | |
| (2S) N-(2-methoxyethyl)-N-[1-(4-methyl-2-methylamino-pentanoyl)piperidin-4-yl]-3-trifluoromethylbenzenesulfonamide | 1.22 | |
| (2S) N-cyclopropyl-N-[1-(4-methyl-2-methylaminopentanoyl)-piperidin-4-yl]-3-fluorobenzenesulfonamide | 4.66 | |
| N-cyclopropyl-N-{1-[4,4-bis(4-fluorophenyl)butanoyl]piperidin-4-yl}-3-fluorobenzenesulfonamide | 0.97 | 1.43 |
| (2S) N-i-butyl-N-[1-(4-methyl-2-methylaminopentanoyl)piperidin-4-yl]-3-trifluoromethylbenzenesulfonamide | 0.95 | 9.12 |
| (2S) N-i-pentyl-N-[1-(4-methyl-2-methylaminopentanoyl)piperidin-4-yl]-3-trifluoromethylbenzenesulfonamide | 1.26 | |
| (2S) N-cyclopropyl-N-[1-(4-methyl-2-methylaminopentanoyl)-piperidin-4-yl]-3-methoxybenzenesulfonamide | 7.29 | |
| (2S) N-[1-(4-methyl-2-methylaminopentanoyl)piperidin-4-yl]-N-(tetrahydrofuran-2-yl)methyl-3-trifluoromethylbenzenesulfonamide | 5.06 | |
| (2S) N-cyclopropyl-N-[1-(4-methyl-2-methylaminopentanoyl)-piperidin-4-yl]-3-difluoromethoxybenzenesulfonamide | 2.44 | |
| (2S) N-cyclopropyl-N-[1-(4-methyl-2-methylaminopentanoyl)-piperidin-4-yl]-3-cyanobenzenesulfonamide | 4.27 | |
| (2S) N-cyclopropyl-N-[1-(4-methyl-2-methylaminopentanoyl)-piperidin-4-yl]-3-chlorobenzenesulfonamide | 2.63 | |
| (2S) N-cyclopropyl-N-[1-(4-methyl-2-methylaminopentanoyl)-piperidin-4-yl]-3-methylbenzenesulfonamide | 8.29 | |
| (2S) N-methyl-N-[1-(4-methyl-2-methylaminopentanoyl)piperidin-4-yl]-3-trifluoromethylbenzenesulfonamide | 0.39 | 5.12 |
| (2S) N-cyclopropyl-N-[1-(4-methyl-2-methylaminopentanoyl)-piperidin-4-yl]-3-nitrobenzenesulfonamide | 3.62 | |
| (2S) N-(2-hydroxyethyl)-N-[1-(4-methyl-2-methylaminopentanoyl)-piperidin-4-yl]-3-trifluoromethylbenzenesulfonamide | 2.23 | |
| (2S) N-cyclopropylmethyl-N-[1-(2-methylamino-4-methyl-pentanoyl)-piperidin-4-yl]-3-trifluoromethylbenzenesulfonamide | 1.31 | |
| (2S) N-cyclopentyl-N-[1-(4-methyl-2-methylamino-pentanoyl)-piperidin-4-yl]-3-trifluoromethylbenzenesulfonamide | 1.56 | |
| (2S) N-isopropyl-N-[1-(4-methyl-2-methylaminopentanoyl)-piperidin-4-yl]-3-trifluoromethylbenzenesulfonamide | 0.87 | >20 |
| (2S) N-[1-(4-methyl-2-methylaminopentanoyl)piperidin-4-yl]-N-(tetrahydrofuran-3-yl)-3-trifluoromethylbenzenesulfonamide | 1.84 | |
| N-cyclopropyl-N-[1-(4-quinolinylmethyl)piperidin-4-yl]-3-trifluoromethyl-benzenesulfonamide | 0.86 | 1.70 |
| N-cyclopropyl-N-{1-[2-bis(4-fluorophenyl)methoxyethyl]piperidin-4-yl}-3-trifluoromethylbenzenesulfonamide | 0.78 | 2.23 |
| N-[1-(1-aminocyclopentan-1-carbonyl)piperidin-4-yl]-N-cyclopropyl-3-trifluoromethylbenzenesulfonamide | 1.08 | |
| N-cyclopropyl-N-[1-(1,2,3,4-tetrahydroisoquinolin-3-carbonyl)piperidin-4-yl]-3-trifluoromethylbenzenesulfonamide | 1.58 | |
| N-cyclopropyl-N-[1-(N-methylpyrrolidin-2-carbonyl)piperidin-4-yl]-3-trifluoromethylbenzenesulfonamide | 1.38 | |
| N-cyclopropyl-N-[1-(2-methylamino-3-o-tolylpropionyl)piperidin-4-yl]-3-trifluoromethylbenzenesulfonamide | 0.39 | 10-20 |
| (2R) N-[1-(2-amino-2-cyclohexylethanoyl)piperidin-4-yl]-N-cyclopropyl-3-trifluoromethylbenzenesulfonamide | 0.44 | >20 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

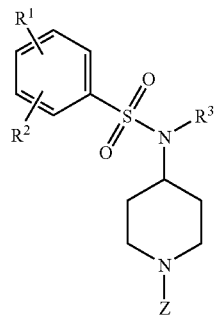

or a pharmaceutically acceptable salt thereof, wherein:
$R^1$ and $R^2$ are each independently selected from the group consisting of hydrogen, alkyl, haloalkyl, halogen, alkoxy, haloalkoxy, cyano, nitro, amino, and hydroxy;
$R^3$ is selected from the group consisting of alkyl, alkenyl, cycloalkyl, cycloalkylalkyl, alkoxyalkyl, hydroxyalkyl, 2-tetrahydrofuranyl, 3-tetrahydrofuranyl, 2-tetrahydrofuranyl alkyl, 3-tetrahydrofuranylalkyl, alkylsulfonylaminoalkyl, and aminocarbonylalkyl;
Z is selected from the group consisting of $Z^1$, $Z^3$, and $Z^4$, wherein

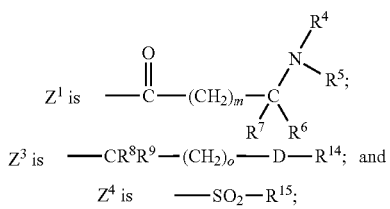

$R^4$ and $R^5$ are each independently selected from the group consisting of hydrogen, alkyl, alkenyl, hydroxyalkyl, haloalkyl, alkylthiol, aminoalkyl and phenyl; or $R^4$ and $R^5$ together with the nitrogen atom to which they are attached form a 5- or 6-membered heterocyclic ring wherein one or more carbon atoms of the heterocyclic ring are optionally replaced with $NR^{16}$, O, or S, wherein $R^{16}$ is hydrogen or $C_{1-3}$ alkyl;
$R^6$ is hydrogen and $R^7$ is selected from the group consisting of alkyl;
hydroxyalkyl;
alkoxyalkyl;
haloalkyl;
aminoalkyl;
cycloalkyl;
phenyl optionally substituted with one or two substituents independently selected from the group consisting of alkyl, cycloalkyl, halogen, cyano, amino, alkylamino, dialkylamino, hydroxy, nitro, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, haloalkyl, and alkoxy; and
benzyloxyalkyl; or
$R^6$ and $R^7$ together with the carbon atom to which they are attached form a $C_{3-7}$cycloalkyl group, or
$R^7$ is hydrogen, $R^4$ is hydrogen or $C_{1-3}$alkyl, and $R^5$ and $R^6$ together form a bridge $-CH_2-CH_2-CH_2-$ or $-CH_2-CHG^1-CHG^2-CH_2-$, wherein $G^1$ and $G^2$ are both hydrogen or together with the carbon atoms to which they are attached form a fused phenyl group;
$R^8$ and $R^9$ are both hydrogen or together form $=O$;
$R^{14}$ is selected from the group consisting of
phenyl substituted with one or two substituents independently selected from the group consisting of hydroxy, hydroxyalkyl, cyano, amino, aminoalkyl, alkylamino, and dialkylamino;
naphthyl optionally substituted with one or two substituents independently selected from the group consisting of alkyl, alkoxy, halogen, haloalkyl, hydroxy, hydroxyalkyl, cyano, amino, aminoalkyl, alkylamino, and dialkylamino;
quinolinyl;
pyridyl; and
phenyl substituted with phenyl, benzyl, phenoxy, or benzyloxy, wherein each phenyl ring is optionally substituted with one or two substituents independently selected from the group consisting of halogen, haloalkyl, alkyl, alkoxy, hydroxy, amino and cyano;
$R^{15}$ is phenyl or naphthyl, either of which is optionally substituted with one or two substituents independently selected from the group consisting of alkyl, alkoxy, halogen, haloalkyl, amino, alkylamino and dialkylamino;
D is $C=O$, $-CH=CH-$, or absent;
m is 0 or 1; and
o is 0, 1, 2, or 3;
with the proviso that when Z is $Z^4$, then $R^3$ is cyclopropyl.

2. A compound having the Formula I:

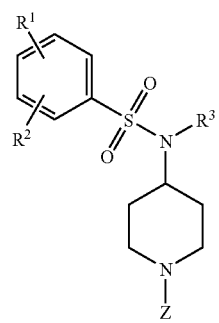

or a pharmaceutically acceptable salt thereof, wherein:
$R^1$ and $R^2$ are each independently selected from the group consisting of hydrogen, alkyl, haloalkyl, halogen, alkoxy, haloalkoxy, cyano, nitro, amino, and hydroxy;
$R^3$ is selected from the group consisting of alkyl, alkenyl, cycloalkyl, cycloalkylalkyl, alkoxyalkyl, hydroxyalkyl, 2-tetrahydrofuranyl, 3-tetrahydrofuranyl, 2-tetrahydrofuranylalkyl, 3-tetrahydrofuranylalkyl, alkylsulfonylaminoalkyl, and aminocarbonylalkyl;

Z is selected from the group consisting of $Z^1$, $Z^3$, and $Z^4$, wherein

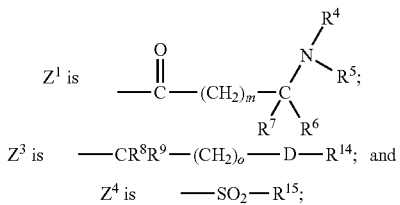

$Z^4$ is $-SO_2-R^{15}$;

$R^4$ and $R^5$ are each independently selected from the group consisting of hydrogen, alkyl, alkenyl, hydroxyalkyl, haloalkyl, alkylthiol, aminoalkyl and phenyl; or $R^4$ and $R^5$ together with the nitrogen atom to which they are attached form a 5- or 6-membered heterocyclic ring wherein one or more carbon atoms of the heterocyclic ring are optionally replaced with $NR^{16}$, O, or S, wherein $R^{16}$ is hydrogen or $C_{1-3}$alkyl;

$R^6$ is hydrogen and $R^7$ is selected from the group consisting of
alkyl;
hydroxyalkyl;
alkoxyalkyl;
haloalkyl;
aminoalkyl;
cycloalkyl;
phenyl optionally substituted with one or two substituents independently selected from the group consisting of alkyl, cycloalkyl, halogen, cyano, amino, alkylamino, dialkylamino, hydroxy, nitro, haloalkyl, and alkoxy;
benzyl optionally substituted with one or two substituents independently selected from the group consisting of alkyl, cycloalkyl, halogen, cyano, amino, alkylamino, dialkylamino, hydroxy, nitro, haloalkyl, and alkoxy; and
benzyloxyalkyl; or
$R^6$ and $R^7$ together with the carbon atom to which they are attached form a $C_{3-7}$cycloalkyl group, or
$R^7$ is hydrogen, $R^4$ is hydrogen or $C_{1-3}$ alkyl, and $R^5$ and $R^6$ together form a bridge $-CH_2-CH_2-CH_2-$ or $-CH_2-CHG^1$-$CHG^2-CH_2-$, wherein $G^1$ and $G^2$ are both hydrogen or together with the carbon atoms to which they are attached form a fused phenyl group;
$R^8$ and $R^9$ are both hydrogen or together form $=O$;
$R^{14}$ is selected from the group consisting of
phenyl substituted with one or two substituents independently selected from the group consisting of hydroxy, hydroxyalkyl, cyano, amino, aminoalkyl, alkylamino, and dialkylamino;
naphthyl optionally substituted with one or two substituents independently selected from the group consisting of alkyl, alkoxy, halogen, haloalkyl, hydroxy, hydroxyalkyl, cyano, amino, aminoalkyl, alkylamino, and dialkylamino;
quinolinyl;
pyridyl; and
phenyl substituted with phenyl, benzyl, phenoxy, or benzyloxy, wherein each phenyl ring is optionally substituted with one or two substituents independently selected from the group consisting of halogen, haloalkyl, alkyl, alkoxy, hydroxy, amino and cyano;

$R^{15}$ is phenyl or naphthyl, either of which is optionally substituted with one or two substituents independently selected from the group consisting of alkyl, alkoxy, halogen, haloalkyl, amino, alkylamino and dialkylamino;

D is $C=O$, $-CH=CH-$, or absent;

m is 0 or 1; and o is 0, 1, 2, or 3;

with the proviso that when Z is $Z^4$, then $R^3$ is cyclopropyl.

3. The compound of claim 1, wherein $R^3$ is selected from the group consisting of methyl, ethyl, iso-pentyl, iso-butyl, iso-propyl, cyclopropyl, cyclobutyl, cyclopentyl, cyclopropylmethyl, cyclopropylethyl, methoxymethyl, methoxyethyl, hydroxymethyl, hydroxyethyl, 3-tetrahydrofuranyl, 2-tetrahydrofuranylmethyl, 2-tetrahydrofuranylethyl, methylsulfonamidomethyl, methylsulfonamidoethyl, aminocarbonylmethyl, and aminocarbonylethyl.

4. The compound of claim 1, wherein $R^3$ is cyclopropyl, having the Formula II:

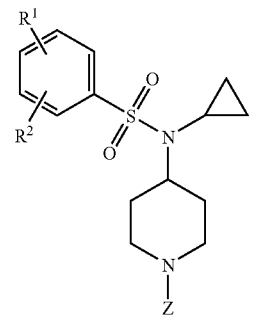

or a pharmaceutically acceptable salt thereof.

5. The compound of claim 1, wherein $R^1$ and $R^2$ are each independently selected from the group consisting of hydrogen, halogen, alkyl, haloalkyl, cyano, alkoxy, haloalkoxy, and nitro.

6. The compound of claim 5, wherein $R^1$ is hydrogen and $R^2$ is trifluoromethyl, or $R^1$ and $R^2$ are both hydrogen.

7. The compound of claim 4, wherein $R^2$ is trifluoromethyl in the meta-position of the phenyl ring and $R^1$ is hydrogen, having the Formula III:

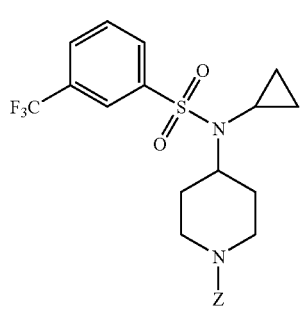

or a pharmaceutically acceptable salt thereof.

8. The compound of claim 1, wherein Z=Z$^1$, having the Formula IV:

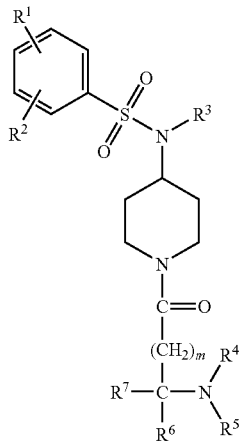

or a pharmaceutically acceptable salt thereof.

9. The compound of claim 8, wherein R$^4$ and R$^5$ are each independently selected from the group consisting of hydrogen, alkyl, hydroxyalkyl, and phenyl.

10. The compound of claim 8, wherein R$^4$ and R$^5$ together with the nitrogen atom to which they are attached form a 5- or 6-membered heterocyclic ring wherein one or more carbon atoms of the heterocyclic ring are optionally replaced with NR$^{16}$, O, or S, wherein R$^{16}$ is hydrogen or C$_{1-3}$alkyl.

11. The compound of claim 8, wherein R$^6$ is hydrogen and R$^7$ is methyl; propyl; iso-propyl; butyl; tert-butyl; sec-butyl; iso-butyl; hydroxymethyl; 1-hydroxyethyl; phenyl optionally substituted with one or two substituents independently selected from the group consisting of methyl, ethyl, propyl, iso-propyl, butyl, tert-butyl, halogen, cyano, amino, methylamino, dimethylamino, hydroxy, nitro, and trifluoromethyl; benzyl optionally substituted with one or two substituents independently selected from the group consisting of methyl ethyl, propyl, iso-propyl, butyl, tert-butyl, halogen, cyano, amino, methylamino, dimethylamino, hydroxy, nitro, and trifluoromethyl; 1-benzyloxyethyl; cyclopentyl; cyclohexyl; cyclopentylmethyl; or cyclohexylmethyl.

12. The compound of claim 8, wherein R$^6$ is hydrogen, R$^7$ is alkyl, and R$^4$ and R$^5$ are independently hydrogen, alkyl, or hydroxyalkyl, or R$^4$ and R$^5$ together with the nitrogen atom to which they are attached form a 5- or 6-membered heterocyclic ring wherein one or more carbon atoms of the heterocyclic ring are optionally replaced with NR$^{16}$, O, or S, wherein R$^{16}$ is hydrogen or C$_{1-3}$alkyl.

13. The compound of claim 8, wherein R$^6$ and R$^7$ together form cyclopentyl or cyclohexyl.

14. The compound of claim 8, wherein R$^7$ is hydrogen, R$^4$ is hydrogen or C$_{1-3}$ alkyl, and R$^5$ and R$^6$ together form a bridge —CH$_2$—CH$_2$—CH$_2$— or —CH$_2$—CHG$^1$-CHG$^2$-CH$_2$—, wherein G$^1$ and G$^2$ are both hydrogen or together with the carbon atoms to which they are attached form a fused phenyl group.

15. The compound of claim 8, wherein the configuration at the carbon atom to which —NR$^4$R$^5$ is attached is (S).

16. The compound of claim 8, having the Formula V:

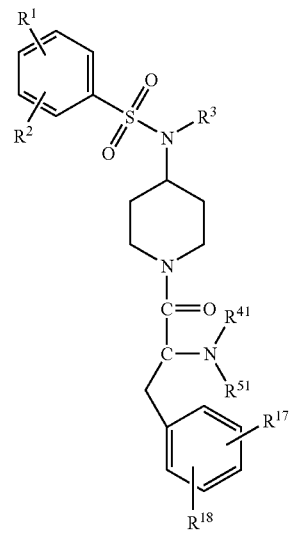

or a pharmaceutically acceptable salt thereof,
wherein:
R$^{41}$ and R$^{51}$ are each independently selected from the group consisting of hydrogen, alkyl, alkenyl, hydroxyalkyl, haloalkyl, and aminoalkyl; and
R$^{17}$ and R$^{18}$ are each independently selected from the group consisting of hydrogen, alkyl, cycloalkyl, halogen, cyano, amino, alkylamino, dialkylamino, hydroxy, nitro, haloalkyl, and alkoxy.

17. The compound of claim 16, wherein R$^{41}$ and R$^{51}$ are each independently selected from the group consisting of hydrogen, alkyl, and hydroxyalkyl.

18. The compound of claim 17, wherein R$^{41}$ and R$^{51}$ both are hydrogen, or R$^{41}$ is hydrogen and R$^{51}$ is C$_{1-3}$ alkyl.

19. The compound of claim 16, wherein R$^{17}$ and R$^{18}$ are each independently selected from the group consisting of hydrogen, C$_{1-6}$alkyl, C$_{3-6}$cycloalkyl, halogen, cyano, amino, C$_{1-3}$alkylamino, di(C$_{1-3}$)alkylamino, hydroxy, nitro, halo(C$_{1-6}$)alkyl, and C$_{1-6}$alkoxy.

20. The compound of claim 19, wherein R$^{17}$ and R$^{18}$ are both hydrogen, or R$^{17}$ is hydrogen and R$^{18}$ is methyl, tert-butyl, cyano, fluoro, methylamino, dimethylamino, trifluoromethyl, or methoxy.

21. The compound of claim 8, having the Formula VI:

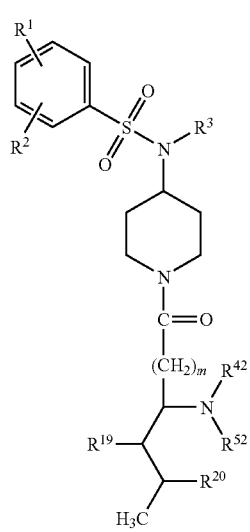

or a pharmaceutically acceptable salt thereof,
wherein:
$R^{42}$ and $R^{52}$ and are each independently selected from the group consisting of hydrogen, alkyl, alkenyl, hydroxyalkyl, haloalkyl, alkylthiol, and aminoalkyl; or $R^{42}$ and $R^{52}$ together with the nitrogen atom to which they are attached form a 5- or a 6-membered heterocyclic ring wherein one or more carbon atoms of the heterocyclic ring are optionally replaced with $NR^{16}$, O or S, wherein $R^{16}$ is hydrogen or $C_{1-3}$alkyl; and $R^{19}$ and $R^{20}$ are independently H or $CH_3$.

22. The compound of claim 21, wherein $R^{42}$ and $R^{52}$ are each independently selected from the group consisting of hydrogen, methyl, ethyl, hydroxymethyl, and hydroxyethyl.

23. The compound of claim 21, wherein $R^{42}$ and $R^{52}$ together with the nitrogen atom to which they are attached form a 5- or 6-membered heterocyclic ring selected from the group consisting of oxazolidinyl, isoxazolidinyl, pyrrolidinyl, pyrazolidinyl, imidazolidinyl, hexahydropyrimidinyl, piperidinyl, piperazinyl, 4-methylpiperazinyl, morpholinyl, thiomorpholinyl, and tetrahydropyridyl.

24. The compound of claim 21, wherein $R^{42}$ and $R^{52}$ are independently hydrogen, methyl or hydroxyethyl; or $R^{42}$ and $R^{52}$ together with the nitrogen atom to which they are attached form 1-pyrrolidinyl, 4-thiomorpholinyl, or 4-methylpiperazinyl.

25. The compound of 21, wherein $R^{19}$ and $R^{20}$ are both H when $R^{42}$ and $R^{52}$ together form the 5- or 6-membered heterocyclic ring.

26. The compound of claim 21, wherein $R^{42}$ and $R^{52}$ are both hydrogen or $R^{42}$ is hydrogen and $R^{52}$ is alkyl.

27. The compound of claim 21, wherein m is 1.

28. The compound of claim 1, wherein $Z=Z^3$, having the Formula VIII:

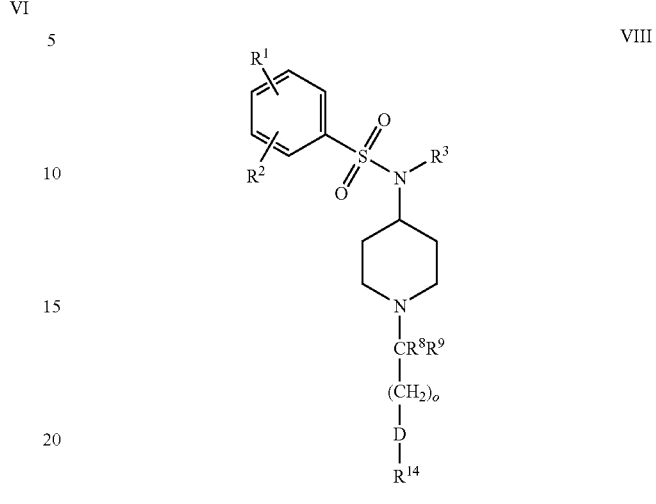

or a pharmaceutically acceptable salt thereof.

29. The compound of claim 28, wherein $R^{14}$ is selected from the group consisting of:
phenyl substituted with one or two substituents independently selected from the group consisting of hydroxy, hydroxyalkyl, cyano, amino, aminoalkyl, alkylamino, and dialkylamino;
phenyl substituted with phenyl, benzyl, phenoxy or benzyloxy, wherein each phenyl ring is optionally substituted with one or two substituents selected from the group consisting of halogen, haloalkyl, alkyl, alkoxy, hydroxy, amino, and cyano; naphthyl; quinolinyl; and pyridyl.

30. The compound of claim 28, wherein $R^{14}$ is naphthyl, quinolinyl or pyridyl each of which is unsubstituted.

31. The compound of claim 28, wherein $R^8$ and $R^9$ are both hydrogen when $R^{14}$ is one of
naphthyl;
quinolinyl;
pyridyl;
phenyl substituted with phenyl optionally substituted with halogen, haloalkyl, alkyl, alkoxy, hydroxy, amino, or cyano;
phenyl substituted with benzyl optionally substituted with halogen, haloalkyl, alkyl, alkoxy, hydroxy, amino, or cyano;
phenyl substituted with phenoxy optionally substituted with halogen, haloalkyl, alkyl, alkoxy, hydroxy, amino, or cyano; or
phenyl substituted with benzyloxy optionally substituted with halogen, haloalkyl, alkyl, alkoxy, hydroxy, amino, or cyano.

32. The compound of claim 28, wherein $R^8$ and $R^9$ together form =O.

33. The compound of claim 28, wherein $R^8$ and $R^9$ are both hydrogen or together form =O, and D is absent or —CH=CH—.

34. The compound of claim 32, wherein D is C=O.

35. The compound of claim 28, wherein o is 0 or 1.

36. The compound of claim 1, wherein Z=Z⁴, having the Formula IX:

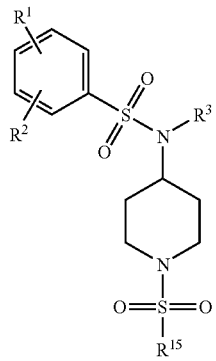

or a pharmaceutically acceptable salt thereof.

37. The compound of claim 36, wherein $R^{15}$ is phenyl or naphthyl either of which is substituted with one or more substituents independently selected from the group consisting of alkyl, alkoxy, halogen, haloalkyl, amino, alkylamino and dialkylamino.

38. The compound of claim 36, wherein $R^{15}$ is naphthyl substituted with amino, alkylamino or dialkylamino.

39. The compound of claim 1, wherein said compound is:
(2S)N-1-butyl-N-[1-(4-methyl-2-methylaminopentanoyl) piperidin-4-yl]-3-trifluoromethylbenzenesulfonamide;
(2S)N-1-pentyl-N-[1-(4-methyl-2-methylaminopentanoyl)piperidin-4-yl]-3-trifluoromethylbenzenesulfonamide;
(2S)N-cyclopropyl-N-[1-(4-methyl-2-methylaminopentanoyl)-piperidin-4-yl]-3-methoxybenzenesulfonamide;
(2S)N-[1-(4-Methyl-2-methylaminopentanoyl)piperidin-4-yl]-N-(tetrahydrofuran-2-yl)methyl-3-trifluoromethylbenzenesulfonamide;
(2S)N-cyclopropyl-N-[1-(4-methyl-2-methylaminopentanoyl)-piperidin-4-yl]-3-difluoromethoxybenzenesulfonamide;
(2S)N-cyclopropyl-N-[1-(4-methyl-2-methylaminopentanoyl)-piperidin-4-yl]-3-cyanobenzenesulfonamide;
(2S)N-cyclopropyl-N-[1-(4-methyl-2-methylaminopentanoyl)-piperidin-4-yl]-3-chlorobenzenesulfonamide;
(2S)N-cyclopropyl-N-[1-(4-methyl-2-methylaminopentanoyl)-piperidin-4-yl]-3-methylbenzenesulfonamide;
(2S)N-methyl-N-[1-(4-methyl-2-methylaminopentanoyl) piperidin-4-yl]-3-trifluoromethylbenzenesulfonamide;
(2S)N-cyclopropyl-N-[1-(4-methyl-2-methylaminopentanoyl)-piperidin-4-yl]-3-nitrobenzenesulfonamide;
(2S)N-(2-hydroxyethyl)-N-[1-(4-methyl-2-methylaminopentanoyl)-piperidin-4-yl]-3-trifluoromethylbenzenesulfonamide;
(2S)N-cyclopropylmethyl-N-[1-(2-methylamino-4-methyl-pentanoyl)-piperidin-4-yl]-3-trifluoromethylbenzenesulfonamide;
(2S)N-cyclopentyl-N-[1-(4-methyl-2-methylamino-pentanoyl)piperidin-4-yl]-3-trifluoromethylbenzenesulfonamide;
(2S)N-isopropyl-N-[1-(4-methyl-2-methylaminopentanoyl)-piperidin-4-yl]-3-trifluoromethylbenzenesulfonamide;
(2S)N-[1-(4-methyl-2-methylaminopentanoyl)piperidin-4-yl]-N-(tetrahydrofuran-3-yl)-3-trifluoromethylbenzenesulfonamide;
N-cyclopropyl-N-[1-(4-quinolinylmethyl)piperidin-4-yl]-3-trifluoromethyl-benzenesulfonamide;
N-[1-(1-aminocyclopentan-1-carbonyl)piperidin-4-yl]-N-cyclopropyl-3-trifluoromethylbenzenesulfonamide;
N-cyclopropyl-N-[1-(1,2,3,4-tetrahydroisoquinolin-3-carbonyl)piperidin-4-yl]-3-trifluoromethylbenzenesulfonamide;
N-cyclopropyl-N-[1-(N-methylpyrrolidin-2-carbonyl)piperidin-4-yl]-3-trifluoromethylbenzenesulfonamide;
N-cyclopropyl-N-[1-(2-methylamino-3-o-tolylpropionyl) piperidin-4-yl]-3-trifluoromethylbenzenesulfonamide; or
(2R)N-[1-(2-amino-2-cyclohexylethanoyl)piperidin-4-yl]-N-cyclo-propyl-3-trifluoromethylbenzenesulfonamide;
or a pharmaceutically acceptable salt thereof.

40. A pharmaceutical composition, comprising the compound of claim 1 or 2, or a pharmaceutically acceptable salt thereof, and a pharmaceutically acceptable carrier.

41. A method for treating or ameliorating pain in a mammal, comprising administering an effective amount of a compound of Formula I as set forth in claim 1 or 2, or a pharmaceutically acceptable salt thereof, to a mammal in need of such treatment or amelioration.

42. The method of claim 41, wherein the method is for treating or ameliorating pain selected from the group consisting of chronic pain, neuropathic pain, acute pain, and surgical pain.

* * * * *